United States Patent
Yamazaki et al.

(10) Patent No.: US 6,653,334 B1
(45) Date of Patent: Nov. 25, 2003

(54) BENZOXAZOLE COMPOUND AND PHARMACEUTICAL COMPOSITION CONTAINING THE SAME

(75) Inventors: Yukiyoshi Yamazaki, Higashimurayama (JP); Tsutomu Toma, Kodaira (JP); Masahiro Nishikawa, Higashimurayama (JP); Hidefumi Ozawa, Hachiouji (JP); Ayumu Okuda, Higashimurayama (JP); Kazutoyo Abe, Lille (FR); Soichi Oda, Nishikasugai-gun (JP)

(73) Assignee: Kowa Co., Ltd., Nagoya (JP)

(*) Notice: Subject to any disclaimer, the term of this patent is extended or adjusted under 35 U.S.C. 154(b) by 0 days.

(21) Appl. No.: 10/329,547

(22) Filed: Dec. 27, 2002

(51) Int. Cl.[7] .......................... A61K 31/423; A61P 3/10; C07D 263/58
(52) U.S. Cl. ........................................ 514/375; 548/222
(58) Field of Search ........................... 548/222; 514/375

(56) References Cited

FOREIGN PATENT DOCUMENTS

WO    WO 02/46176    *   6/2002

OTHER PUBLICATIONS

Cell, vol. 97, pp. 161–163, "A Unified Nomenclature System for TRE Nuclear Receptor Superfamily", Apr. 16, 1999.

D. Auboeuf, et al., Diabetes, vol. 46, pp. 1319–1327, "Tissue Distribution and Quantification of the Expression of mRNAs of Peroxisome Proliferator–Activated Receptors and Liver X Receptor–α in Humans", Aug. 1997.

J. Auwerx, et al., Journal of Atherosclerosis and Thrombosis, vol. 3, No. 2, pp. 81–89, "Regulation of Triglyceride Metabolism by PPARs : Fibrates and Thiazolidinediones Have Distinct Effects", 1996.

Y. Barak, et al., Proc. Natl. Acad. Sci., vol. 99, No. 1, pp. 303–308, "Effects of Peroxisome Proliferator–Activated Receptor δ on Placentation, Adiposity, and Colorectal Cancer", Jan. 8, 2002.

J. Berger, et al., Endocrinology, vol. 137, No. 10, pp. 4189–4195, "Thiazolidinediones Produce a Conformational Change in Peroxisomal Proliferator–Activated Receptor–γ: Binding and Activation Correlate with Antidiabetic Actions in db/db Mice", 1996.

O. Boussif, et al., Proc. Natl. Acad. Sci., vol. 92, pp. 7297–7301, "A Versatile Vector for Gene and Oligonucleotide Transfer into Cells in Culture and In Vivo: Polyethylenimine", Aug. 1995.

D. R. Buckle, et al., Bioorganic & Medicinal Chemistry Letters, vol. 6, No. 17, pp. 2121–2126, "Non Thiazolidinedione Antihyperglycaemic Agents. 1: α–Heteroatom Substituted β–Phenylpropanoic Acids", 1996.

D. R. Buckle, et al., Bioorganic & Medicinal Chemistry Letters, vol. 6, No. 17, pp. 2127–2130, "Non–Thiazolidinedione Antihyperglycaemic Agents. 2: α–Carbon Substituted β–Phenylpropanoic Acids", 1996.

C. Dreyer, et al., Cell, vol. 68, pp. 879–887, "Control of the Peroxisomal β–Oxidation Pathway by a Novel Family of Nuclear Hormone Receptors", Mar. 6, 1992.

J–C. Fruchart, et al., Current Opinion in Lipidology, vol. 10, pp. 245–257, "Peroxisome Proliferator–Activated Receptor–Alpha Activators Regulate Genes Governing Lipoprotein Metabolism, Vascular Inflammation and Atherosclerosis", 1999.

F. J. Gonzales, et al., Journal of the National Cancer Institute, vol. 90, No. 22, pp. 1702–1709, "Mechanism of Action of the Nongenotoxic Peroxisome Proliferators: Role of the Peroxisome Proliferator–Activated Receptor α", Nov. 18, 1998.

I. Issemann, et al., Nature, vol. 347, pp. 645–650, "Activation of a Member of the Steroid Hormone Receptor Superfamily by Peroxisome Proliferators", Oct. 18, 1990.

J. M. Lehmann, et al., The Journal of Biological Chemistry, vol. 270, No. 22, pp. 12953–12956, "An Antidiabetic Thiazoldinedione is a High Affinity Ligand for Peroxisome Proliferator–Activated Receptor γ (PPAR$_\gamma$)", Jun. 2, 1995.

J. L. Oberfield, et al., Proc. Natl. Acad. Sci., vol. 96, pp. 6102–6106, "A Peroxisome Proliferator–Activated Receptor γ Ligand Inhibits Adipocyte Differentiation", May 1999.

A. Okuno, et al., J. Clin. Invest, vol. 101, No. 6, pp. 1354–1361, "Troglitazone Increases the Number of Small Adipocytes Without the Change of White Adipose Tissue Mass in Obese Zucker Rats", Mar. 1998.

W. R. Oliver, Jr., et al., Proc. Natl. Acad. Sci., vol. 98, No. 9, pp. 5306–5311, "A Selective Peroxisome Proliferator–Activated Receptor δ Agonist Promotes Reverse Cholesterol Transport", Apr. 24, 2001.

(List continued on next page.)

Primary Examiner—Robert W. Ramsuer
(74) Attorney, Agent, or Firm—Oblon, Spivak, McClelland, Maier & Neustadt, P.C.

(57) ABSTRACT

The present invention is directed to a benzoxazole compound represented by the following formula (1):

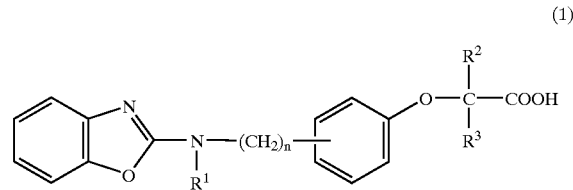

(wherein $R^1$ represents an alkyl group, a $C_{6-10}$ aryl-$C_{1-8}$ alkyl group, etc.; each of $R^2$ and $R^3$, which are identical to or different from each other, represents a hydrogen atom, a methyl group, or an ethyl group; and n represents a number of 1 to 3) or a salt thereof and to a pharmaceutical compound containing the same. These compounds electively activate PPARα.

8 Claims, 1 Drawing Sheet

OTHER PUBLICATIONS

M. J. Reginato, et al., Trends Endocrinol. Metab., vol. 10, No. 1, pp. 9–13, "Mechanisms by Which Thiazolidinediones Enhance Insulin Action", 1999.

S. J. Robins, Journal of Cardiovascular Risk, vol. 8, No. 4, pp. 195–201, "PPAR α Ligands and Clinical Trials: Cardiovascular Risk Reduction with Fibrates", 2001.

K. Schoonjans, et al., Biochimica et Biophysica Acta, vol. 1302, pp. 93–109, "The Peroxisome Proliferator Activated Receptors (PPARs) and Their Effects on Lipid Metabolism and Adipocyte Differentiation", 1996.

B. Staels, et al., Current Pharmaceutical Design, vol. 3, No. 1, pp. 1–14, "Role of PPAR in the Pharmacological Regulation of Lipoprotein Metabolism by Fibrates and Thiazolidinediones", 1997.

L. B. Tan, et al., The Lancet, vol. 349, p. 952, "GLITAZONES and NIDDM", Mar. 29, 1997.

I. Pineda Torra, et al., Current Opinion in Lipidology, vol. 10, pp. 151–159, "Peroxisome Proliferator–Activated Receptor Alpha in Metabolic Disease, Inflammation, Atherosclerosis and Aging", 1999.

J. Valmecq, et al., The Lancet, vol. 354, pp. 141–148, "Medical Significance of Peroxisome Proliferator–Activated Receptors", Jul. 10, 1999.

H. Vosper, et al., The Journal of Biological Chemistry, vol. 276, No. 47, pp. 44258–44265, "The Peroxisome Proliferator–Activated Receptor δ Promotes Lipid Accumulation in Human Macrophages", Nov. 23, 2001.

N. Vu–Dac, et al., The Journal of Biological Chemistry, vol. 269, No. 49, pp. 31012–31018, "Negative Regulation of the Human Apolipoprotein A–I Promoter by Fibrates can be Attenuated by the Interaction of the Peroxisome Proliferator–Activated Receptor with its Response Element", Dec. 9, 1994.

T. M. Willson, et al., Journal of Medicinal Chemistry, vol. 43, No. 4, pp. 527–550, "The PPARs: From Orphan Receptors to Drug Discovery", Feb. 24, 2000.

H. M. Wright, et al., The Journal of Biological Chemistry, vol. 275, No. 3, pp. 1873–1877, "A Synthetic Antogonist for the Peroxisome Proliferator–Activated Receptor δ Inhibits Adipocyte Differentiation", Jan. 21, 2000.

T. Yamauchi, et al., The Journal of Clinical Investigation, vol. 108, No. 7, pp. 1001–1013, "Inhibition of RXR and PPARδ Ameliorates Diet–Induced Obesity and Type 2 Diabetes", Oct. 2001.

P. W. Young, et al., The Journal of Pharmacology and Experimental Therapeutics, vol. 284, No. 2, pp. 751–759, "Identification of High–Affinity Binding Sites for the Insulin Sensitizer Rosiglitazone (BRL–49653) in Rodent and Human Adipocytes Using a Radioiodinated Ligand for Peroxisomal Proliferator–Activated Receptor δ", 1998.

* cited by examiner

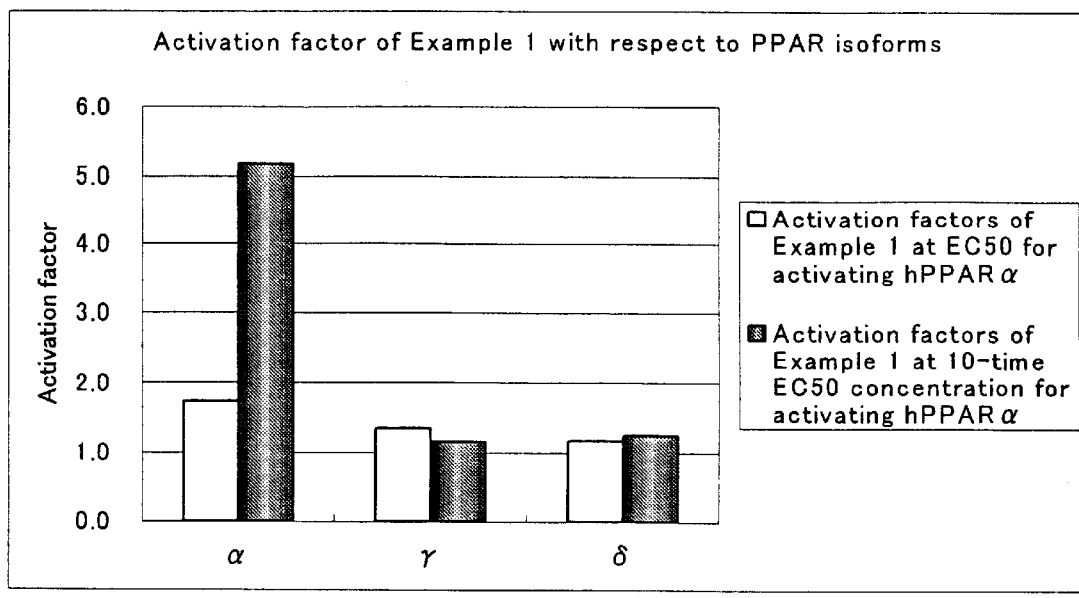

BENZOXAZOLE COMPOUND AND PHARMACEUTICAL COMPOSITION CONTAINING THE SAME

TECHNICAL FIELD

The present invention relates to a benzoxazole compound which selectively activates, among peroxisome proliferator-activated receptors (PPARs), PPARα, and is usefully employed as a drug for preventing and/or treating diseases including hyperlipidemia, arteriosclerosis, diabetes, complications of diabetes, inflammation, and heart diseases. The invention also relates to a pharmaceutical composition containing the compound.

BACKGROUND ART

PPARs are known to be a family of nuclear receptors, and three sub-types thereof (α, γ, δ) have been already identified (Nature, 347, 645–650, 1990; Cell, 68, pp. 879–887, 1992; Cell, 97, pp. 161–163, 1999; Biochim. Biophys. Acta., 1302, pp. 93–109, 1996; and Journal of Medicinal Chemistry, 43, pp. 527–550, 2000).

Among the three sub-types, PPARα is expressed predominantly in the liver and is known to be activated by a plasticizer or a fibrate-type drug such as Wy 14643 or a commercially available pharmaceutical; e.g., clofibrate, fenofibrate, bezafibrate, or gemfibrosil (Journal of the National Cancer Institute, 90, 1702–1709, 1998, Current Opinion in Lipidology, 10, pp. 245–257, 1999).

In mammals, activation of PPARα is known to promote β oxidation of fatty acids and lower a blood triglyceride level. In humans, the total level of blood lipids including low-density lipoprotein (LDL) cholesterol and very low-density lipoprotein (VLDL) cholesterol decreases. Thus, a PPARα-activator is useful as a drug for preventing and/or treating a disease such as hyperlipidemia. In addition, the PPARα-activator, which increases the high-density lipoprotein (HDL) cholesterol level and, in blood vessels, suppresses expression of VCAM-1 (a type of cell adhesion molecules), is considered to be usefully employed as a drug for preventing and/or treating diseases such as arteriosclerosis. Furthermore, the PPARα-activator is considered to be usefully employed as a drug for preventing and/or treating diseases such as diabetes, inflammatory disease, and heart diseases (Journal of Atherosclerosis and Thrombosis, 3, pp. 81–89, 1996; Current Pharmaceutical Design, 3, pp. 1–14, 1997, Current Opinion in Lipidology, 10, pp. 151–159, 1999; Current Opinion in Lipidology, 10, pp. 245–257, 1999; The Lancet, 354, pp. 141–148, 1999; Journal of Medicinal Chemistry, 43, pp. 527–550, 2000; and Journal of Cardiovascular Risk, 8, pp. 195–201, 2001).

PPARγ, which is expressed predominantly in adipocytes, is known to play an important role in differentiating and proliferating adipocyte. Examples of known activators for PPARγ include thiazolidine derivative drugs such as troglitazone, pioglitazone, and rosiglitazone. These drugs are known to transform fully differentiated adipocytes having reduced insulin sensitivity into small adipocytes having high insulin sensitivity, thereby improving insulin resistance (Journal of Biological Chemistry, 270, 12953–12956, 1995; Endocrinology, 137, pp. 4189–4195, 1996; Trends Endocrinol. Metab., 10, pp. 9–13, 1999; and J. Clin. Invest., 101, pp. 1354–1361, 1998). However, PPARγ has been reported to have the adverse effects on humans of increasing the amount of fat and body weight and causing obesity (The Lancet, 349, pp. 952, 1997). Recently, it is also reported that a PPARγ antagonist possibly improves insulin resistance (Proc. Natl. Acad. Sci., 96, pp. 6102–6106, 1999; The Journal of Biological Chemistry, 275, pp. 1873–1877, 2000; and J. Clin. Invest., 108, 1001–1013, 2001).

PPARδ, which is present ubiquitously in the body, is known to take part in lipid metabolism. However, only a few high-selectivity PPARδ activators have been reported, and the biological meaning of PPARδ remains unclear. At present, the structures of PPARδ activators are reported in a wide range of literature (Diabetes, 46, 1319–1327, 1997; and Journal of Medicinal Chemistry, 43, pp. 527–550, 2000). In a recent report, GW 501516, a type of PPARδ activator, elevates HDL level in monkeys (Proc. Natl. Acad. Sci., 98, pp. 5306–5311, 2001). However, a compound F, a PPARδ activator, disclosed in WO 97/28149 exerts an unfavorable effect of accumulating lipids in human macrophages (Journal of Biological Chemistry, 276, pp. 44258–44265, 2001). In addition, results of an experiment employing PPARδ-deficient mice indicate that activation of PPARδ induces lipid accumulation action (Proc. Natl. Acad. Sci., 99, pp. 303–308, 2002). These phenomena accelerate arteriosclerosis and reduce the effect of treating arteriosclerosis. Therefore, effects of PPARδ on treatment of arteriosclerosis remain unelucidated.

As described above, a PPARα-selective activator having low activity to PPARγ and to PPARδ is expected to be useful for preventing and/or treating, without accompanying obesity or increase in body weight, diseases such as hyperlipidemia, arteriosclerosis, diabetes, complications of diabetes, inflammation, and heart diseases.

WO 94/01420 discloses the following compounds having a benzoxazole skeleton (Bioorg. Med. Chem. Lett., 6, pp. 2121–2126, 1996; and Bioorg. Med. Chem. Lett., 6, pp. 2127–2130, 1996)

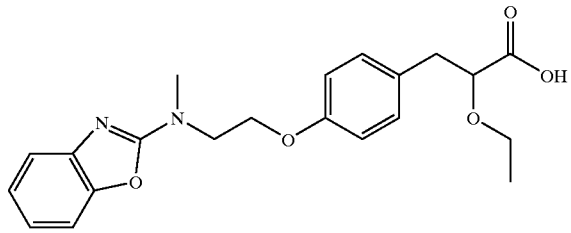

WO 96/04260 discloses the following compounds (J. Pharmacol. Exp. Ther., 284, pp. 751–759, 1998).

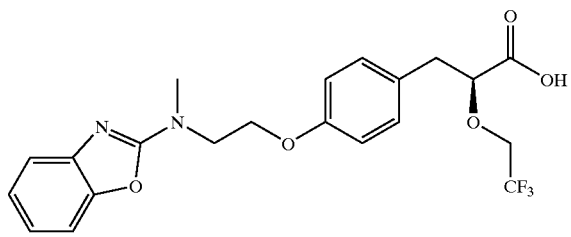

WO 97/25042 and WO 97/31907 also disclose compounds having a benzoxazole moiety. However, these compounds do not exhibit PPARα-selective activation effect, but rather exert a strong PPARγ activation effect.

WO 02/46176 discloses compounds represented by the following formula:

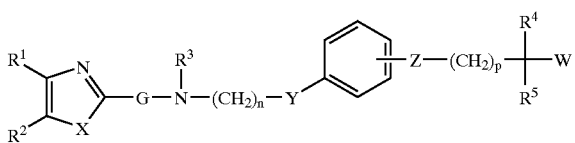

(wherein each of $R^1$ and $R^2$ represents a hydrogen atom, a halogen atom, a nitro group, a C1 to C8 alkyl group, a C1 to C8 alkoxy group, or a C6 to C10 aryl group, or $R^1$ and $R^2$, together with the carbon atoms to which they are attached, may form a benzene ring; X represents an oxygen atom, a sulfur atom, —$NR^0$— ($R^0$ represents a hydrogen atom or a C1 to C8 alkyl group), or —CH=CH—; G represents a single bond or a carbonyl group; $R^3$ represents a C1 to C8 alkyl group, a C2 to C8 alkenyl group, a C2 to C8 alkyl group, a C3 to C7 cycloalkyl group, a C1 to C8 alkyl group substituted by a C3 to C7 cycloalkyl group, a C6 to C10 aryl group, an arylalkyl group (formed of a C6 to C10 aryl moiety and a C1 to C8 alkyl moiety), a heterocyclic group, or a heterocyclicalkyl group (containing a C1 to C8 alkyl moiety); n is an integer of 0 to 5; Y represents —$CH_2$—, a carbonyl group, or —CH=CH—; Z represents an oxygen atom or a sulfur atom; p represents an integer of 0 to 5; each of $R^4$ and $R^5$ represents a hydrogen atom or a C1 to C8 alkyl group; and W represents a carboxyl group, a C2 to C8 alkoxycarbonyl group, a sulfonic acid group, a phosphonic acid group, a cyano group, or a tetrazolyl group).

However, WO 02/46176 provides a specific description only in terms of thiazole compounds (X in the above formula is a sulfur atom), and no specific description is provided in terms of benzoxazole compounds. The specification discloses activation effect on each sub-type of PPARs. The disclosed compounds activate all sub-types of PPARα, PPARγ, and PPARδ, and thus are not regarded as PPARα-selective activators.

DISCLOSURE OF THE INVENTION

The present inventors have carried out extensive studies in order to find a compound which selectively activates PPARα among other PPARs, and have found that a benzoxazole compound represented by the following formula (1) selectively activates PPARα and is useful as a drug for preventing and/or treating, without accompanying obesity or increase in body weight, diseases including hyperlipidemia, arteriosclerosis, diabetes, complications of diabetes, inflammation, and heart diseases. The present invention has been accomplished on the basis of this finding.

Accordingly, the present invention provides a benzoxazole compound represented by the following formula (1):

(1)

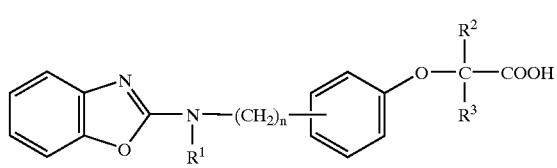

(wherein $R^1$ represents a hydrogen atom, a $C_{1-8}$ alkyl group, a $C_{2-8}$ alkenyl group, a $C_{2-8}$ alkynyl group, a $C_{3-7}$ cycloalkyl group, a $C_{3-7}$ cycloalkyl-$C_{1-8}$ alkyl group, a $C_{6-10}$ aryl-$C_{1-8}$ alkyl group (the $C_{6-10}$ aryl moiety may have one or two substituents selected from a halogen atom, a hydroxyl group, a nitro group, an amino group, a di-$C_{1-4}$ alkylamino group, a $C_{1-4}$ alkyl group, a $C_{1-4}$ alkoxy group, a benzyloxy group, a phenylsulfonylmethyl group, and a $C_{1-4}$ alkanesulfonyloxy group), a pyridyl-$C_{1-8}$ alkyl group, a $C_{1-8}$ alkoxycarbonyl-$C_{1-8}$ alkyl group, or a carboxy-$C_{1-8}$ alkyl group; $R^2$ and $R^3$ may be the same or different and represent a hydrogen atom, a methyl group, or an ethyl group; and n represents a number of 1 to 3) or a salt thereof.

The present invention also provides a pharmaceutical composition containing a benzoxazole compound represented by the above formula (1) or a salt thereof and a pharmaceutically acceptable carrier.

The present invention also provides a drug containing, as an active ingredient, a compound represented by the above formula (1) or a salt thereof.

The present invention also provides a use, for producing a drug, of a compound represented by the above formula (1) or a salt thereof.

The present invention also provides a method for treating a disease selected from hyperlipidemia, arteriosclerosis, diabetes, complications of diabetes, inflammation, and heart diseases, the method being characterized by administering a compound represented by the above formula (1) or a salt thereof in an effective amount.

BRIEF DESCRIPTION OF THE DRAWING

FIG. 1 is a chart showing the activation factor of compound of Example 1 to PPAR isoforms.

BEST MODE FOR CARRYING OUT THE INVENTION

In formula (1), the $C_{1-8}$ alkyl groups represented by $R^1$ include linear or branched alkyl groups. Examples of these groups include methyl, ethyl, n-propyl, isopropyl, n-butyl, isobutyl, sec-butyl, tert-butyl, n-pentyl, isopentyl, n-hexyl, isohexyl, n-heptyl, and n-octyl. Of these, the following are particularly preferred: ethyl, n-propyl, isopropyl, n-pentyl, isopentyl, n-hexyl, n-heptyl, and n-octyl.

The $C_{2-8}$ alkenyl groups represented by $R^1$ include linear or branched alkenyl groups. Examples of these groups include vinyl, allyl, butenyl, pentenyl, and hexenyl, with hexenyl being particularly preferred.

The $C_{2-8}$ alkynyl groups represented by $R^1$ include linear or branched alkynyl groups. Examples of these groups include propargyl and butynyl, with butynyl being particularly preferred.

The $C_{3-7}$ cycloalkyl groups represented by $R^1$ include cyclopropyl, cyclobutyl, cyclopentyl, cyclohexyl, and cycloheptyl, with cyclohexyl being particularly preferred.

Of the $C_{3-7}$ cycloalkyl-$C_{1-8}$ alkyl groups represented by $R^1$, $C_{3-7}$ cycloalkyl-$C_{1-4}$ alkyl are preferred. Specific examples of these groups include cyclopropylmethyl, cyclopropylethyl, cyclohexylmethyl, cyclohexylethyl, and cyclohexylpropyl.

Of the $C_{6-10}$ aryl-$C_{1-8}$ alkyl groups represented by $R^1$, $C_{6-10}$ aryl-$C_{1-4}$ alkyl are preferred, and phenyl-$C_{1-4}$ alkyl and naphthyl-$C_{1-4}$ alkyl are more preferred. Specific examples of these groups include benzyl, phenethyl, phenylpropyl, phenylbutyl, naphthylmethyl, naphthylethyl, and naphthylpropyl, with phenyl-$C_{1-4}$ alkyl being more preferred, and benzyl being particularly preferred.

The $C_{6-10}$ aryl moieties of the $C_{6-10}$ aryl-$C_{1-8}$ alkyl groups may have one or two substituents selected from halogen atoms, a hydroxy group, a nitro group, an amino group, di-$C_{1-4}$ alkylamino groups, $C_{1-4}$ alkyl groups, $C_{1-4}$ alkoxy groups, a benzyloxy group, a phenylsulfonylmethyl group, and $C_{1-4}$ alkanesulfonyloxy groups. Examples of the halogen atoms include chlorine, bromine, and fluorine. Examples of the di-$C_{1-4}$ alkylamino groups include dimethylamino, diethylamino, and diisopropylamino. Examples of the $C_{1-4}$ alkyl groups include methyl, ethyl, and isopropyl. Examples of the $C_{1-4}$ alkoxy groups include methoxy, ethoxy, n-propoxy, isopropoxy, and butoxy. Examples of the $C_{1-4}$ alkanesulfonyloxy groups include methanesulfonyloxy, ethanesulfonyloxy, and propanesulfonyloxy. Of the listed substituents of the aryl moieties, one or two substituents selected from halogen atoms, a nitro group, and di-$C_{1-4}$ alkylamino groups are more preferred; halogen atoms are still more preferred; and chlorine atom is particularly preferred.

The pyridyl-$C_{1-8}$ alkyl groups represented by $R^1$ are preferably pyridyl-$C_{1-4}$ alkyl groups. Specific examples of these groups include pyridylmethyl, pyridylethyl, and pyridylpropyl. The $C_{1-8}$ alkoxycarbonyl-$C_{1-8}$ alkyl groups represented by $R^1$ are preferably $C_{1-4}$ alkoxycarbonyl-$C_{1-4}$ alkyl groups. Specific examples of these groups include methoxycarbonylmethyl, ethoxycarbonylmethyl, propoxycarbonylmethyl, methoxycarbonylethyl, and ethoxycarbonylethyl. The carboxy-$C_{1-8}$ alkyl groups represented by $R^1$ are preferably carboxy-$C_{1-4}$ alkyl groups. Specific examples of these groups include carboxymethyl and carboxyethyl.

In relation to $R^2$ and $R^3$, the following cases are preferred: they are both hydrogen atoms; they are both methyl groups; one is a methyl group and the other is a hydrogen atom; or one is an ethyl group and the other is a hydrogen atom. Of these, the case where they are both methyl groups is particularly preferred.

In formula (1), preferably, $R^1$ is a $C_{1-8}$ alkyl group, a $C_{2-8}$ alkynyl group, or a $C_{6-10}$ aryl-$C_{1-8}$ alkyl group (wherein the $C_{6-10}$ aryl moiety may have one or two substituents selected from halogen atoms, a hydroxy group, a nitro group, an amino group, di-$C_{1-4}$ alkylamino groups, $C_{1-4}$ alkyl groups, $C_{1-4}$ alkoxy groups, a benzyloxy group, a phenylsulfonylmethyl group, and $C_{1-4}$ alkanesulfonyloxy groups).

More preferably, $R^1$ is a $C_{1-8}$ alkyl group, a $C_{2-8}$ alkynyl group, or a $C_{6-10}$ aryl-$C_{1-4}$ alkyl group (wherein the $C_{6-10}$ aryl moiety may have one or two substituents selected from halogen atoms, nitro group, and di-$C_{1-4}$ alkylamino groups).

Particularly preferably, $R^1$ is an ethyl group, an n-propyl group, an isopropyl group, an n-heptyl group, an n-octyl group, a butynyl group, a chlorobenzyl group, a nitrobenzyl group, a dimethylaminobenzyl group, a phenylpropyl group, a chlorophenylpropyl group, and a naphthylmethyl group.

Examples of the salts of the compounds represented by formula (1) of the present invention include alkali metal salts such as sodium salts and potassium salts; alkaline earth metal salts such as calcium salts and magnesium salts; organic base salts such as ammonium salts and trialkylamine salts; mineral acid salts such as hydrochloric acid salts and sulfuric acid salts; and organic acid salts such as acetic acid salts.

The compound of the present invention may include a solvate such as a hydrate or a geometrical (cis, trans) isomer or an optical isomer. These isomers also fall within the scope of the present invention.

Of the compounds of the present invention, examples of preferred compounds exhibiting high PPARα selectivity include the following compounds or salts thereof:

2-[3-[[N-(benzoxazol-2-yl)-N-(4-chlorobenzyl)]aminomethyl]phenoxy]-2-methylpropionic acid, 2-[3-[[N-(benzoxazol-2-yl)-N-n-octyl]aminomethyl]phenoxy]-2-methylpropionic acid, 2-[4-[[N-(benzoxazol-2-yl)-N-(naphth-1-ylmethyl)]aminomethyl]phenoxy]-2-methylpropionic acid, 2-[4-[[N-(benzoxazol-2-yl)-N-(2-nitrobenzyl)]aminomethyl]phenoxy]-2-methylpropionic acid, 2-[3-[[N-(benzoxazol-2-yl)-N-(4-dimethylaminobenzyl)]aminomethyl]phenoxy]-2-methylpropionic acid, 3-[[N-(benzoxazol-2-yl)-N-n-heptyl]aminomethyl]phenoxyacetic acid, 3-[[N-(benzoxazol-2-yl)-N-n-octyl]aminomethyl]phenoxyacetic acid, 2-[3-[[N-(benzoxazol-2-yl)-N-(3-phenylpropyl)]aminomethyl]phenoxy]butyric acid, 2-[3-[[N-(benzoxazol-2-yl)-N-(3-(4-chlorophenyl)propyl)]aminomethyl]phenoxy]butyric acid, 2-[3-[[N-(benzoxazol-2-yl)-N-n-octyl]aminomethyl]phenoxy]butyric acid, 2-[3-[[N-(benzoxazol-2-yl)-N-(3-(4-chlorophenyl)propyl)]aminomethyl]phenoxy]propionic acid, 2-[3-[[N-(benzoxazol-2-yl)-N-n-octyl]aminomethyl]phenoxy]propionic acid, 2-[3-[[N-(benzoxazol-2-yl)-N-(3-phenylpropyl)]aminomethyl]phenoxy]propionic acid, 2-[3-[[N-(benzoxazol-2-yl)-N-n-propyl]aminomethyl]phenoxy]propionic acid, 2-[4-[3-[N-(benzoxazol-2-yl)-N-ethyl]aminopropyl]phenoxy]-2-methylpropionic acid, 2-[3-[3-[N-(benzoxazol-2-yl)-N-(2-butynyl)]aminopropyl]phenoxy]-2-methylpropionic acid, 2-[4-[3-[N-(benzoxazol-2-yl)-N-n-propyl]aminopropyl]phenoxy]-2-methylpropionic acid, 2-[4-[3-[N-(benzoxazol-2-yl)-N-isopropyl]aminopropyl]phenoxy]-2-methylpropionic acid, 2-[3-[[N-(benzoxazol-2-yl)-N-(naphth-1-ylmethyl)]aminomethyl]phenoxy]-2-methylpropionic acid, and 2-[2-[3-[N-(benzoxazol-2-yl)-N-n-octyl]aminopropyl]phenoxy]-2-methylpropionic acid.

Of the above-listed compounds, 2-[3-[[N-(benzoxazol-2-yl)-N-(4-chlorobenzyl)]aminomethyl]phenoxy]-2-methylpropionic acid or salts thereof exhibit particularly high PPARα selectivity and thus are preferred.

The compounds of the present invention can be obtained in accordance with, for example, the following production methods described in reaction schemes A to I (in the following schemes, $R^1$, $R^2$, and $R^3$ have the same meanings as described above; each of $R^4$, $R^5$, and $R^6$ represents a C1-6 linear or branched alkyl group; and X represents a halogen atom such as fluorine, chlorine, bromine, or iodine).

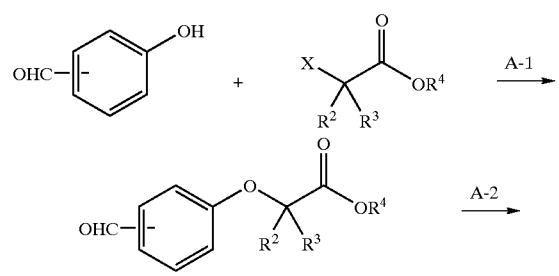

SCHEME A

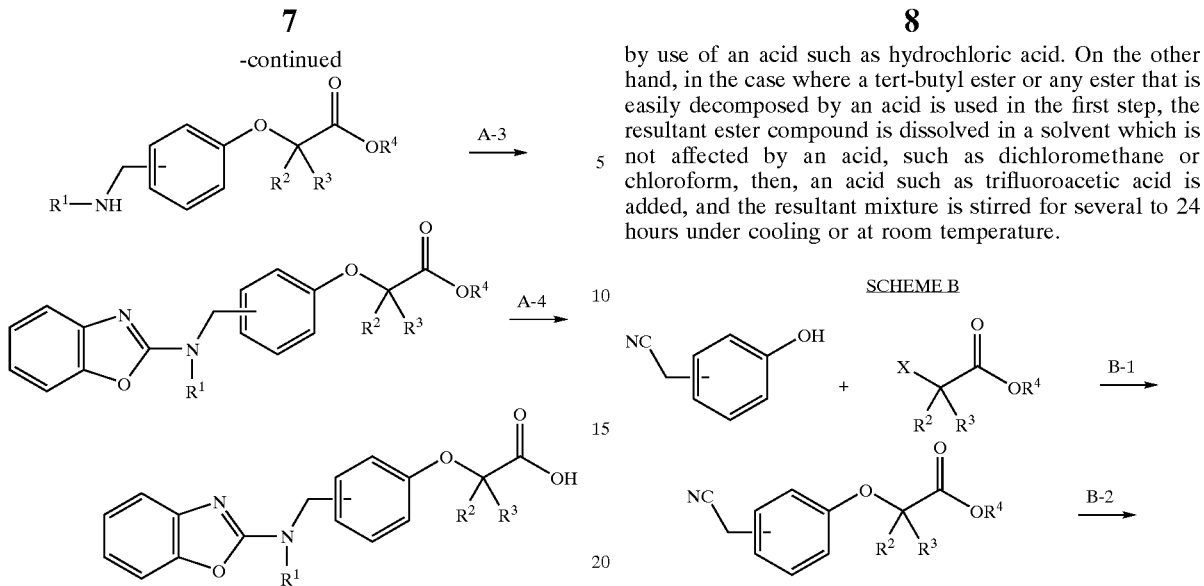

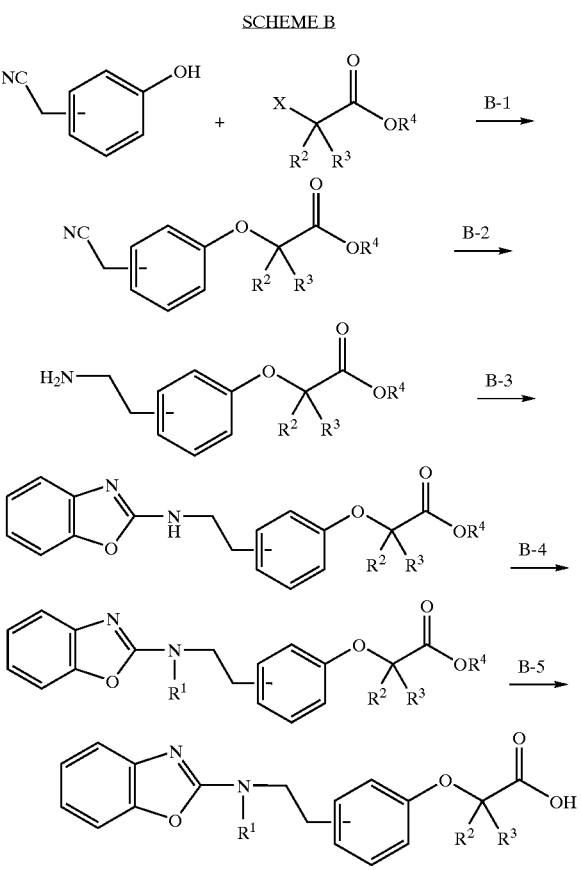

The first step is achieved as follows. A phenol compound is dissolved in a solvent such as dimethylformamide, tetrahydrofuran (THF), dioxane, or acetonitrile. A necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine is added thereto. Further, a necessary amount of a 2-haloalkylcarboxylic acid ester such as 2-bromoisobutyric acid ester, 2-bromo-n-butyric acid ester, or 2-bromopropionic acid ester is added, and the resultant mixture is heated at a temperature between room temperature and around the boiling point of the solvent under stirring for several to 24 hours. The ester is appropriately selected from among tert-butyl esters, ethyl esters, methyl esters, etc.

In the second step, the aldehyde compound is dissolved in a solvent such as 1,2-dichloroethane, dimethylformamide, tetrahydrofuran, dioxane, or acetonitrile. Subsequently, necessary amounts of a suitably selected amine compound and acid such as acetic acid are added, followed by reduction with a reductant such as sodium (triacetoxy)borohydride ($NaBH(OAc)_3$). When the reaction mixture is under cooling or at room temperature for several to 24 hours (under inert gas atmosphere, if necessary), the reaction is completed.

The third step is accomplished as follows. The starting amino compound is dissolved in a solvent such as dimethylformamide, tetrahydrofuran, dioxane, or acetonitrile. 2-Halobenzoxazole such as 2-chlorobenzoxazole is added thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours (under inert gas atmosphere, if necessary).

The fourth step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or THF; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

The first step is achieved as follows. A phenol compound is dissolved in a solvent such as dimethylformamide, tetrahydrofuran (THF), dioxane, or acetonitrile. A necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine is added thereto. Further, a necessary amount of a 2-haloalkylcarboxylic acid ester such as 2-bromoisobutyric acid ester, 2-bromo-n-butyric acid ester, or 2-bromopropionic acid ester is added, and the resultant mixture is stirred at room temperature or under heating at a temperature around the boiling point of the solvent for several to 24 hours. The ester is appropriately selected from among tert-butyl esters, ethyl esters, methyl esters, etc.

In the second step, the starting cyano compound is dissolved in a solvent such as tetrahydrofuran or dioxane. Subsequently, under inert gas atmosphere, if necessary, a necessary amount of a reductant such as borane-tetrahydrofuran complex ($BH_3$.THF) is added thereto, and the reaction mixture is stirred at room temperature or under heating for several to 24 hours, to thereby complete the reaction.

The third step is accomplished as follows. The starting amino compound is dissolved in a solvent such as dimethylformamide, tetrahydrofuran, dioxane, or acetonitrile. 2-Halobenzoxazole such as 2-chlorobenzoxazole is added thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours (under inert gas atmosphere, if necessary).

The fourth step is accomplished as follows. The starting amino compound is dissolved under inert solvent such as dimethylformamide, tetrahydrofuran, dioxane, or acetonitrile. A suitably selected halogenated compound is added thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours.

The fifth step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or tetrahydrofuran; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

SCHEME C

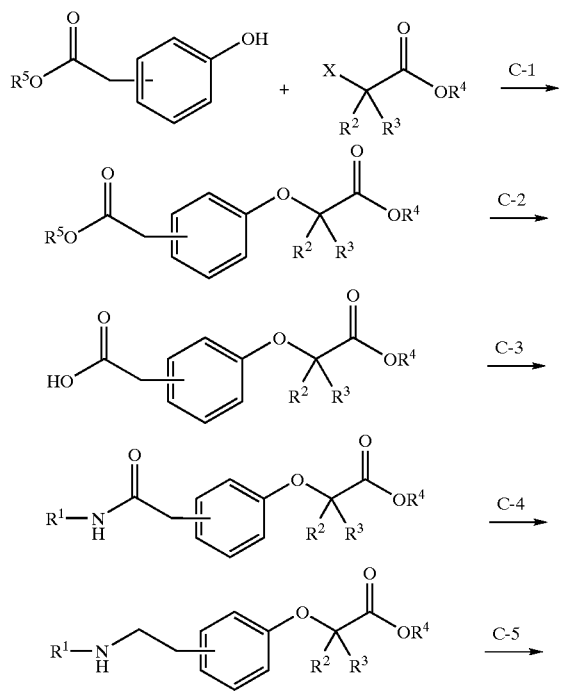

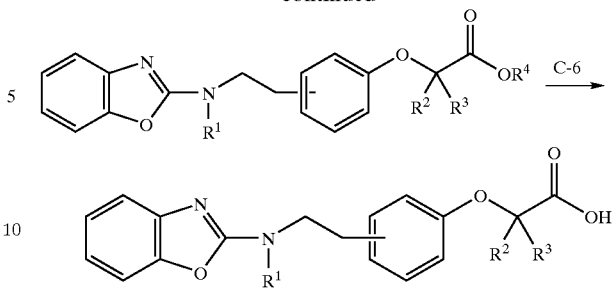

The first step is achieved as follows. A phenol compound is dissolved in a solvent such as dimethylformamide, tetrahydrofuran (THF), dioxane, or acetonitrile. A necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine is added thereto. Further, a necessary amount of a 2-haloalkylcarboxylic acid ester such as 2-bromoisobutyric acid ester, 2-bromo-n-butyric acid ester, or 2-bromopropionic acid ester is added, and the resultant mixture is stirred at room temperature or under heating at a temperature around the boiling point of the solvent for several to 24 hours. The ester is appropriately selected from among tert-butyl esters, ethyl esters, methyl esters, etc.

The second step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or THF; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

The third step is achieved as follows. The starting carboxylic acid compound is dissolved in a solvent such as dimethylformamide, tetrahydrofuran, dioxane, acetonitrile, or a mixture of solvents suitably selected therefrom. Oxalyl chloride is added thereto under cooling, and the resultant mixture is stirred at room temperature for several minutes to three hours. Subsequently, an amine, suitably selected, is added thereto under cooling, and the mixture is heated and allowed to react at a temperature between room temperature and around the boiling point of the solvent for several to 24 hours. After completion of reaction, the obtained compound is purified through a method known per se, and the resultant compound is further purified by means of, for example, chromatography, according to needs. Alternatively, the starting carboxylic acid and an amine, suitably selected, are dissolved in the above-described solvent, and a necessary amount of coupling reagent such as dicyclohexylcarbodiimide or WSC/HCl is added thereto under cooling. Further, HOBt, dimethylaminopyridine, or an analogous compound is added thereto, as needed. The resultant mixture is heated and allowed to react at a temperature between room temperature and around the boiling point of the solvent for several to 24 hours.

In the fourth step, the starting amide compound is dissolved in a solvent such as tetrahydrofuran or dioxane. Subsequently, under inert gas atmosphere, if necessary, a necessary amount of a reductant such as borane-tetrahydrofuran complex (BH$_3$.THF) is added thereto, and the reaction mixture is stirred at room temperature or under heating for several to 24 hours, to thereby complete the reaction.

The fifth step is accomplished as follows. The starting amino compound is dissolved in a solvent such as dimethylformamide, tetrahydrofuran, dioxane, or acetonitrile. 2-Halobenzoxazole such as 2-chlorobenzoxazole is added thereto in the presence of a necessary amount of an inorganic base such as K$_2$CO$_3$, Na$_2$CO$_3$, or Cs$_2$CO$_3$ or an organic base such as triethylamine or diisopropylethylamine. The mixture is heated at a temperature between room temperature and around the boiling point of the solvent under stirring for several to 24 hours (under inert gas atmosphere, if necessary).

The sixth step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or THF; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

SCHEME D

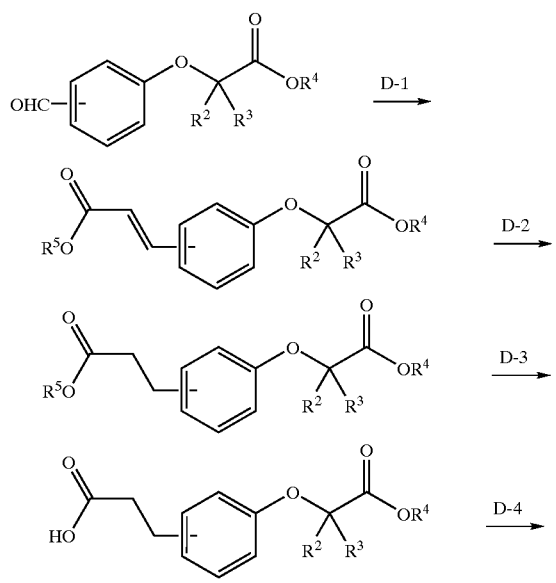

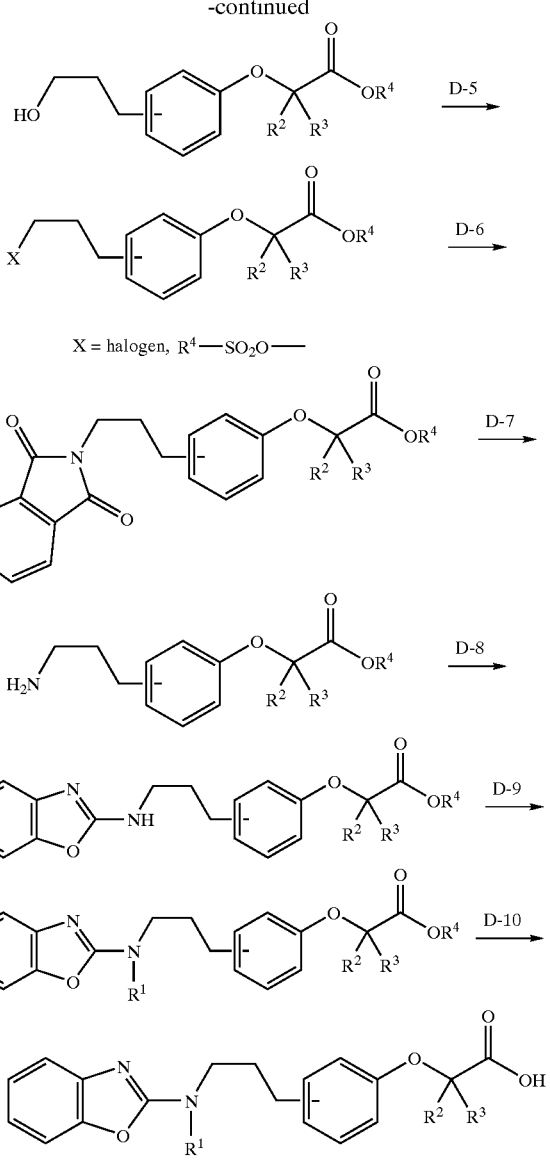

The first step is achieved as follows. A trialkylphosphonoacetate such as triethylphosphonoacetate is reacted with a base such as sodium hydride under cooling in a solvent such as tetrahydrofuran (THF) or dioxane. Subsequently, a starting aldehyde compound, which has been protected as required, is added thereto. The mixture is allowed to react for several to 24 hours at a temperature between ice-cooling and room temperature.

The second step is achieved as follows. The starting α,β-unsaturated carboxylate is dissolved in a solvent such as alcohol or an acetic acid ester. In the presence of a catalyst such as palladium-carbon, the solution is subjected to catalytic reduction in a hydrogen atmosphere or in the presence of a hydrogen-donating reagent such as formic acid.

The third step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or THF; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

The fourth step is achieved as follows. The starting carboxylic acid is dissolved in a solvent such as dimethylformamide, tetrahydrofuran, dioxane, acetonitrile, or dichloromethane. The solution is reacted with alkyl chloro carbonate such as ethyl chloro carbonate in the presence of a necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine, to thereby produce a mixed acid anhydride. Subsequently, a reductant such as sodium borohydride or an aqueous solution thereof is added thereto. The mixture is stirred for several to 24 hours at a temperature between ice-cooling and room temperature.

The fifth step is achieved as follows. In the case where an alkylsulfonate such as methanesulfonate or an arylsulfonate such as benzenesulfonate is produced, the starting alcohol compound is dissolved in a solvent such as tetrahydrofuran, dioxane, dichloromethane, or acetonitrile; alkylsulfonyl chloride (e.g., methanesulfonyl chloride), benzenesulfonyl chloride, or p-bromobenzenesulfonyl chloride is added thereto in the presence of a necessary amount of an inorganic base ($K_2CO_3$, $Na_2CO_3$, or $Cs_2CO_3$) or an organic base (triethylamine or diisopropylethylamine); and the mixture is stirred at a temperature between ice-cooling and room temperature for several to 24 hours. Alternatively, in the case where a halogenated compound is produced, the starting alcohol compound is dissolved in the above-described solvent; a necessary amount of triphenylphosphine and carbon tetrahalide are added thereto; and the mixture is stirred at a temperature between ice-cooling and room temperature for several to 24 hours.

The sixth step is achieved as follows. The starting sulfonate compound or halogen compound is dissolved in a solvent such as dimethylformamide, tetrahydrofuran, dioxane, or acetonitrile. Potassium phthalimide is added thereto, and the mixture is heated and allowed to react at a temperature between room temperature and around the boiling point of the solvent for several to 24 hours.

The seventh step is achieved as follows. The phthalimide compound is dissolved in a solvent such as ethanol, methanol, tetrahydrofuran, or dioxane. Hydrazine is added thereto, and the mixture is heated and allowed to react at a temperature between room temperature and around the boiling point of the solvent for several to 24 hours.

The eighth step is accomplished as follows. The starting amino compound is dissolved in a solvent such as dimethylformamide, tetrahydrofuran, dioxane, or acetonitrile. 2-Halobenzoxazole such as 2-chlorobenzoxazole is added thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours (under inert gas atmosphere, if necessary).

The ninth step is accomplished as follows. The starting amino compound is dissolved in an inert solvent such as dimethylformamide, tetrahydrofuran, dioxane, or acetonitrile. A suitably selected halogenated compound is added thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours.

The tenth step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or tetrahydrofuran; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

SCHEME E

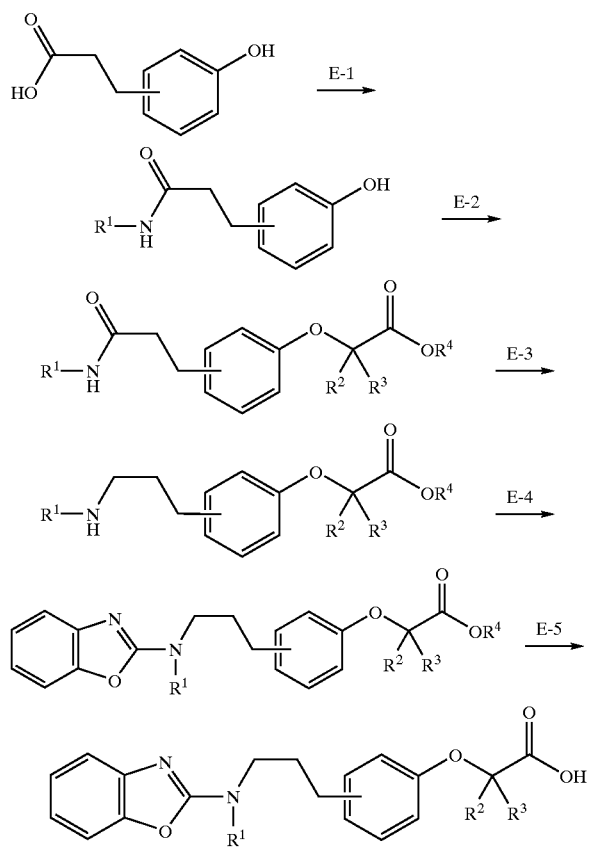

The first step is achieved as follows. A starting carboxylic acid compound is dissolved in a solvent such as dimethylformamide, tetrahydrofuran (THF), dioxane, acetonitrile, or a mixture of solvents suitably selected therefrom. Oxalyl chloride is added thereto under cooling, and the resultant mixture is stirred at room temperature for several minutes to three hours. Subsequently, an amine, suitably selected, is added thereto under cooling, and the mixture is heated and allowed to react at a temperature between room temperature and around the boiling point of the solvent for several to 24 hours. After completion of reaction, the obtained compound is purified through a method known per se, and the resultant compound is further purified by means of, for example, chromatography, according to needs. Alternatively, a starting carboxylic acid and an amine, suitably selected, are dissolved in the above-described solvent, and a necessary amount of coupling reagent such as dicyclohexylcarbodiimide or WSC/HCl is added thereto under cooling. Further, HOBt, dimethylaminopyridine, or an analogous compound is added thereto, as needed. The resultant mixture is heated and allowed to react at a temperature between room temperature and around the boiling point of the solvent for several to 24 hours.

The second step is achieved as follows. A phenol compound is dissolved in a solvent such as dimethylformamide, tetrahydrofuran, dioxane, or acetonitrile. A necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine is added thereto. Further, a necessary amount of a 2-haloalkylcarboxylic acid ester such as 2-bromoisobutyric acid ester, 2-bromo-n-butyric acid ester, or 2-bromopropionic acid ester is added, and the resultant mixture is stirred at room temperature or under heating at a temperature around the boiling point of the solvent for several to 24 hours. The ester is appropriately selected from among tert-butyl esters, ethyl esters, methyl esters, etc.

In the third step, the starting amide compound is dissolved in a solvent such as tetrahydrofuran or dioxane. Subsequently, in an inert gas atmosphere, if necessary, a necessary amount of a reductant such as borane-tetrahydrofuran complex ($BH_3 \cdot THF$) is added thereto, and the reaction mixture is stirred at room temperature or under heating for several to 24 hours, to thereby complete the reaction.

The fourth step is accomplished as follows. The starting amino compound is dissolved in a solvent such as dimethylformamide, tetrahydrofuran, dioxane, or acetonitrile. 2-Halobenzoxazole such as 2-chlorobenzoxazole is added thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours (under inert gas atmosphere, if necessary).

The fifth step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or tetrahydrofuran; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

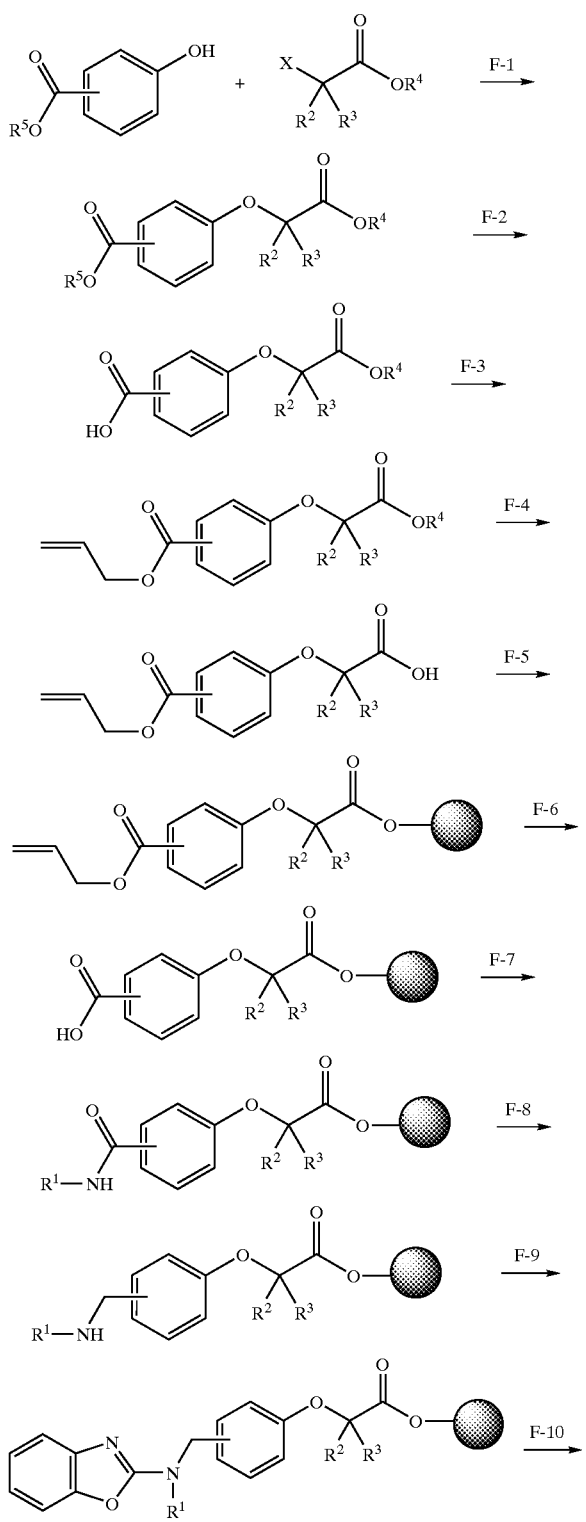

SCHEME F (Soild phase synthesis)

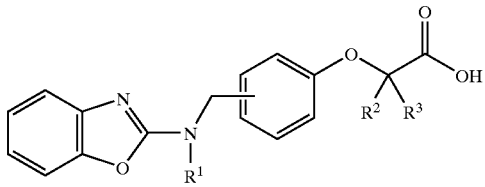

The first step is achieved as follows. A phenol compound is dissolved in a solvent such as dimethylformamide, tetrahydrofuran (THF), dioxane, or acetonitrile. A necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine is added thereto. Further, a necessary amount of a 2-haloalkylcarboxylic acid ester such as 2-bromoisobutyric acid ester, 2-bromo-n-butyric acid ester, or 2-bromopropionic acid ester is added, and the resultant mixture is stirred at room temperature or under heating at a temperature around the boiling point of the solvent for several to 24 hours. The ester is appropriately selected from among tert-butyl esters, ethyl esters, methyl esters, etc.

The second step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or tetrahydrofuran; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

The third step is accomplished as follows. The starting carboxylic acid compound is dissolved in a solvent such as dimethylformamide, tetrahydrofuran, dioxane, dichloromethane, or acetonitrile. Allyl halide such as allyl bromide or allyl iodide is added dropwise thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours.

The fourth step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or tetrahydrofuran; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

In the fifth step, the starting carboxylic acid and a necessary amount of triphenylphosphine are dissolved in a solvent such as dimethylformamide, tetrahydrofuran, dioxane, dichloromethane, or acetonitrile, and a Wang resin is added thereto. Diethyl azodicarboxylate is added thereto under ice-cooling, and the mixture is allowed to react at a temperature between ice-cooling and room temperature for several to 24 hours. After completion of reaction, the resin is collected through filtration, washed with a solvent suitably selected from among dimethylformamide, dichloromethane, methanol, diethyl ether, and analogous solvents, and dried. Subsequently, the resin is allowed to swell in a solvent such as dimethylformamide, tetrahydrofuran, dioxane, dichloromethane, or acetonitrile. An acid anhydride such as acetic anhydride is added thereto in the presence of an organic base such as triethylamine or diisopropylethylamine. The mixture is subjected to a capping reaction under ice-cooling or room temperature. After completion of reaction, the resin is collected through filtration, washed with a solvent suitably selected from among dimethylformamide, dichloromethane, methanol, diethyl ether, and analogous solvents, and dried. The reaction is preferably performed under inert gas atmosphere.

In the sixth step, a necessary amount of triphenylphosphine is dissolved in a solvent such as dimethylformamide, tetrahydrofuran, dioxane, dichloromethane, or acetonitrile, and the resin prepared in the fifth step is added thereto. Moreover, a palladium catalyst such as tetrakis(triphenylphosphine)palladium (0.1–100% equivalents) and an organic base such as piperidine are added thereto, and the mixture is allowed to react under cooling or at room temperature for several to 24 hours. The resin is collected through filtration, washed with a solvent suitably selected from among dimethylformamide, dichloromethane, methanol, diethyl ether, and analogous solvents, and dried. The reaction is preferably performed under inert gas atmosphere.

In the seventh step, the resin prepared in the sixth step is added to a solvent such as dimethylformamide, tetrahydrofuran, dioxane, dichloromethane, or acetonitrile, and then a necessary amount of HOBt, dimethylaminopyridine, or an analogous compound is added thereto. A primary amine, suitably selected, and an organic base such as triethylamine or diisopropylethylamine are added thereto, and, finally, a coupling reagent such as diisopropylcarbodiimide is added thereto. The mixture is allowed to react under ice-cooling or at room temperature for several to 24 hours. After completion of reaction, the resin is collected through filtration, washed with a solvent suitably selected from among dimethylformamide, dichloromethane, methanol, diethyl ether, and analogous solvents, and dried.

In the eighth step, the resin prepared in the seventh step is reacted with a reduction agent such as borane-tetrahydrofuran complex ($BH_3$.THF) in a solvent such as tetrahydrofuran or dioxane under inert gas atmosphere. The reaction is performed at room temperature or under heating at a temperature around the boiling point of the solvent under stirring for several to 24 hours. After completion of reaction, the resin is collected through filtration, washed with a solvent suitably selected from among dimethylformamide, dichloromethane, methanol, diethyl ether, and analogous solvents, and dried.

In the ninth step, the resin prepared in the eighth step is added to a solvent such as dimethylformamide, tetrahydrofuran, dioxane, dichloromethane, or acetonitrile. Subsequently, 2-halobenzoxazole such as 2-chlorobenzoxazole is added thereto, and the mixture is stirred in the presence of an organic base such as triethylamine or diisopropylethylamine at a temperature between room temperature and around the boiling point of the solvent for several to 24 hours. After completion of reaction, the resin is collected through filtration, washed with a solvent suitably selected from among dimethylformamide, dichloromethane, methanol, diethyl ether, and analogous solvents, and dried.

The tenth step is achieved as follows. A solvent that is stable to acid such as dichloromethane or chloroform is added to the resin prepared in the ninth step, and then an acid such as trifluoroacetic acid is added thereto. The mixture is stirred under cooling or at room temperature for several to 24 hours.

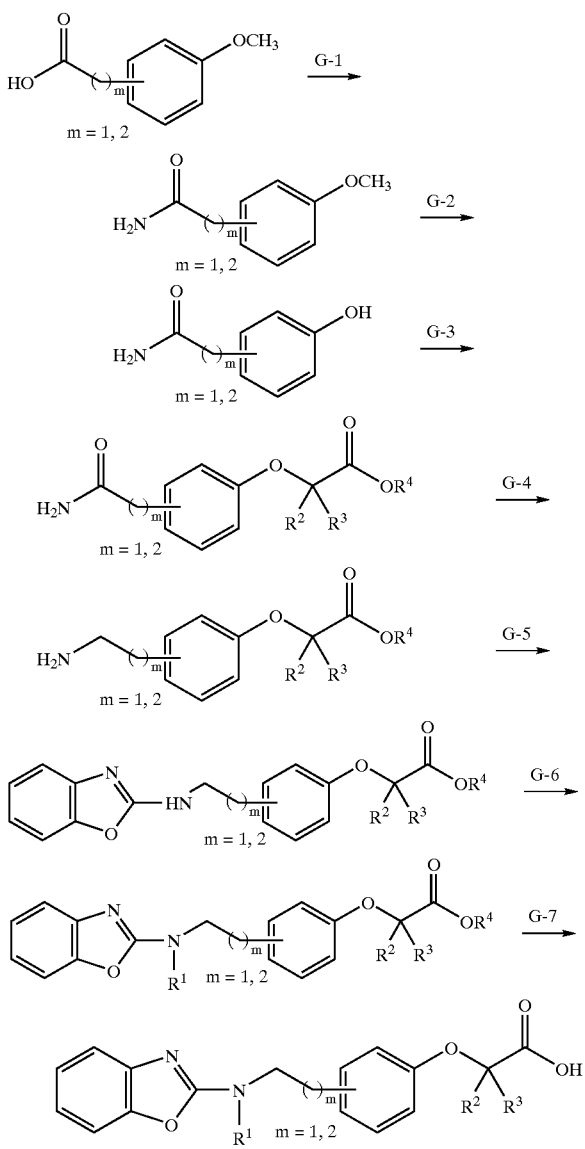

SCHEME G

The first step is achieved as follows. A starting carboxylic acid compound is dissolved in a solvent such as dimethylformamide, tetrahydrofuran (THF), dioxane, acetonitrile, or a mixture of solvents suitably selected therefrom. A necessary amount of an inorganic base (e.g., potassium carbonate ($K_2CO_3$), sodium carbonate ($Na_2CO_3$), or cesium carbonate ($Cs_2CO_3$)) or an organic base (e.g., triethylamine, diisopropylethylamine, or pyridine) is added thereto. Subsequently, an anhydride such as di-tert-butyl dicarbonate is added thereto, and the mixture is stirred under cooling or at room temperature for several minutes to three hours. Thereafter, ammonia or an ammonium salt such as ammonium hydrogencarbonate is added thereto, and the mixture is stirred under cooling or at room temperature for several to 24 hours. After completion of reaction, the obtained compound is purified through a method known per se, and the resultant compound is further purified through, for example, chromatography, as needed.

The second step is achieved as follows. The amide compound prepared in the first step is dissolved in a solvent such as dichloromethane, chloroform, or chlorobenzene, if necessary. Thereafter, a Lewis acid such as boron tribromide or aluminum chloride is added thereto, and the mixture is stirred at a temperature between under cooling and around the boiling point of the solvent for several to 24 hours.

The third step is achieved as follows. A phenol compound is dissolved in a solvent such as dimethylformamide, tetrahydrofuran, dioxane, or acetonitrile. A necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine is added thereto. Further, a necessary amount of a 2-haloalkylcarboxylic acid ester such as 2-bromoisobutyric acid ester, 2-bromo-n-butyric acid ester, or 2-bromopropionic acid ester is added, and the resultant mixture is heated at a temperature between room temperature and around the boiling point of the solvent under stirring for several to 24 hours. The ester is appropriately selected from among tert-butyl esters, ethyl esters, methyl esters, etc.

In the fourth step, the starting amide compound is dissolved in a solvent such as tetrahydrofuran or dioxane. Subsequently, under inert gas atmosphere, if necessary, a necessary amount of a reductant such as borane-tetrahydrofuran complex ($BH_3 \cdot THF$) is added thereto, and the reaction mixture is stirred at room temperature or under heating for several to 24 hours, to thereby complete the reaction.

The fifth step is accomplished as follows. The starting amino compound is dissolved in a solvent such as dimethylformamide, tetrahydrofuran, dioxane, or acetonitrile. 2-Halobenzoxazole such as 2-chlorobenzoxazole is added thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours (under inert gas atmosphere, if necessary).

The sixth step is accomplished as follows. The starting amino compound is dissolved in an inert solvent such as dimethylformamide, tetrahydrofuran, dioxane, or acetonitrile. A suitably selected halogenated compound is added thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours.

The seventh step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or tetrahydrofuran; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

SCHEME H

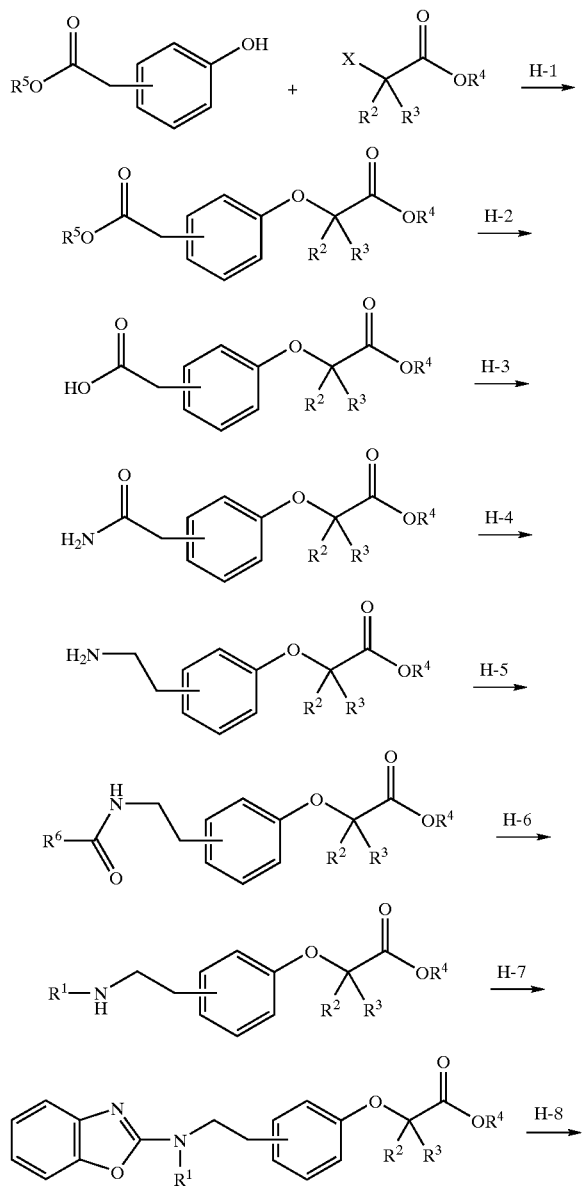

-continued

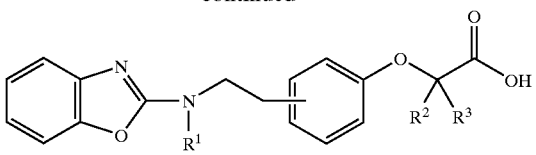

The first step is achieved as follows. A phenol compound is dissolved in a solvent such as dimethylformamide, tetrahydrofuran (THF), dioxane, or acetonitrile. A necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine is added thereto. Further, a necessary amount of a 2-haloalkylcarboxylic acid ester such as 2-bromoisobutyric acid ester, 2-bromo-n-butyric acid ester, or 2-bromopropionic acid ester is added, and the resultant mixture is heated at a temperature between room temperature and around the boiling point of the solvent under stirring for several to 24 hours. The ester is appropriately selected from among tert-butyl esters, ethyl esters, methyl esters, etc.

The second step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or tetrahydrofuran; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

The third step is achieved as follows. The starting carboxylic acid compound is dissolved in a solvent such as dimethylformamide, tetrahydrofuran, dioxane, acetonitrile, or a mixture of solvents suitably selected therefrom. A necessary amount of an inorganic base (e.g., potassium carbonate ($K_2CO_3$), sodium carbonate ($Na_2CO_3$), or cesium carbonate ($Cs_2CO_3$)) or an organic base (e.g., triethylamine, diisopropylethylamine, or pyridine) is added thereto. Subsequently, an anhydride such as di-tert-butyl dicarbonate is added thereto, and the mixture is stirred under cooling or at room temperature for several minutes to three hours. Thereafter, ammonia or an ammonium salt such as ammonium hydrogencarbonate is added thereto, and the mixture is stirred under cooling or at room temperature for several to 24 hours. After completion of reaction, the obtained compound is purified through a method known per se, and the resultant compound is further purified through, for example, chromatography, as needed.

In the fourth step, the starting amide compound is dissolved in a solvent such as tetrahydrofuran or dioxane. Subsequently, under inert gas atmosphere, if necessary, a necessary amount of a reductant such as borane-tetrahydrofuran complex ($BH_3 \cdot THF$) is added thereto, and the reaction mixture is stirred at room temperature or under heating for several to 24 hours, to thereby complete the reaction.

The fifth step is achieved as follows. The starting amino compound and a carboxylic acid, suitably selected, are dissolved in a solvent such as dimethylformamide, tetrahydrofuran, dioxane, acetonitrile, dichloromethane, chloroform, or a mixture of solvents suitably selected therefrom. A necessary amount of coupling reagent such as dicyclohexylcarbodiimide or WSC/HCl is added thereto under cooling. Further, HOBt, dimethylaminopyridine, or an analogous compound is added thereto, as needed. The resultant mixture is heated and allowed to react at a temperature between room temperature and around the boiling point of the solvent for several to 24 hours.

In the sixth step, the starting amide compound is dissolved in a solvent such as tetrahydrofuran or dioxane. Subsequently, under inert gas atmosphere, if necessary, a necessary amount of a reductant such as borane-tetrahydrofuran complex ($BH_3.THF$) is added thereto, and the reaction mixture is stirred at room temperature or under heating for several to 24 hours, to thereby complete the reaction.

The seventh step is accomplished as follows. The starting amino compound is dissolved in a solvent such as dimethylformamide, tetrahydrofuran, dioxane, or acetonitrile. 2-Halobenzoxazole such as 2-chlorobenzoxazole is added thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours (under inert gas atmosphere, if necessary).

The eighth step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or tetrahydrofuran; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

SCHEME I

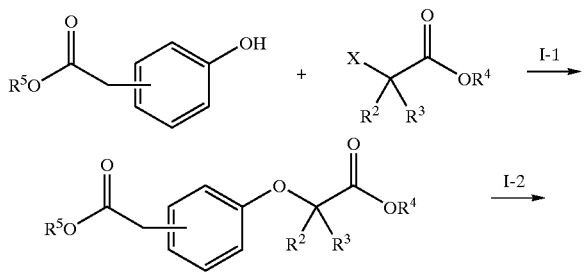

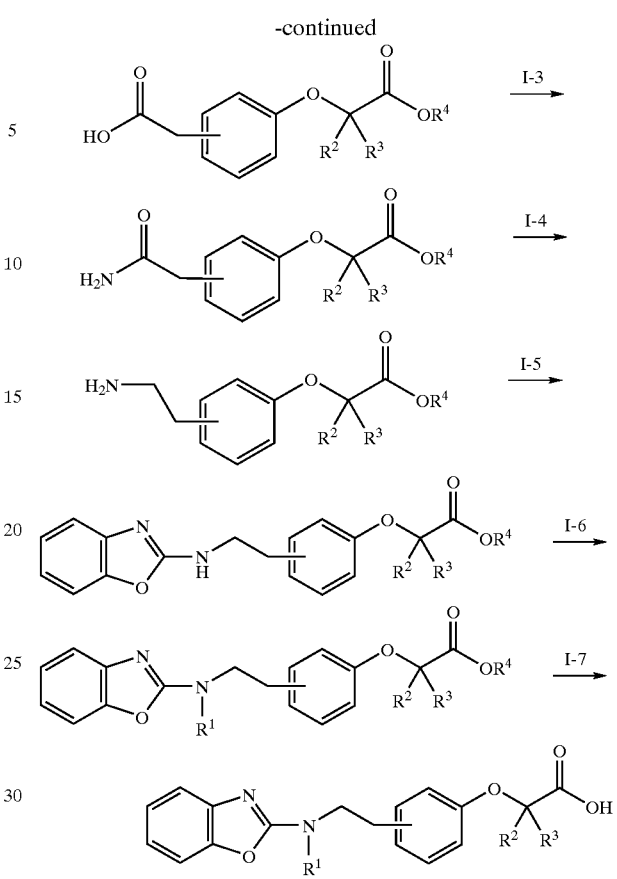

The first step is achieved as follows. A phenol compound is dissolved in a solvent such as dimethylformamide, tetrahydrofuran (THF), dioxane, or acetonitrile. A necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine is added thereto. Further, a necessary amount of a 2-haloalkylcarboxylic acid ester such as 2-bromoisobutyric acid ester, 2-bromo-n-butyric acid ester, or 2-bromopropionic acid ester is added, and the resultant mixture is stirred at room temperature or under heating at a temperature around the boiling point of the solvent for several to 24 hours. The ester is appropriately selected from among tert-butyl esters, ethyl esters, methyl esters, etc.

The second step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or tetrahydrofuran; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

The third step is achieved as follows. The starting carboxylic acid compound is dissolved in a solvent such as dimethylformamide, tetrahydrofuran, dioxane, acetonitrile, or a mixture of solvents suitably selected therefrom. A necessary amount of an inorganic base (e.g., potassium carbonate ($K_2CO_3$), sodium carbonate ($Na_2CO_3$), or cesium carbonate ($Cs_2CO_3$)) or an organic base (e.g., triethylamine, diisopropylethylamine, or pyridine) is added thereto. Subsequently, an anhydride such as di-tert-butyl dicarbonate is added thereto, and the mixture is stirred under cooling or at room temperature for several minutes to three hours. Thereafter, ammonia or an ammonium salt such as ammonium hydrogencarbonate is added thereto, and the mixture is stirred under cooling or at room temperature for several to 24 hours.

In the fourth step, the starting amide compound is dissolved in a solvent such as tetrahydrofuran or dioxane. Subsequently, under inert gas atmosphere, if necessary, a necessary amount of a reductant such as borane-tetrahydrofuran complex ($BH_3 \cdot THF$) is added thereto, and the reaction mixture is stirred at a temperature between room temperature and around the boiling point of the solvent for several to 24 hours, to thereby complete the reaction.

The fifth step is accomplished as follows. The starting amino compound is dissolved in a solvent such as dimethylformamide, tetrahydrofuran, dioxane, or acetonitrile. 2-Halobenzoxazole such as 2-chlorobenzoxazole is added thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours (under inert gas atmosphere, if necessary).

The sixth step is accomplished as follows. The starting amino compound is dissolved in an inert solvent such as dimethylformamide, tetrahydrofuran, dioxane, or acetonitrile. A suitably selected halogenated compound is added thereto in the presence of a necessary amount of an inorganic base such as $K_2CO_3$, $Na_2CO_3$, or $Cs_2CO_3$ or an organic base such as triethylamine or diisopropylethylamine. The mixture is heated at a temperature between room temperature and around the boiling point of the solvent under stirring for several to 24 hours.

The seventh step is accomplished as follows. In the case where a methyl ester, ethyl ester, or any ester that is easily hydrolyzed by an alkali is used in the first step, the resultant ester compound, serving as the starting compound of the first step, is dissolved in a solvent such as methanol, ethanol, or tetrahydrofuran; a base such as lithium hydroxide, sodium hydroxide, or potassium hydroxide, or an aqueous solution thereof is added thereto; and the mixture is allowed to react for several to 24 hours under cooling or heating at a temperature between room temperature and around the boiling point of the solvent. After reaction, the reaction mixture is acidified by use of an acid such as hydrochloric acid. On the other hand, in the case where a tert-butyl ester or any ester that is easily decomposed by an acid is used in the first step, the resultant ester compound is dissolved in a solvent which is not affected by an acid, such as dichloromethane or chloroform, then, an acid such as trifluoroacetic acid is added, and the resultant mixture is stirred for several to 24 hours under cooling or at room temperature.

The compounds according to the present invention can be produced through any of the aforementioned methods. The thus-obtained products may be purified in accordance with needs through a customary purification method such as recrystallization or column chromatography. The compounds may be converted to the aforementioned desired salts or solvates through a routine process, in accordance with needs.

As described in relation to the below-mentioned Test Example, the thus-produced compounds of the present invention exert a selective activation effect on PPARα. Thus, these compounds are usefully employed as a drug for preventing and/or treating diseases of mammals (including humans) such as hyperlipidemia, arteriosclerosis, diabetes, complications of diabetes (e.g., diabetic nephropathy), inflammation, and heart diseases, without accompanying increase in body weight or obesity.

The pharmaceutical of the present invention contains, as an active ingredient, the compound (1) or a salt thereof. No particular limitation is imposed on the form of administration, and the administration form can be appropriately determined in accordance with the purpose of treatment, and selected from among, for examples, peroral solid forms, peroral liquid forms, injections, suppositories, external preparations, ophthalmic solutions, nasal drops, ear drops, and patches. These administration forms can be produced by mixing the active ingredient with a pharmaceutically acceptable carrier and through any preparation methods known in the art.

When an oral solid drug product is prepared, the present compound (1) is mixed with a diluent (and, if necessary, an additive such as a binder, a disintegrant, a lubricant, a coloring agent, a sweetening agent, or a flavoring agent), and the resultant mixture is processed through a routine method, to thereby produce an oral solid drug product such as tablets, granules, powder, or capsules. Such an additive may be an additive generally employed in the art. Examples of the diluent include lactose, sodium chloride, glucose, starch, microcrystalline cellulose, and silicic acid; examples of the binder include water, ethanol, propanol, simple syrup, liquefied gelatin, hydroxypropyl cellulose, methyl cellulose, ethyl cellulose, shellac, calcium phosphate, and polyvinyl pyrrolidone; examples of the disintegrant include agar powder, sodium hydrogencarbonate, sodium lauryl sulfate, and monoglyceryl stearate; examples of the lubricant include purified talc, stearate salt, borax, and polyethylene glycol; examples of the coloring agent include β-carotene, yellow iron sesquioxide, and caramel; and examples of the sweetening agent include saccharose and orange peel.

When an oral liquid drug product is prepared, the present compound (1) is mixed with an additive such as a sweetening agent, a buffer, a stabilizer, or a preservative, and the resultant mixture is processed through a routine method, to thereby produce an oral liquid drug product such as solution medicine, syrup, or elixir. Such an additive may be an additive generally employed in the art. Examples of the sweetening agent include saccharose; examples of the buffer include sodium citrate; examples of the stabilizer include tragacanth; and examples of the preservative include p-hydroxybenzoate ester.

When an injection is prepared, the present compound (1) is mixed with an additive such as a pH regulator, a stabilizer, or an isotonicity agent, and the resultant mixture is processed through a routine method, to thereby produce an injection such as a subcutaneous injection, an intramuscular injection, or an intraveneous injection. Such an additive may be an additive generally employed in the art. Examples of the pH regulator include sodium phosphate; examples of the stabilizer include sodium pyrosulfite; and examples of the isotonicity agent include sodium chloride.

When a suppository is prepared, the present compound (1) is mixed with an additive such as a carrier or a surfactant, and the resultant mixture is processed through a routine method, to thereby produce a suppository. Such an additive may be an additive generally employed in the art. Examples of the carrier include polyethylene glycol and hard fat, and examples of the surfactant include polysorbate 80.

When an external drug product is prepared, the present compound (1) is mixed with an additive such as a base, a water-soluble polymer, a solvent, a surfactant, or a preservative, and the resultant mixture is processed through a routine method, to thereby produce an external preparation such as liquids and solutions, creams, gels, or ointments. Examples of the base include liquid paraffin, white Vaseline, and purified hydrous lanolin; examples of the water soluble polymer include carboxyvinyl polymer; examples of the solvent include glycerol and water; examples of the surfactant include polyoxyethylene fatty acid ester; and examples of the preservative include p-hydroxybenzoate.

When an ophthalmic solution is prepared, the present compound (1) is mixed with an additive such as a pH regulator, a stabilizer, an isotonicity agent, or a preservative, and the resultant mixture is processed through a routine method, to thereby produce an ophthalmic solution. Such an additive may be an additive generally employed in the art. Examples of the pH regulator include sodium phosphate; examples of the stabilizer include sodium pyrosulfite and EDTA; examples of the isotonicity agent include sodium chloride; and examples of the preservative include chlorobutanol.

When a nasal drop is prepared, the present compound (1) is mixed with an additive such as a pH regulator, a stabilizer, an isotonicity agent, or a preservative, and the resultant mixture is processed through a routine method, to thereby produce a nasal drop. Such an additive may be an additive generally employed in the art. Examples of the pH regulator include sodium phosphate; examples of the stabilizer include sodium pyrosulfite and EDTA; examples of the isotonicity agent include sodium chloride; and examples of the preservative include benzalkonium chloride.

When an ear drop is prepared, the present compound (1) is mixed with an additive such as a pH regulator, a buffer, a stabilizer, an isotonicity agent, or a preservative, and the resultant mixture is processed through a routine method, to thereby produce an ear drop. Such an additive may be an additive generally employed in the art. Examples of the pH regulator and the buffer include sodium phosphate; examples of the stabilizer include sodium pyrosulfite and EDTA; examples of the isotonicity agent include sodium chloride; and examples of the preservative include benzalkonium chloride.

When a patch is prepared, the present compound (1) is mixed with an additive such as a tackfier, a solvent, a cross linking agent, or a surfactant, and the resultant mixture is processed through a routine method, to thereby produce a patch such as hydrated patches or cataplasms. Such an additive may be an additive generally employed in the art. Examples of the tackfier include partially neutralized poly (acrylic acid), sodium polyacrylate, poly(2-ethylhexylacrylate), and styrene-isoprene-styrene block copolymer; examples of the solvent include glycerol and water; examples of the cross linking agent include dihydroxyaluminum aminoacetate and dried aluminum hydroxide gel; and examples of the surfactant include polyoxyethylene fatty acid ester.

The dose of the drug of the present invention differs depending on the age, body weight, and condition of the patient and the manner and frequency of administration, etc. Generally, for an adult, a dose of the present compound (1) is preferably 1 to 1,000 mg, and the drug is preferably administered perorally or parenterally once a day or several times a day in a divided manner.

EXAMPLES

The present invention will next be described in detail by way of examples, which should not be construed as limiting the invention.

Production Example 1

Synthesis of Ethyl 2-(3-Formylphenoxy)-2-methylpropionate

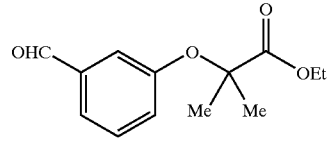

3-Hydroxybenzaldehyde (30.0 g, 0.246 mol) was dissolved in dimethylformamide (20 mL). Subsequently, potassium carbonate (51.00 g, 0.369 mol), and then ethyl 2-bromoisobutyrate (144.00 g, 0.737 mol) were added thereto, and the resultant mixture was stirred overnight at 80° C. The temperature of the reaction mixture was returned to room temperature. Ethyl acetate was added. Washing was performed sequentially with water and saturated brine, followed by drying over sodium sulfate. The reaction mixture was subjected to filtration, concentration under reduced pressure, and purification by silica gel column chromatography (n-hexane/ethyl acetate=5/1), whereby a colorless oil was obtained (57.70 g, 0.244 mol, 99.3%).

$^1$H-NMR (400 MHz, CDCl$_3$) δ: 1.25 (t, J=7 Hz, 3H), 1.56 (s, 6H), 4.21 (q, J=7 Hz, 2H), 7.14 (dd, J=8, 2 Hz, 1H), 7.32 (m, 1H), 7.41 (t, J=8 Hz, 1H), 7.49 (d, J=8 Hz, 1H), 9.94 (s, 1H).

Production Example 2

Synthesis of Ethyl 2-[3-[N-(4-Chlorobenzyl)aminomethyl]phenoxy]-2-methylpropionate

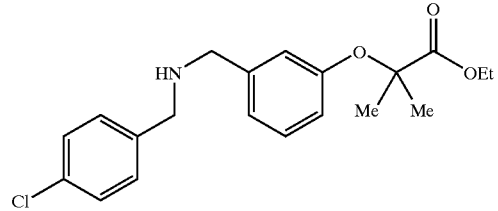

Ethyl 2-(3-formylphenoxy)-2-methylpropionate (25 g, 105.8 mmol) was dissolved in 1,2-dichloroethane (300 mL). Subsequently, 4-chlorobenzylamine (15.44 mL, 127.0 mmol) and acetic acid (7.26 mL, 127.0 mmol) were added thereto, and the resultant mixture was stirred for 20 minutes at 0° C. Subsequently, sodium (triacetoxy)borohydride [NaBH(OAc)$_3$ (26.91 g, 127.0 mmol)] was added thereto, and the mixture was stirred for five hours at room temperature. After completion of reaction, chloroform was added. Washing was performed sequentially with aqueous saturated sodium bicarbonate, water, and saturated brine, followed by drying over magnesium sulfate. The reaction mixture was subjected to filtration, concentration under reduced pressure, and purification by silica gel column chromatography (chloroform/methanol=10/1), whereby a yellow oil was obtained (35.27 g, 92%).

$^1$H-NMR (400 MHz, CDCl$_3$) δ: 1.23 (t, J=7 Hz, 3H), 1.59 (s, 6H), 3.72 (s, 2H), 3.74 (s, 2H), 4.24 (q, J=7 Hz, 2H), 6.73 (d, J=8 Hz, 1H), 6.86 (s, 1H), 6.93 (d, J=8 Hz, 1H), 7.18 (t, J=8 Hz, 1H), 7.28 (m, 4H).

Production Example 3

Synthesis of Ethyl 2-[3-[[N-(Benzoxazol-2-yl)-N-(4-chlorobenzyl)]aminomethyl]phenoxy]-2-methylpropionate

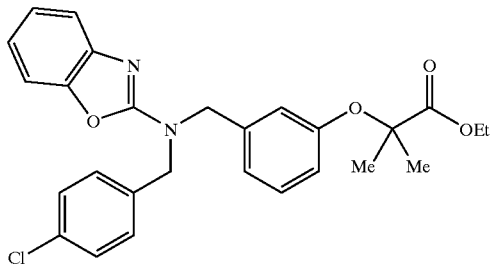

Ethyl 2-[3-[N-(4-chlorobenzyl)aminomethyl]phenoxy]-2-methylpropionate (17.22 g, 47.59 mmol) was dissolved in dimethylformamide (300 mL). Subsequently, 2-chlorobenzoxazole (7.06 mL, 61.86 mmol) and diisopropylethylamine (12.4 mL, 71.38 mmol) were added thereto, and the mixture was stirred overnight at 50° C. After completion of reaction, ethyl acetate was added. Washing was performed with water and saturated brine, followed by drying over sodium sulfate. The reaction mixture was subjected to filtration, concentration under reduced pressure, and purification by silica gel column chromatography (n-hexane/ethyl acetate=10/1), whereby a yellow oil was obtained (19.13 g, 84%).

$^1$H-NMR (400 MHz, CDCl$_3$) δ: 1.17 (t, J=7 Hz, 3H), 1.57 (s, 6H), 4.15 (q, J=7 Hz, 2H), 4.62 (s, 2H), 4.66 (s, 2H), 6.76 (m, 2H), 6.85 (d, J=8 Hz, 1H), 7.05 (t, J=8 Hz, 1H), 7.21 (m, 4H), 7.28 (m, 3H), 7.41 (d, J=8 Hz, 1H).

Example 1

Synthesis of 2-[3-[[N-(Benzoxazol-2-yl)-N-(4-chlorobenzyl)]aminomethyl]phenoxy]-2-methylpropionic Acid

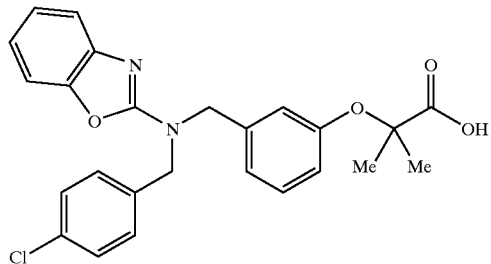

Ethyl 2-[3-[[N-(benzoxazol-2-yl)-N-(4-chlorobenzyl)] aminomethyl]phenoxy]-2-methylpropionate (2.0 g, 4.18 mmol) was dissolved in ethanol (30 mL). Subsequently, an aqueous 2M sodium hydroxide solution (30 mL) was added thereto, and the mixture was stirred for one hour at 80° C.

After completion of reaction, the reaction mixture was concentrated under reduced pressure, and the resultant concentrate was acidified with hydrochloric acid under ice-cooling. Chloroform was added for extraction. The chloroform layer was washed with water and saturated brine, followed by drying over sodium sulfate. The reaction mixture was subjected to filtration, concentration under reduced pressure, and purification by silica gel column chromatography (chloroform/methanol=10/1), whereby a colorless amorphous was obtained (1.50 g, 80%).

$^1$H-NMR (400 MHz, CDCl$_3$) δ: 1.57 (s, 6H), 4.60 (s, 2H), 4.63 (s, 2H), 6.85 (m, 2H), 6.91 (d, J=8 Hz, 1H), 7.05 (t, J=8 Hz, 1H), 7.18 (m, 4H), 7.28 (m, 3H), 7.40 (d, J=8 Hz, 1H).

Synthesis of Sodium 2-[3-[[N-(Benzoxazol-2-yl)-N-(4-chlorobenzyl)]aminomethyl]phenoxy]-2-methylpropionate

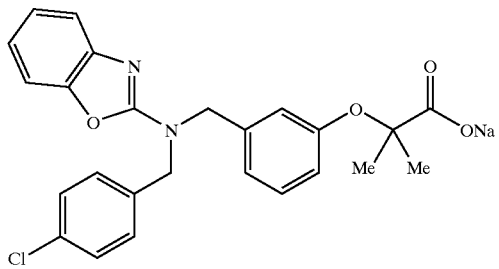

2-[3-[[N-(Benzoxazol-2-yl)-N-(4-chlorobenzyl)] aminomethyl]phenoxy]-2-methylpropionic acid (4.82 g, 10.68 mmol) was dissolved in methanol (50 mL). Subsequently, sodium methoxide (555 mg, 10.68 mmol) was added thereto, and the mixture was stirred at room temperature. After two hours, the reaction mixture was subjected to filtration and concentration under reduced pressure, whereby a yellow amorphous was obtained (4.97 g, 98%).

$^1$H-NMR (400 MHz, ) δ: 1.25 (s, 6H), 4.51 (t, 2H), 4.58 (s, 2H), 6.73 (m, 3H), 7.02 (m, 2H), 7.12 (m, 3H), 7.25 (m, 3H), 7.34 (d, J=8 Hz, 1H).

In a manner similar to that described in Example 1, the compounds of Examples 2 through Example 74 were synthesized.

Example 2

2-[3-[[N-(Benzoxazol-2-yl)-N-n-hexyl] aminomethyl]phenoxy]-2-methylpropionic Acid

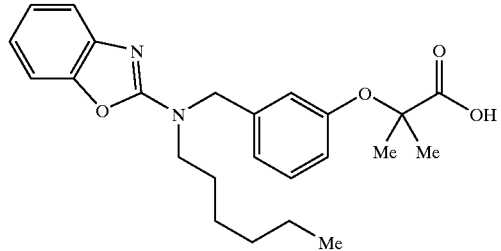

$^1$H NMR (400 MHz, CDCl$_3$) δ 0.85 (t, J=7 Hz, 3H), 1.24 (br.s, 6H), 1.57–1.60 (m, 2H), 1.58 (s, 6H), 3.41 (t, J=8 Hz, 2H), 4.65 (s, 2H), 6.83–6.85 (m, 2H), 6.90 (d, J=7 Hz, 1H), 7.01 (t, J=8 Hz, 1H), 7.13–7.19 (m, 2H), 7.24 (d, J=8 Hz, 1H), 7.36 (d, J=8 Hz, 1H).

Example 3

2-[3-([N-(Benzoxazol-2-yl)- aminomethyl]phenoxy]-2-methylpropionic Acid

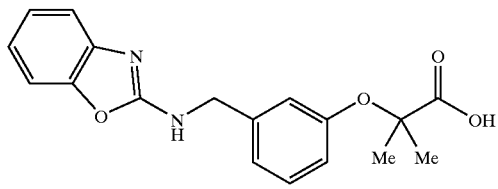

MS (m/z) 326 (M+).

Example 4

2-[3-[[N-(Benzoxazol-2-yl)-N-n-propyl]aminomethyl]phenoxy]-2-methylpropionic Acid

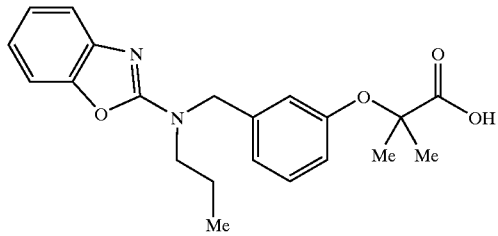

MS (m/z) 368 (M+).

Example 5

2-[3-[[N-(Benzoxazol-2-yl)-N-(4-methoxybenzyl)]aminomethyl]phenoxy]-2-methylpropionic Acid

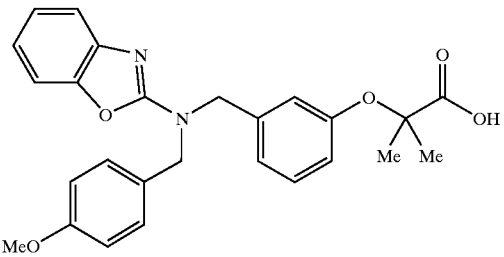

MS (m/z) 446 (M+).

Example 6

2-[3-[[N-(Benzoxazol-2-yl)-N-n-octyl]aminomethyl]phenoxy]-2-methylpropionic Acid

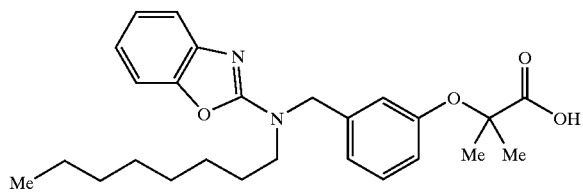

MS (m/z) 438 (M+).

Example 7

2-[3-[[N-(Benzoxazol-2-yl)-N-(4-nitrobenzyl)]aminomethyl]phenoxy]-2-methylpropionic Acid

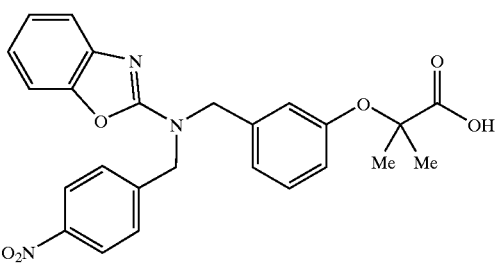

MS (m/z) 461 (M+).

Example 8

2-[3-[[N-(Benzoxazol-2-yl)-N-(4-benzyloxybenzyl)]aminomethyl]phenoxy]-2-methylpropionic Acid

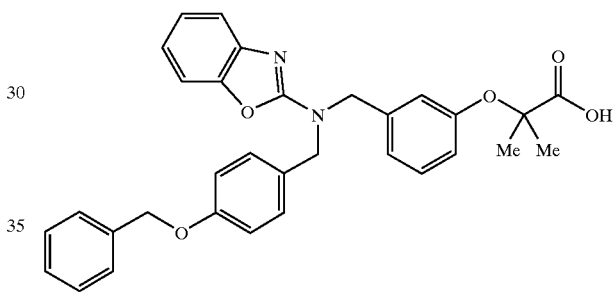

$^1$H NMR (270 MHz, CDCl$_3$) δ 1.58 (s, 6H), 4.58 (s, 2H), 4.60 (s, 2H), 5.05 (s, 2H), 6.85–6.94 (m, 5H), 7.03–7.45 (m, 12H).

Example 9

2-[4-[[N-(Benzoxazol-2-yl)-N-(4-benzyloxybenzyl)]aminomethyl]phenoxy]-2-methylpropionic Acid

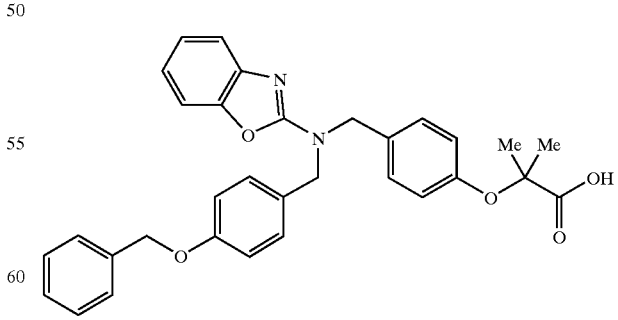

$^1$H NMR (270 MHz, CDCl$_3$) δ 1.62 (s, 6H), 4.59 (s, 2H), 4.60 (s, 2H), 5.06 (s, 2H), 6.85 (d, J=9 Hz, 2H), 6.93 (d, J=9 Hz, 2H), 7.03–7.47 (m, 13H).

Example 10

2-[4-[[N-(Benzoxazol-2-yl)-N-(4-methoxybenzyl)]aminomethyl]phenoxy]-2-methylpropionic Acid

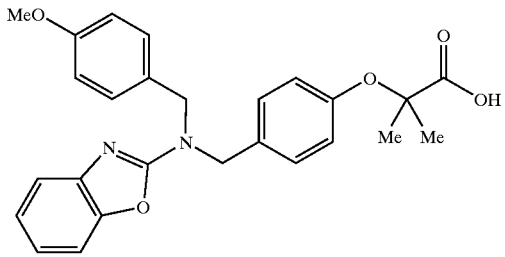

$^1$H NMR (270 MHz, CDCl$_3$) δ 1.62 (s, 6H), 3.81 (s, 3H), 4.59 (br.s, 4H), 6.84–6.87 (m, 4H), 7.03–7.30 (m, 7H), 7.47 (d, J=7 Hz, 1H).

Example 11

2-[4-[[N-(Benzoxazol-2-yl)-N-(4-nitrobenzyl)]aminomethyl]phenoxy]-2-methylpropionic Acid

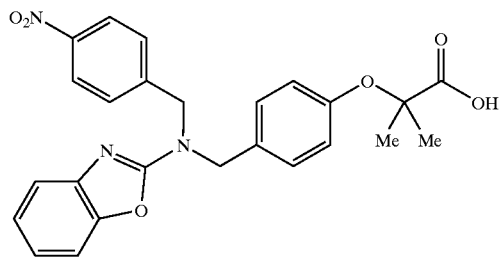

$^1$H NMR (270 MHz, CDCl$_3$) δ 1.62 (s, 6H), 4.69 (s, 2H), 4.77 (s, 2H), 6.86 (d, J=9 Hz, 2H), 7.10–7.48 (m, 8H), 8.17 (d, J=9 Hz, 2H).

Example 12

2-[4-[[N-(Benzoxazol-2-yl)-N-(naphth-1-ylmethyl)]aminomethyl]phenoxy]-2-methylpropionic Acid

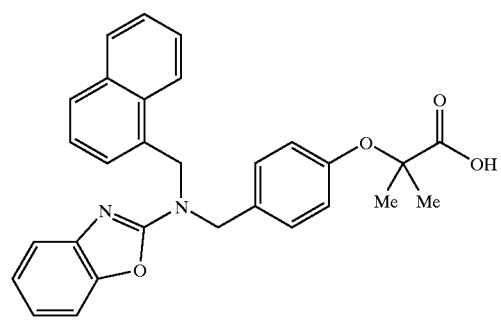

$^1$H NMR (270 MHz, CDCl$_3$) δ 1.58 (s, 6H), 4.63 (s, 2H), 5.18 (s, 2H), 6.82 (d, J=9 Hz, 2H), 7.06 (d, J=9 Hz, 2H), 7.06–7.11 (m, 1H), 7.21–7.53 (m, 7H), 7.80–7.99 (m, 3H).

Example 13

2-[4-[[N-(Benzoxazol-2-yl)-N-ethoxycarbonylmethyl]aminomethyl]phenoxy]-2-methylpropionic Acid

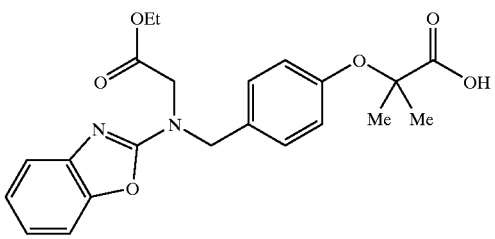

$^1$H NMR (270 MHz, CDCl$_3$) δ 1.26 (t, J=7 Hz, 3H), 1.64 (s, 6H), 4.10 (s, 2H), 4.19 (q, J=7 Hz, 2H), 4.77 (s, 2H), 6.89 (d, J=9 Hz, 2H), 7.21–7.53 (t, J=8 Hz, 1H), 7.17 (d, J=8 Hz, 2H), 7.18–7.31 (m, 2H), 7.48 (d, J=8 Hz, 1H).

Example 14

2-[4-[[N-(Benzoxazol-2-yl)-N-(2-butynyl)]aminomethyl]phenoxy)-2-methylpropionic Acid

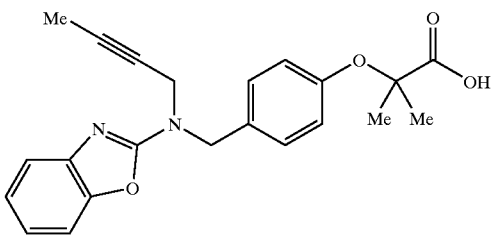

$^1$H NMR (270 MHz, CDCl$_3$) δ 1.63 (s, 6H), 1.81 (t, J=2 Hz, 3H), 4.13 (m, 2H), 4.74 (s, 2H), 6.87 (d, J=8 Hz, 2H), 7.05 (t, J=8 Hz, 1H), 7.15–7.21 (m, 3H), 7.28 (d, J=8 Hz, 1H), 7.45 (d, J=8 Hz, 1H).

Example 15

2-[4-[[N-(Benzoxazol-2-yl)-N-(5-hexenyl)]aminomethyl]phenoxy]-2-methylpropionic Acid

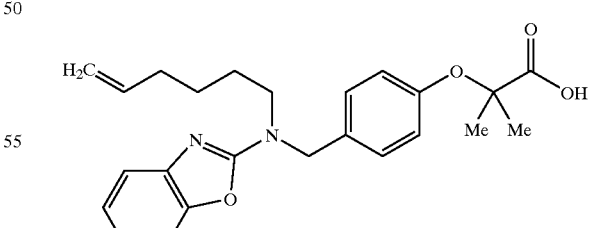

$^1$H NMR (270 MHz, CDCl$_3$) δ 1.37 (quintet, J=7 Hz, 2H), 1.55–1.68 (m, 2H), 1.62 (s, 6H), 2.03 (q, J=7 Hz, 2H), 3.39 (t, J=7 Hz, 2H), 4.66 (s, 2H), 4.92–5.01 (m, 2H), 5.67–5.82 (m, 1H), 6.85 (d, J=9 Hz, 2H), 7.02 (t, J=8 Hz, 1H), 7.11 (d, J=9 Hz, 2H), 7.16 (t, J=8 Hz, 1H), 7.25 (d, J=8 Hz, 1H), 7.46 (d, J=8 Hz, 1H).

Example 16

2-[3-[[N-(Benzoxazol-2-yl)-N-(5-hexenyl)]aminomethyl]phenoxy]-2-methylpropionic Acid

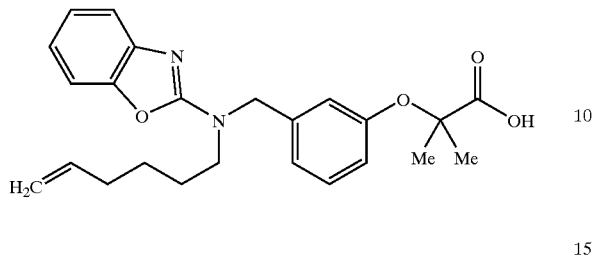

¹H NMR (270 MHz, CDCl₃) δ 1.37 (m, 2H), 1.52–1.67 (m, 2H), 1.59 (s, 6H), 2.03 (q, J=7 Hz, 2H), 3.42 (t, J=8 Hz, 2H), 4.65 (s, 2H), 4.89–5.01 (m, 2H), 5.66–5.81 (m, 1H), 6.83–6.91 (m, 3H), 7.00 (t, J=8 Hz, 1H), 7.11–7.26 (m, 3H), 7.36 (d, J=7 Hz, 1H).

Example 17

2-[3-[[N-(Benzoxazol-2-yl)-N-(2-butynyl)]aminomethyl]phenoxy]-2-methylpropionic Acid

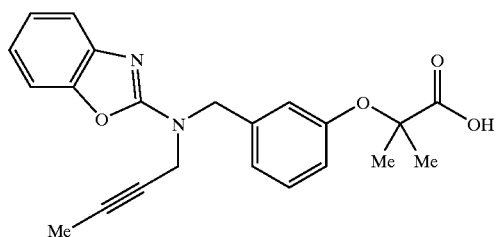

¹H NMR (270 MHz, CDCl₃) δ 1.60 (s, 6H), 1.80 (t, J=2 Hz, 3H), 4.16 (m, 2H), 4.76 (s, 2H), 6.83–6.98 (m, 3H), 7.04 (t, J=8 Hz, 1H), 7.14–7.29 (m, 3H), 7.39 (d, J=7 Hz, 1H).

Example 18

2-[3-[[N-(Benzoxazol-2-yl)-N-((2-phenylsulfonylmethyl)benzyl)]aminomethyl]phenoxy]-2-methylpropionic Acid

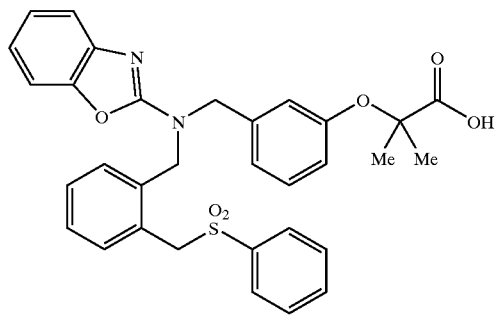

¹H NMR (270 MHz, CDCl₃) δ: 1.55 (s, 6H), 4.38 (s, 2H), 4.55 (s, 2H), 4.71 (s, 2H), 6.80–6.88 (m, 3H), 7.07 (t, J=7 Hz, 1H), 7.14–7.22 (m, 3H), 7.23–7.30 (m, 5H), 7.36 (t, J=7 Hz, 2H), 7.55 (t, J=7 Hz, 1H), 7.62 (d, J=7 Hz, 2H).

Example 19

2-[4-[[N-(Benzoxazol-2-yl)-N-((2-phenylsulfonylmethyl)benzyl)]aminomethyl]phenoxy]-2-methylpropionic Acid

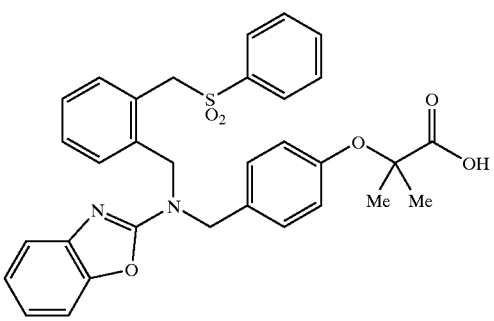

¹H NMR (270 MHz, CDCl₃) δ: 1.59 (s, 6H), 4.30 (s, 2H), 4.55 (s, 2H), 4.69 (s, 2H), 6.82 (d, J=8 Hz, 2H), 7.03–7.07 (m, 2H), 7.07–7.24 (m, 3H), 7.25–7.30 (m, 5H), 7.36 (q, J=7 Hz, 2H), 7.55 (t, J=7 Hz, 1H), 7.63 (d, J=7 Hz, 2H).

Example 20

2-[4-[[N-(Benzoxazol-2-yl)-N-cyclohexylmethyl]aminomethyl]phenoxy]-2-methylpropionic Acid

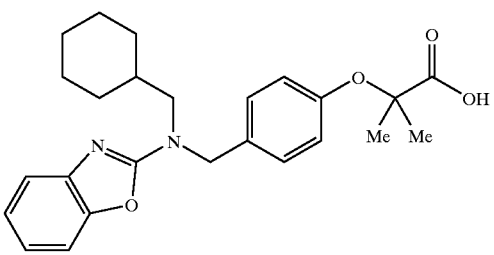

¹H NMR (270 MHz, CDCl₃) δ: 0.82–1.03 (m, 2H), 1.25–1.17 (m, 4H), 1.60 (s, 6H), 1.68 (m, 5H), 3.26 (d, J=7 Hz, 2H), 4.68 (s, 2H), 6.83 (d, J=8 Hz, 2H), 6.98–7.01 (m, 1H), 7.10 (d, J=8 Hz, 2H), 7.13–7.20 (m, 1H), 7.24 (d, J=7 Hz, 1H), 7.45 (d, J=7 Hz, 1H).

Example 21

2-[3-[[N-(Benzoxazol-2-yl)-N-n-butyl]aminomethyl]phenoxy]-2-methylpropionic Acid

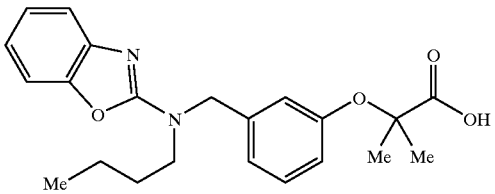

¹H NMR (270 MHz, CDCl₃) δ: 0.89 (t, J=7 Hz, 3H). 1.29 (m, 2H), 1.54 (s, 6H), 1.59–1.70 (m, 2H), 3.52 (t, J=8 Hz, 2H), 4.73 (s, 2H), 6.84 (s, 1H), 6.85–6.90 (m, 2H), 7.00–7.13 (m, 3H), 7.28 (d, J=7 Hz, 1H), 7.42 (d, J=7 Hz, 1H).

Example 22

2-[3-[[N-(Benzoxazol-2-yl)-N-(3-phenylpropyl)]aminomethyl]phenoxy]-2-methylpropionic Acid

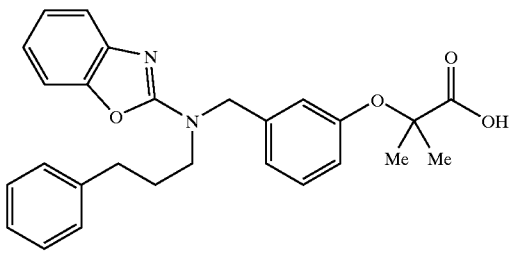

¹H NMR (270 MHz, CDCl₃) δ: 1.59 (s, 6H), 1.92 (quintet, J=8 Hz, 2H), 2.56 (t, J=8 Hz, 2H), 3.46 (t, J=8 Hz, 2H), 4.62 (s, 2H), 6.83–6.86 (m, 3H), 6.98–7.04 (m, 1H), 7.11–7.26 (m, 8H), 7. 39 (d, J=7 Hz, 1H).

Example 23

2-[3-[[N-(Benzoxazol-2-yl)-N-(3-cyclohexylpropyl)]aminomethyl]phenoxy]-2-methylpropionic Acid

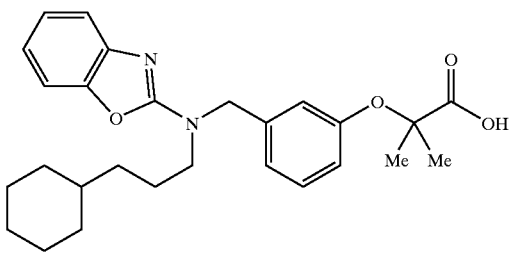

¹H NMR (270 MHz, CDCl₃) δ: 0.70–0.90 (m, 2H), 1.10–1.25 (m, 7H), 1.58 (s, 6H), 1.59–1.75 (m, 6H), 3.42 (t, J=8 Hz, 2H), 4.68 (s, 2H), 6.83–7.00 (m, 3H), 7.19–7.00 (m, 2H), 7.23–7.26 (m, 2H), 7.38 (d, J=7 Hz, 1H).

Example 24

2-[3-[[N-(Benzoxazol-2-yl)-N-cyclopropylmethyl]aminomethyl]phenoxy]-2-methylpropionic Acid

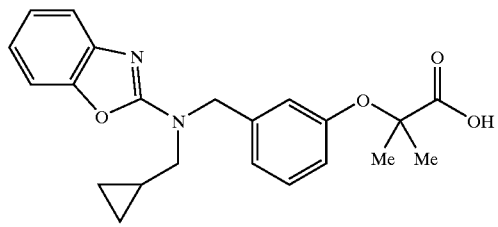

¹H NMR (270 MHz, CDCl₃) δ: 0.16–0.21 (m, 2H), 0.44–0.51 (m, 2H), 0.97–1.12 (m, 1H), 1.57 (s, 6H), 3.35 (d, J=7 Hz, 2H), 4.78 (s, 2H), 6.81–6.92 (m, 3H), 6.98–7.04 (m, 1H), 7.12–7.16 (m, 2H), 7.22–7.26 (m, 1H), 7.35 (d, J=8 Hz, 1H).

Example 25

2-[3-[[N-(Benzoxazol-2-yl)-N-cyclohexyl]aminomethyl]phenoxy]-2-methylpropionic Acid

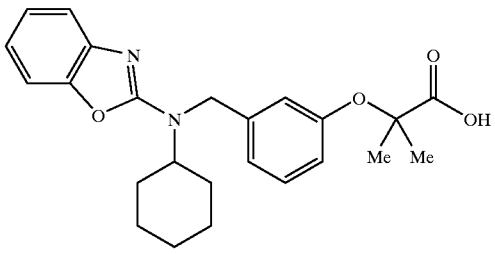

¹H NMR (270 MHz, CDCl₃) δ 0.97–1.90 (m, 10H), 1.53 (s, 6H), 4.14 (br.s, 1H), 4.68 (s, 2H), 6.81 (d, J=8 Hz, 1H), 6.94 (s, 1H), 6.93–6.99 (m, 1H), 6.99 (ddd, J=8, 8, 1 Hz, 1H), 7.13–7.25 (m, 2H), 7.14 (ddd, J=8, 8, 1 Hz, 1H), 7.36 (d, J=8 Hz, 1H).

Example 26

2-[3-[[N-(Benzoxazol-2-yl)-N-(2-nitrobenzyl)]aminomethyl]phenoxy]-2-methylpropionic Acid

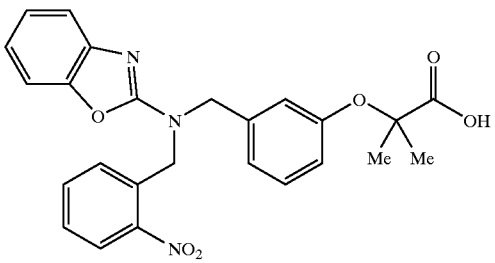

¹H NMR (270 MHz, CDCl₃) δ 1.56 (s, 6H), 4.75 (s, 2H), 5.11 (s, 2H), 6.82–6.92 (m, 2H), 6.95 (d, J=8 Hz, 1H), 7.03 (ddd, J=8, 8, 1 Hz, 1H), 7.10–7.30 (m, 4H), 7.35–7.49 (m, 2H), 7.57 (ddd, J=8, 8, 1 Hz, 1H), 8.10 (dd, J=8, 2 Hz, 1H).

Example 27

2-[3-[[N-(Benzoxazol-2-yl)-N-(2-methyl-3-nitrobenzyl)]aminomethyl]phenoxy]-2-maethylpropionic Acid

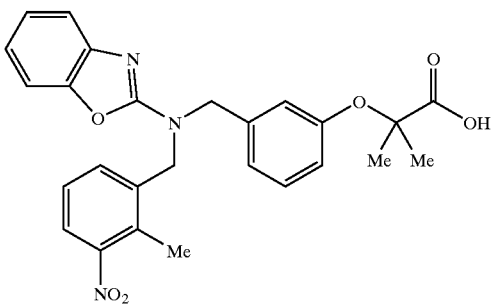

¹H NMR (270 MHz, CDCl₃) δ 1.53 (s, 6H), 2.26 (s, 3H), 4.64 (s, 2H), 4.73 (s, 2H), 6.80–6.89 (m, 3H), 7.05 (ddd, J=8, 8, 2 Hz, 1H), 7.12–7.35 (m, 6H), 7.67 (dd, J=8, 2 Hz, 1H).

Example 28

2-[3-[[N-(Benzoxazol-2-yl)-N-ethoxycarbonylmethyl]aminomethyl]phenoxy]-2-methylpropionic Acid

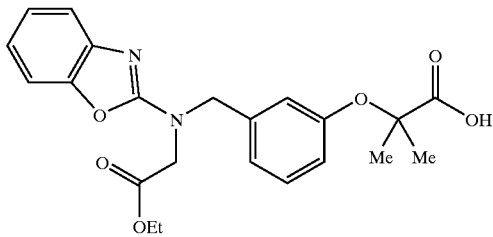

$^1$H NMR (270 MHz, CDCl$_3$) δ 1.23 (t, J=7 Hz, 3H), 1.59 (s, 6H), 4.13 (s, 2H), 4.17 (q, J=7 Hz, 2H), 4.77 (s, 2H), 6.82–6.92 (m, 2H), 6.94 (d, J=8 Hz, 1H), 7.04 (ddd, J=8, 8, 1 Hz, 1H), 7.16 (ddd, J=8, 8, 1 Hz, 1H), 7.20 (d, J=8 Hz, 1H), 7.23–7.30 (m, 1H), 7.37 (d, J=8 Hz, 1H).

Example 29

2-[4-[[N-(Benzoxazol-2-yl)-N-(2-nitrobenzyl)]aminomethyl]phenoxy]-2-methylpropionic Acid

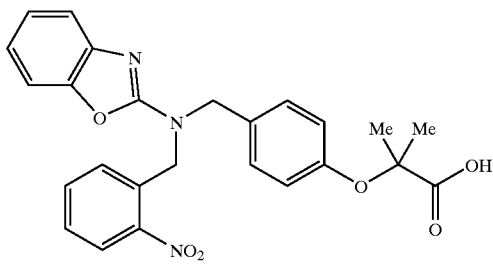

$^1$H NMR (270 MHz, CDCl$_3$) δ 1.59 (s, 6H), 4.77 (s, 2H), 5.11 (s, 2H), 6.87 (d, J=9 Hz, 2H), 7.00–7.32 (m, 4H), 7.18 (d, J=9 Hz, 2H), 7.35–7.49 (m, 2H), 7.57 (m, 1H), 8.19 (d, J=8 Hz, 1H).

Example 30

2-[4-[[N-(Benzoxazol-2-yl)-N-(2-methyl-3-nitrobenzyl)]aminomethyl]phenoxy]-2-methylpropionic Acid

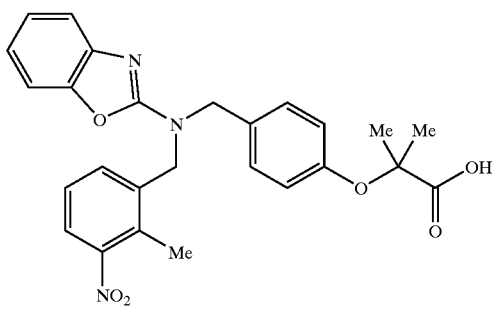

$^1$H NMR (270 MHz, CDCl$_3$) δ 1.59 (s, 6H), 2.32 (s, 3H), 4.68 (s, 2H), 4.77 (s, 2H), 6.87 (d, J=9 Hz, 2H), 7.02–7.47 (m, 6H), 7.12 (d, J=9 Hz, 2H), 7.69 (d, J=7 Hz, 1H).

Example 31

2-[2-[[N-(Benzoxazol-2-yl)-N-(2-nitrobenzyl)]aminomethyl]phenoxy]-2-methylpropionic Acid

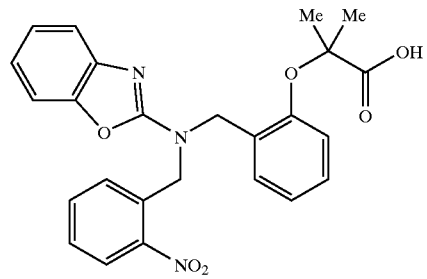

MS (m/z) 461 (M$^+$).

Example 32

2-[2-[[N-(Benzoxazol-2-yl)-N-(4-methoxybenzyl)]aminomethyl]phenoxy]-2-methylpropionic Acid

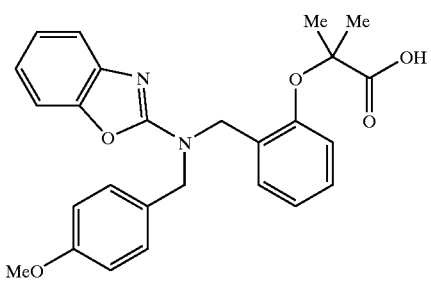

MS (m/z) 446 (M$^+$).

Example 33

2-[2-[[N-(Benzoxazol-2-yl)-N-(naphth-1-ylmethyl)]aminomethyl]phenoxy]-2-methylpropionic Acid

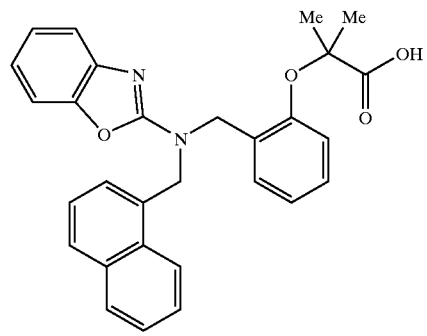

MS (m/z) 466 (M$^+$).

Example 34

2-[2-[[N-(Benzoxazol-2-yl)-N-(4-chlorobenzyl)]aminomethyl]phenoxy]-2-methylpropionic Acid

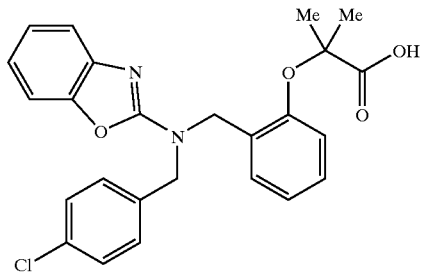

MS (m/z) 450, 452 (M+).

Example 35

2-[2-[[N-(Benzoxazol-2-yl)-N-(2-methyl-3-nitrobenzyl)]aminomethyl]phenoxy]-2-methylpropionic Acid

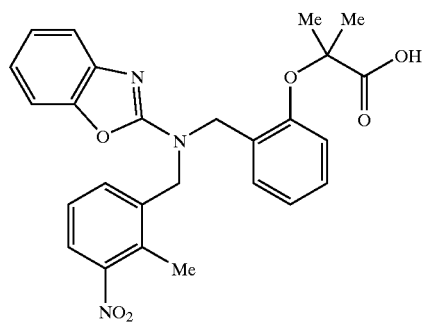

MS (m/z) 475 (M+).

Example 36

2-[2-[[N-(Benzoxazol-2-yl)-N-n-octyl]aminomethyl]phenoxy]-2-methylpropionic Acid

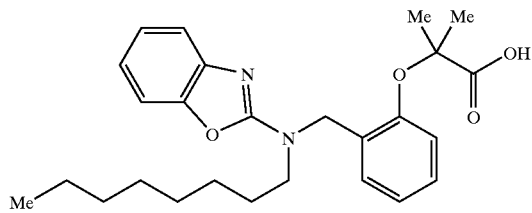

MS (m/z) 438 (M+).

Example 37

2-[3-[[N-(Benzoxazol-2-yl)-N-(2-pyridylmethyl)]aminomethyl]phenoxy]-2-methylpropionic Acid

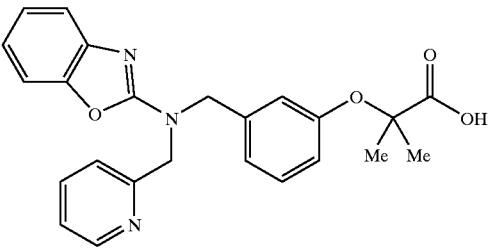

$^1$H-NMR (270 MHz, CDCl$_3$) δ 1.58 (s, 6H), 4.65 (s, 2H), 4.76 (s, 2H), 6.08 (br.s, 2H), 6.84 (br.s, 2H), 6.95–7.38 (m, 6H), 7.71 (t, J=7 Hz, 1H), 8.62 (br.s, 1H).

Example 38

2-[3-[[N-(Benzoxazol-2-yl)-N-(3-(4-chlorophenyl)propyl)]aminomethyl]phenoxy]-2-methylpropionic Acid MS (m/z) 478, 480 (M+).

Example 39

2-[3-[[N-(Benzoxazol-2-yl)-N-(4-hydroxybenzyl)]aminomethyl]phenoxy]-2-methylpropionic Acid MS (m/z) 432 (M+).

Example 40

2-[3-[[N-(Benzoxazol-2-yl)-N-(4-fluorobenzyl)]aminomethyl]phenoxy]-2-methylpropionic Acid

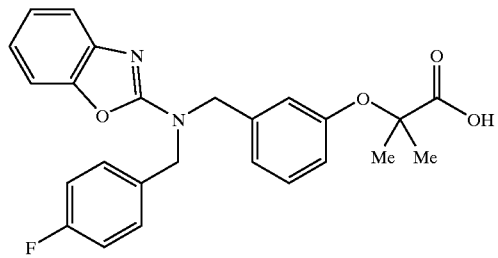

MS (m/z) 434 (M+).

Example 41

2-[3-[[N-(Benzoxazol-2-yl)-N-(4-dimethylaminobenzyl)]aminomethyl]phenoxy]-2-methylpropionic Acid

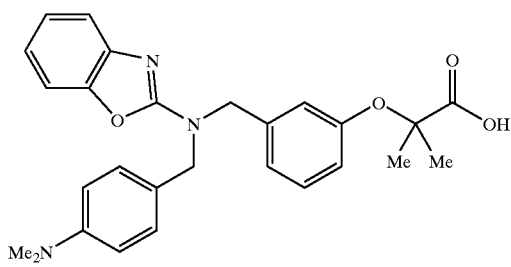

MS (m/z) 459 (M+).

Example 42

3-[[N-(Benzoxazol-2-yl)-N-(3-(4-chlorophenyl)propyl)]aminomethyl]phenoxyacetic Acid

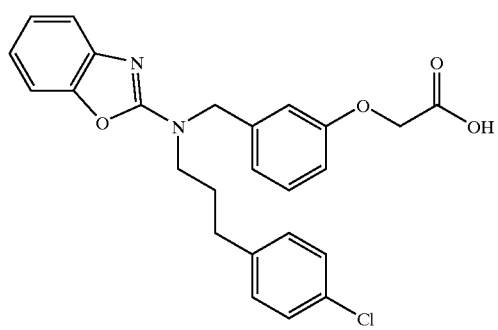

MS (m/z) 450, 452 (M+).

Example 43

3-[[N-(Benzoxazol-2-yl)-N-(4-methanesulfonyloxybenzyl)]aminomethyl]phenoxyacetic Acid

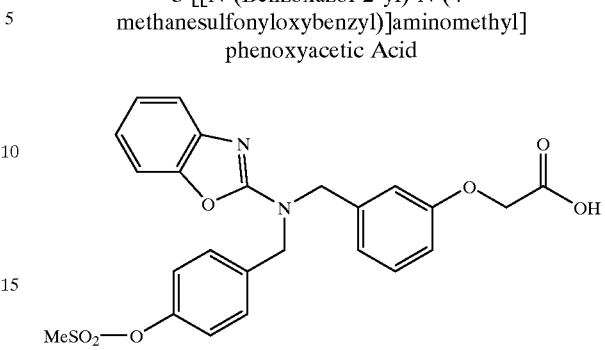

MS (m/z) 482 (M+).

Example 44

3-[[N-(Benzoxazol-2-yl)-N-(4-fluorobenzyl)]aminomethyl]phenoxyacetic Acid

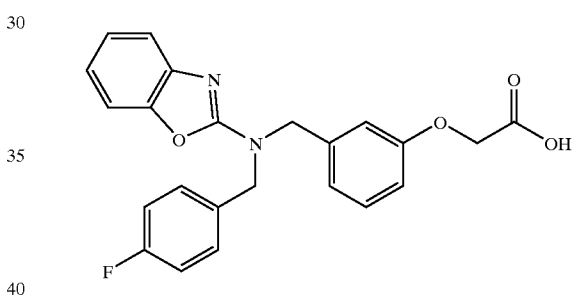

MS (m/z) 406 (M+).

Example 45

3-[[N-(Benzoxazol-2-yl)-N-(4-dimethylaminobenzyl)]aminomethyl]phenoxyacetic Acid

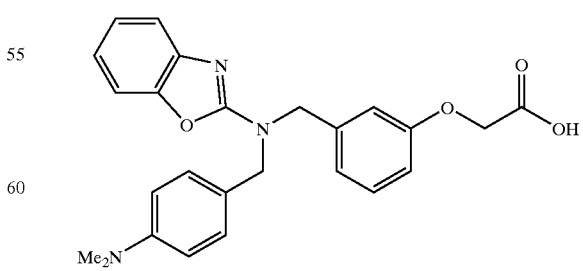

MS (m/z) 431 (M+).

Example 46

3-[[N-(Benzoxazol-2-yl)-N-n-heptyl]aminomethyl]phenoxyacetic Acid

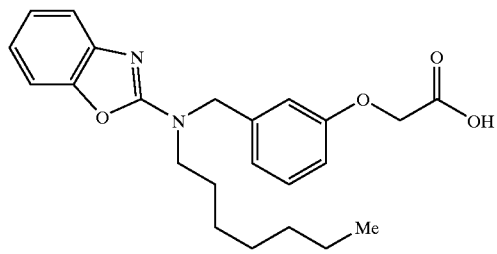

MS (m/z) 396 (M$^+$).

Example 47

3-[[N-(Benzoxazol-2-yl)-N-(4-chlorobenzyl)]aminomethyl]phenoxyacetic Acid

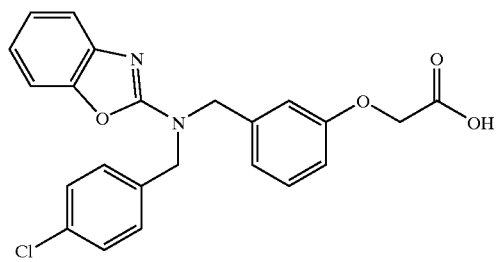

MS (m/z) 422, 424 (M$^+$).

Example 48

3-[[N-(Benzoxazol-2-yl)-N-n-octyl]aminomethyl]phenoxyacetic Acid

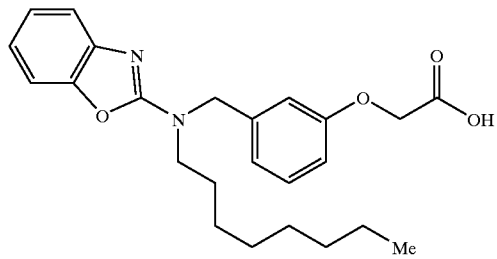

MS (m/z) 410 (M$^+$).

Example 49

3-[[N-(Benzoxazol-2-yl)-N-(3-phenylpropyl)]aminomethyl]phenoxyacetic Acid

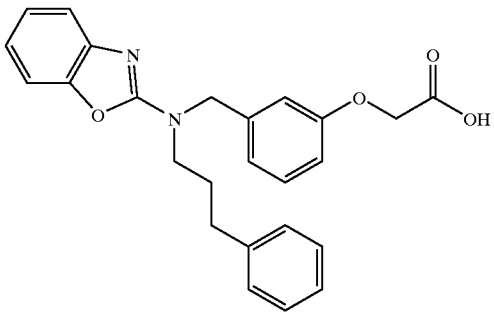

MS (m/z) 416 (m$^+$).

Example 50

3-[[N-(Benzoxazol-2-yl)-N-(4-methoxybenzyl)]aminomethyl]phenoxyacetic Acid

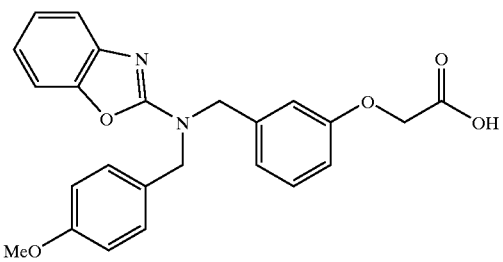

MS (m/z) 418 (M$^+$).

Example 51

3-[[N-(Benzoxazol-2-yl)-N-(naphth-1-ylmethyl)]aminomethyl]phenoxyacetic Acid

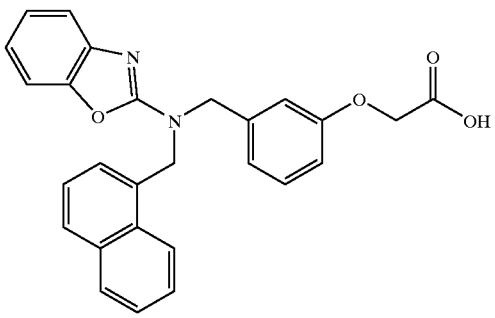

MS (m/z) 438 (M$^+$).

Example 52

3-[[N-(Benzoxazol-2-yl)-N-(2-nitrobenzyl)]aminomethyl]phenoxyacetic Acid

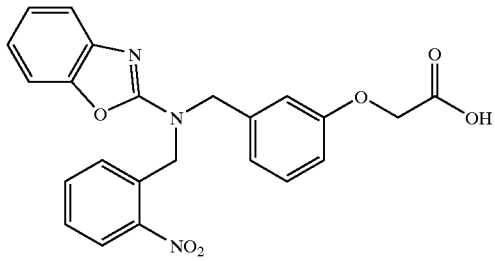

MS (m/z) 433 (M⁺).

Example 53

2-[3-[[N-(Benzoxazol-2-yl)-N-n-heptyl]aminomethyl]phenoxy]butyric Acid

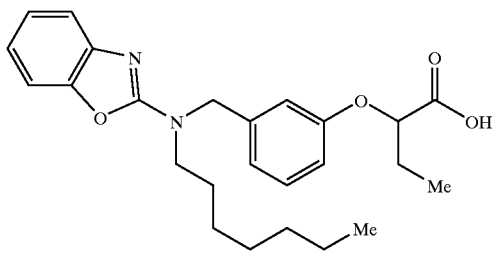

¹H NMR (270 MHz, CDCl₃) δ 0.86 (t, J=6 Hz, 3H), 1.06 (t, J=6 Hz, 3H), 1.24 (br.s, 8H), 1.50–1.70 (m, 2H), 1.85–2.10 (m, 2H), 3.30–3.50 (m, 2H), 4.52 (br.s, 1H), 4.62 (d, J=17 Hz, 1H), 4.69 (d, J=17 Hz, 1H), 6.77–6.88 (m, 3H), 6.94 (t, J=7 Hz, 1H), 7.09–7.28 (m, 3H), 7.34 (d, J=6 Hz, 1H).

Example 54

2-[3-[[N-(Benzoxazol-2-yl)-N-(4-chlorobenzyl)]aminomethyl]phenoxy]butyric Acid

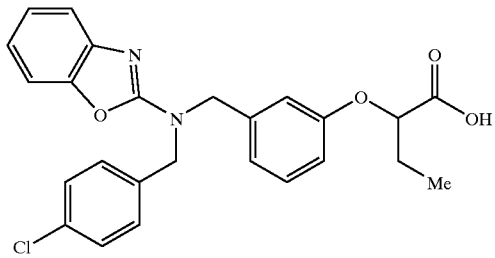

¹H NMR (270 MHz, CDCl₃) δ 1.02 (t, J=6 Hz, 3H), 1.81–2.00 (m, 2H), 4.47 (br.s, 1H), 4.58 (s, 2H), 4.66 (s, 2H), 6.75–6.83 (m, 3H), 7.03 (t, J=8 Hz, 1H), 7.10–7.20 (m, 4H), 7.23–7.30 (m, 3H), 7.36 (d, J=8 Hz, 1H).

Example 55

2-[3-[[N-(Benzoxazol-2-yl)-N-(3-phenylpropyl)]aminomethyl]phenoxy]butyric Acid

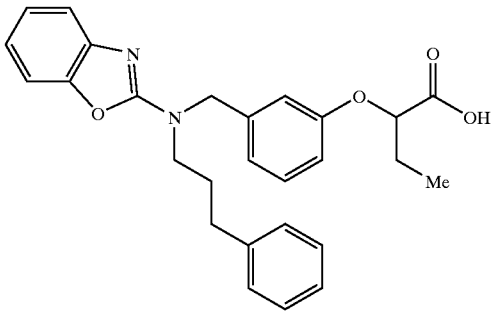

¹H NMR (270 MHz, CDCl₃) δ 1.03 (t, J=7 Hz, 3H), 1.81–2.10 (m, 4H), 2.56 (t, J=6 Hz, 2H), 3.46 (t, J=6 Hz, 2H), 4.49 (br.s, 1H), 4.58 (d, J=17 Hz, 1H), 4.65 (d, J=17 Hz, 1H), 6.70–6.95 (m, 3H), 6.99 (t, J=7 Hz, 1H), 7.07–7.32 (m, 8H), 7.35 (d, J=8 Hz, 1H).

Example 56

2-[3-[[N-(Benzoxazol-2-yl)-N-(3-(4-chlorophenyl)propyl)]aminomethyl]phenoxy]butyric Acid

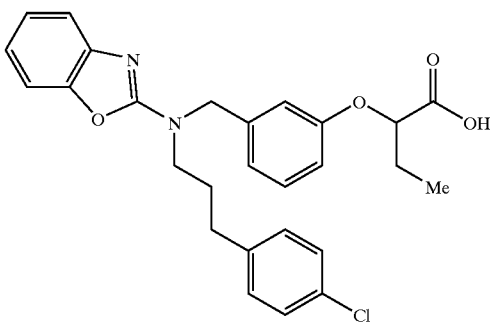

¹H NMR (270 MHz, CDCl₃) δ 1.07 (t, J=7 Hz, 3H), 1.70–2.05 (m, 4H), 2.50 (t, J=6 Hz, 2H), 3.42 (t, J=6 Hz, 2H), 4.53 (br.s, 1H), 4.58 (d, J=17 Hz, 1H), 4.63 (d, J=17 Hz, 1H), 6.73–6.83 (m, 3H), 6.93–7.03 (m, 3H), 7.03–7.38 (m, 5H), 7.34 (d, J=7 Hz, 1H).

Example 57

2-[3-[[N-(Benzoxazol-2-yl)-N-(naphth-1-ylmethyl)]aminomethyl]phenoxy]butyric Acid

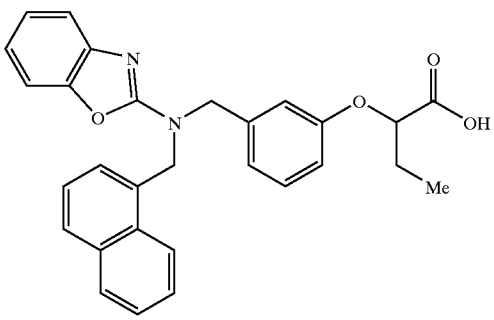

¹H NMR (270 MHz, CDCl₃) δ 0.99 (t, J=7 Hz, 3H), 1.75–2.00 (m, 2H), 4.42 (t, J=6 Hz, 1H), 4.51 (d, J=16 Hz,

1H), 4.60 (d, J=16 Hz, 1H), 5.08 (d, J=16 Hz, 1H), 5.17 (d, J=16 Hz, 1H), 6.67–6.80 (m, 3H), 6.98–7.30 (m, 6H), 7.30–7.50 (m, 3H), 7.78 (d, J=7 Hz, 1H), 7.81 (d, J=7 Hz, 1H), 7.90 (d, J=7 Hz, 1H).

Example 58

2-[3-[[N-(Benzoxazol-2-yl)-N-n-propyl]aminomethyl]phenoxy]butyric Acid

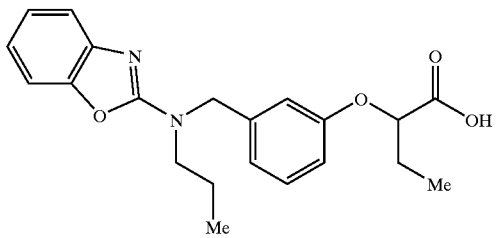

$^1$H NMR (270 MHz, CDCl$_3$) δ 0.86 (t, J=7 Hz, 3H), 1.06 (t, J=7 Hz, 3H), 1.50–1.75 (m, 2H), 1.85–2.10 (m, 2H), 3.30–3.50 (m, 2H), 4.52 (t, J=6 Hz, 1H), 4.62 (d, J=16 Hz, 1H), 4.70 (d, J=16 Hz, 1H), 6.78–6.88 (m, 3H), 6.99 (t, J=8 Hz, 1H), 7.08–7.29 (m, 3H), 7.33 (d, J=8 Hz, 1H).

Example 59

2-[3-[[N-(Benzoxazol-2-yl)-N-n-octyl]aminomethyl]phenoxy]butyric Acid

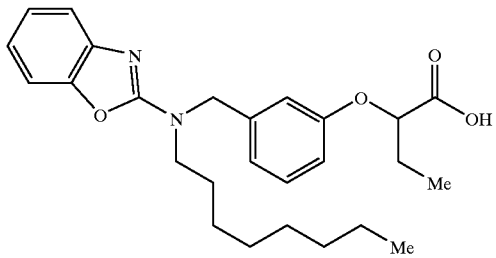

$^1$H NMR (270 MHz, CDCl$_3$) δ 0.86 (t, J=7 Hz, 3H), 1.03 (t, J=7 Hz, 3H), 1.23 (br.s, 10H), 1.60 (br.s, 2H), 1.88–2.05 (m, 2H), 3.30–3.50 (m, 2H), 4.53 (br.s, 1H), 4.66 (d, J=16 Hz, 1H), 4.71 (d, J=16 Hz, 1H), 6.77–6.87 (m, 3H), 6.93–7.04 (m, 1H), 7.06–7.26 (m, 3H), 7.32 (d, J=7 Hz, 1H).

Example 60

2-[3-[[N-(Benzoxazol-2-yl)-N-(4-fluorobenzyl)]aminomethyl]phenoxy]butyric Acid

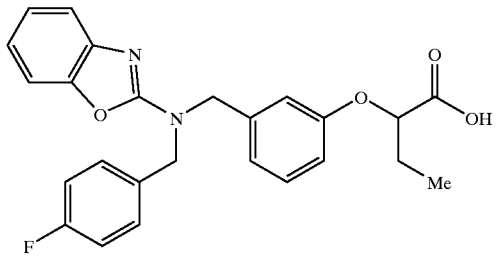

$^1$H NMR (270 MHz, CDCl$_3$) δ 1.04 (t, J=7 Hz, 3H), 1.80–2.05 (m, 2H), 4.49 (t, J=6 Hz, 1H), 4.58 (s, 2H), 4.61 (s, 2H), 6.77–6.85 (m, 3H), 6.90–7.09 (m, 4H), 7.09–7.31 (m, 4H), 7.38 (d, J=8 Hz, 1H).

Example 61

2-[3-[[N-(Benzoxazol-2-yl)-N-(4-dimethylaminobenzyl)]aminomethyl]phenoxy]butyric Acid

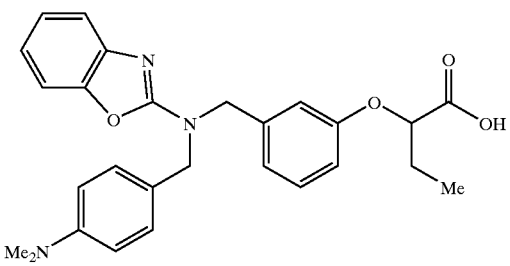

$^1$H NMR (270 MHz, CDCl$_3$) δ 1.06 (t, J=7 Hz, 3H), 1.85–2.02 (m, 2H), 2.91 (s, 6H), 4.51 (br.s, 1H), 4.57 (br.s, 4H), 6.69 (d, J=7 Hz, 2H), 6.76–6.88 (m, 3H), 7.01 (t, J=7 Hz, 1H), 7.10–7.24 (m, 4H), 7.26 (m, 1H), 7.37 (d, J=6 Hz, 1H).

Example 62

2-[3-[[N-(Benzoxazol-2-yl)-N-(3-(3-pyridyl)propyl)]aminomethyl]phenoxy]-2-methylpropionic Acid

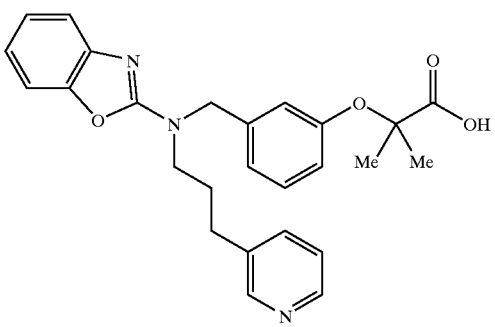

MS (m/z) 445 (M$^+$).

Example 63

2-[3-[[N-(Benzoxazol-2-yl)-N-(3-(4-chlorophenyl)propyl)]aminomethyl]phenoxy]propionic Acid

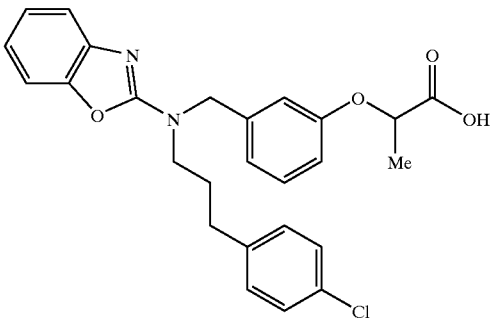

MS (m/z) 464, 466 (M$^+$).

Example 64

2-[3-[[N-(Benzoxazol-2-yl)-N-(4-(methanesulfonyloxy)benzyl)]aminomethyl]phenoxy]propionic Acid

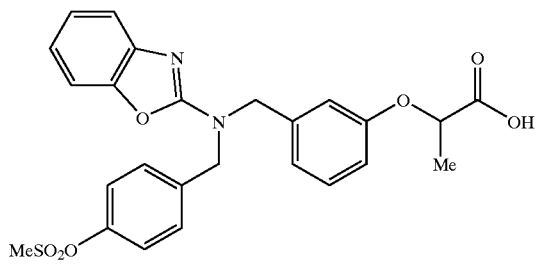

MS (m/z) 496 (m+).

Example 65

2-[3-[[N-(Benzoxazol-2-yl)-N-(4-fluorobenzyl)]aminomethyl]phenoxy]propionic Acid

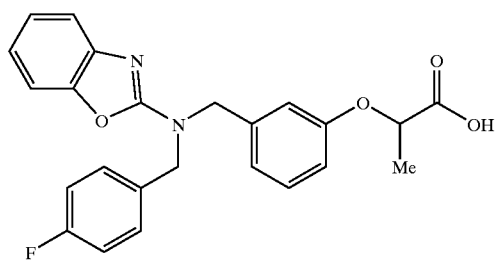

MS (m/z) 420 (M+).

Example 66

2-[3-[[N-(Benzoxazol-2-yl)-N-(4-dimethylaminobenzyl)]aminomethyl]phenoxy]propionic Acid

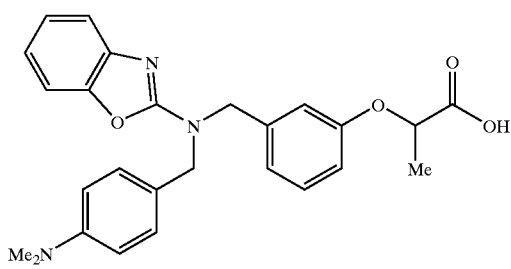

MS (m/z) 445 (M+).

Example 67

2-[3-[[N-(Benzoxazol-2-yl)-N-n-heptyl]aminomethyl]phenoxy]propionic Acid

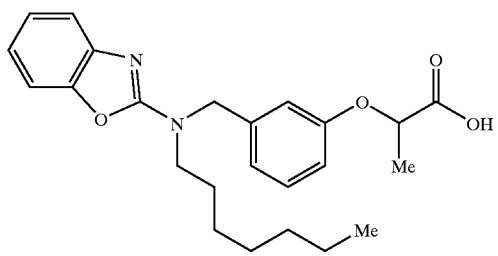

MS (m/z) 410 (M+).

Example 68

2-[3-[[N-(Benzoxazol-2-yl)-N-(4-chlorobenzyl)]aminomethyl]phenoxy]propionic Acid

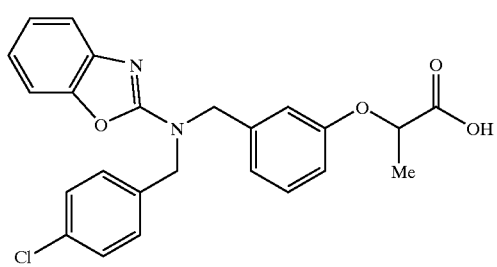

MS (m/z) 436, 438 (M+).

Example 69

2-[3-[[N-(Benzoxazol-2-yl)-N-n-octyl]aminomethyl]phenoxy]propionic Acid

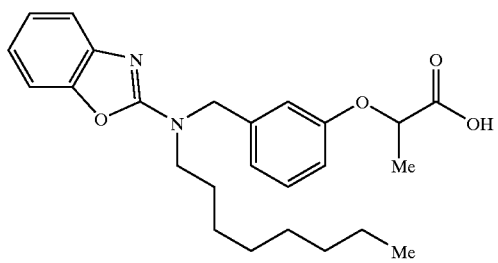

MS (m/z) 424 (M+).

Example 70

2-[3-[[N-(Benzoxazol-2-yl)-N-(3-phenylpropyl)]aminomethyl]phenoxy]propionic Acid

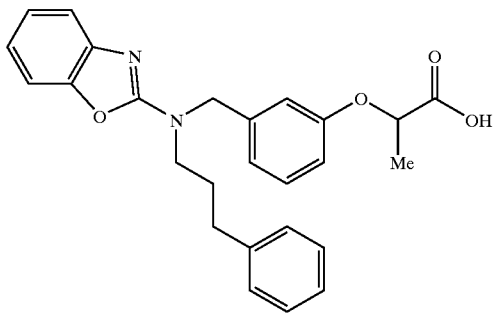

MS (M/Z) 430 (M$^+$).

Example 71

2-[3-[[N-(Benzoxazol-2-yl)-N-(4-methoxybenzyl)]aminomethyl]phenoxy]propionic Acid

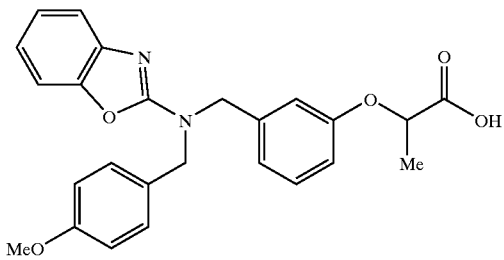

MS (m/z) 432 (M$^+$).

Example 72

2-[3-[[N-(Benzoxazol-2-yl)-N-(naphth-1-ylmethyl)]aminomethyl]phenoxy]propionic Acid

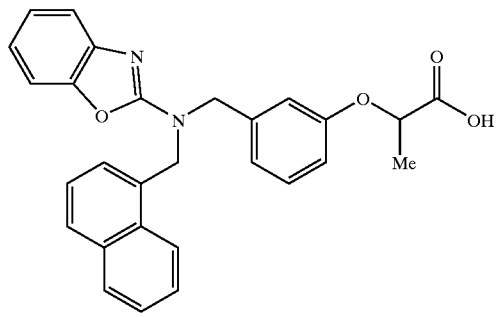

MS (m/z) 452 (M$^+$).

Example 73

2-[3-[[N-Benzoxazol-2-yl)-N-(2-nitrobenzyl)]aminomethyl]phenoxy]propionic Acid

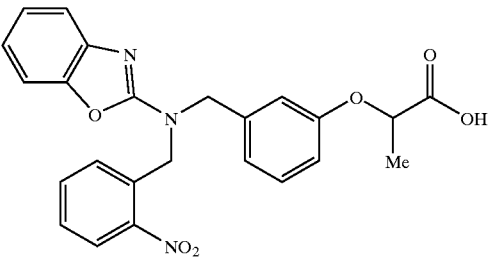

MS (m/z) 447 (M$^+$).

Example 74

2-[3-[[N-(Benzoxazol-2-yl)-N-n-propyl]aminomethyl]phenoxy]propionic Acid

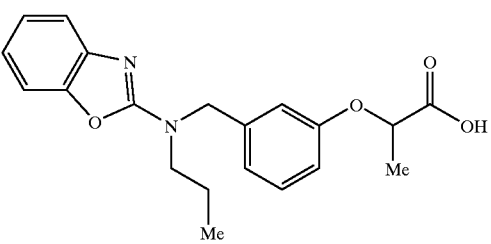

MS (m/z) 354 (M$^+$).

Production Example 4

Synthesis of tert-Butyl 2-[4-(Cyanomethyl)phenoxy]-2-methylpropionate

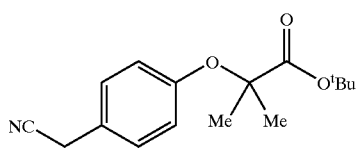

4-Hydroxyphenylacetonitrile (13.3 g, 100 mmol) and potassium carbonate (20.73 g, 150 mmol) was added to dimethylformamide (75 mL). Subsequently, tert-butyl 2-bromoisobutyrate (50.41 mL, 250 mmol) was added thereto, and the mixture was stirred for 24 hours at 80° C. The temperature of the reaction mixture was returned to room temperature, and ethyl acetate was added thereto. Washing was performed sequentially with water and saturated brine, followed by drying over sodium sulfate. The resultant mixture was subjected to concentration under reduced pressure and purification by silica gel column chromatography (n-hexane/ethyl acetate=7/1), whereby the target compound was obtained (18.62 g, 67.62 mmol, 67.6%).

Production Example 5

Synthesis of tert-Butyl 2-[4-(2-Aminoethyl)phenoxy]-2-methylpropionate

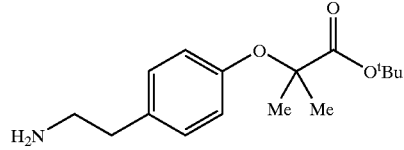

tert-Butyl 2-[(4-cyanomethyl)phenoxy]-2-methylpropionate (5.50 g, 20.0 mmol) was dissolved in tetrahydrofuran (90 mL). Subsequently, in a nitrogen atmosphere, borane-tetrahydrofuran complex in tetrahydrofuran solution [1.08M $BH_3$-THF in THF (92.6 mL, 100 mmol)] was added thereto, and the mixture was stirred for three hours at 50° C. Subsequently, 1M hydrochloric acid was gradually added at 0° C., and the resultant mixture was stirred for one hour at room temperature. Thereafter, the reaction mixture was made basic with sodium carbonate. Tetrahydrofuran was evaporated, and then chloroform was added. Washing was performed sequentially with water and saturated brine, followed by drying over sodium sulfate. The reaction mixture was subjected to concentration under reduced pressure and purification by silica gel column chromatography (chloroform/methanol=10/1), whereby the target compound was obtained (5.16 g, 13.02 mmol, 65.1%).

$^1$H NMR (400 MHz, $CDCl_3$) δ 1.44 (9H, s), 1.54 (6H, s), 2.67 (2H, t, J=7 Hz), 2.92 (2H, t, J=7 Hz), 6.86 (2H, m), 7.09 (2H, m).

Production Example 6

Synthesis of tert-Butyl 2-[4-[2-N-(Benzoxazol-2-yl)aminoethyl]phenoxy]-2-methylpropionate

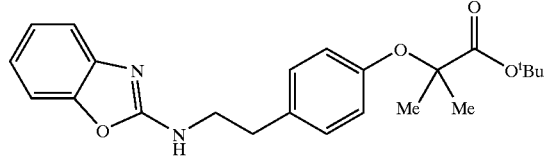

tert-Butyl 2-[4-(2-aminoethyl)phenoxy]-2-methylpropionate (290 mg, 1.04 mmol) was dissolved in tetrahydrofuran (4 mL). Subsequently, diisopropylethylamine (272 μL, 1.56 mmol), and then 2-chlorobenzoxazole (145 μL, 1.25 mmol) were added thereto, and the mixture was stirred under argon atmosphere for 15 hours at room temperature. Ethyl acetate was added to the reaction mixture. Washing was performed sequentially with water and saturated brine, followed by drying over sodium sulfate. The reaction mixture was subjected to filtration, concentration under reduced pressure, and purification by silica gel column chromatography (n-hexane/ethyl acetate=10/1), whereby the target compound was obtained (367 mg, 0.925 mmol, 88.9%).

Production Example 7

Synthesis of tert-Butyl 2-[4-[2-[N-(Benzoxazol-2-yl)-N-(5-hexenyl)]aminoethyl]phenoxy]-2-methylpropionate

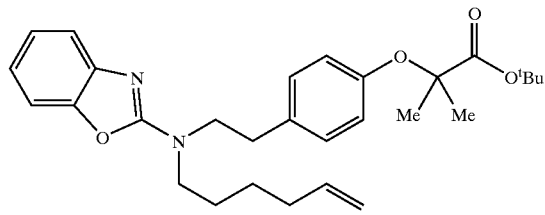

tert-Butyl 2-[4-[2-N-(benzoxazol-2-yl)aminoethyl]phenoxy]-2-methylpropionate (50 mg, 0.126 mmol) was dissolved in dimethylformamide (1 mL). Subsequently, cesium carbonate (62 mg, 0.189 mmol) and 1-bromo-5-hexene (20.2 μL, 0.151 mmol) were added thereto, and the mixture was stirred for 14 hours at 80° C. The temperature of the reaction mixture was returned to room temperature, and ethyl acetate was added. Washing was performed sequentially with water and saturated brine, followed by drying over sodium sulfate. The reaction mixture was subjected to concentration under reduced pressure and purification by silica gel column chromatography (n-hexane/ethyl acetate=10/1), whereby the target compound was obtained (41 mg, 0.0857 mmol, 68.0%).

Example 75

Synthesis of 2-[4-[2-[N-(Benzoxazol-2-yl)-N-(5-hexenyl)]aminoethyl]phenoxy]-2-methylpropionic Acid

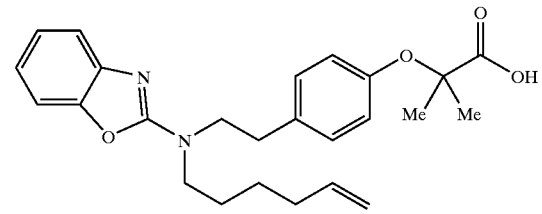

tert-Butyl 2-[4-[2-N-(benzoxazol-2-yl)aminoethyl]phenoxy]-2-methylpropionate (41 mg, 0.086 mmol) was dissolved in chloroform (3 mL). Subsequently, trifluoroacetic acid (0.5 mL) was added thereto, and the mixture was stirred for three hours at room temperature. The reaction mixture was concentrated under reduced pressure, and the resultant concentrate was subjected to toluene azeotrope. Thereafter, chloroform was added thereto. Washing was performed sequentially with water and saturated brine, followed by drying over sodium sulfate. The mixture was subjected to concentration under reduced pressure and purification by preparative TLC (silica gel, chloroform/methanol=10/1), whereby the target compound was obtained (36 mg, 0.852 mmol, 99.4%).

$^1$H NMR (400 MHz, $CDCl_3$) δ 1.37 (quintet, J=7 Hz, 2H), 1.55 (s, 6H), 1.63 (quintet, J=7 Hz, 2H), 2.07 (q, J=7 Hz, 2H), 2.88 (t, J=8 Hz, 2H), 3.40 (t, J=7 Hz, 2H), 3.69 (t, J=8 Hz, 2H), 5.01–4.94 (m, 2H), 5.81–5.70 (m, 1H), 6.86 (d, J=8 Hz, 2H), 7.02 (t, J=8 Hz, 1H), 7.09 (d, J=9 Hz, 1H), 7.22–7.14 (m, 2H), 7.25 (m, 1H), 7.42 (d, J=8 Hz, 1H).

In a manner similar to that described in Example 75, the compounds of Example 76 through Example 95 were synthesized.

Example 76

2-[4-[2-[N-(Benzoxazol-2-yl)-N-(2-butynyl)]aminoethyl]phenoxy]-2-methylpropionic Acid

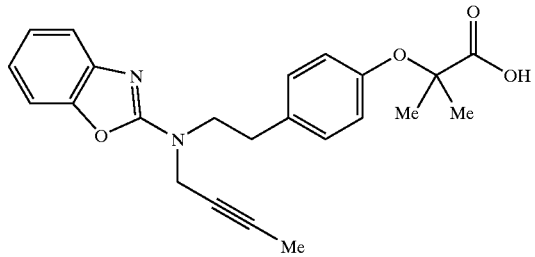

$^1$H NMR (400 MHz, CDCl$_3$) δ 1.56 (s, 6H), 1.77 (m, 3H), 2.95 (t, J=7 Hz, 2H), 3.81 (t, J=7 Hz, 2H), 4.20 (m, 2H), 6.87 (d, J=9 Hz, 2H), 7.02 (m, 1H), 7.14–7.22 (m, 3H), 7.31 (m, 1H), 7.42 (m, 1H).

Example 77

2-[4-[2-[N-(Benzoxazol-2-yl)-N-methyl]aminoethyl]phenoxy]-2-methylpropionic Acid

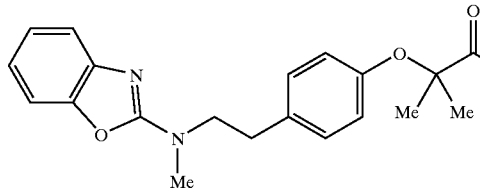

$^1$H NMR (400 MHz, CDCl$_3$) δ 1.55 (s, 6H), 2.90 (t, J=7 Hz, 2H), 3.10 (s, 3H), 3.73 (t, J=7 Hz, 2H), 6.87 (d, J=8 Hz, 2H), 7.03 (m, 1H), 7.11 (d, J=8 Hz, 2H), 7.17 (m, 1H), 7.29–7.23 (m, 1H), 7.44 (d, J=7 Hz, 1H).

Example 78

2-[4-[2-[N-(Benzoxazol-2-yl)-N-ethyl]aminoethyl]phenoxy]-2-methylpropionic Acid

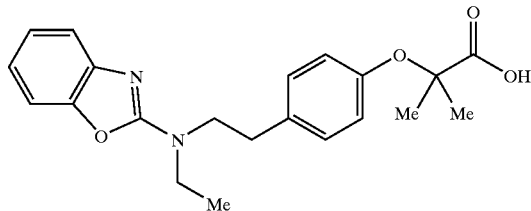

$^1$H NMR (400 MHz, CDCl$_3$) δ 1.18 (t, J=7 Hz, 3H), 1.56 (s, 6H), 2.88 (t, J=8 Hz, 2H), 3.46 (q, J=7 Hz, 2H), 3.67 (t, J=8 Hz, 2H), 6.86 (d, J=8 Hz, 2H), 6.99 (m, 1H), 7.09 (d, J=8 Hz, 2H), 7.14 (m, 1H), 7.24 (d, J=8 Hz, 1H), 7.42 (d, J=8 Hz, 1H).

Example 79

2-[4-[2-[N-(Benzoxazol-2-yl)-N-n-propyl]aminoethyl]phenoxy]-2-methylpropionic Acid

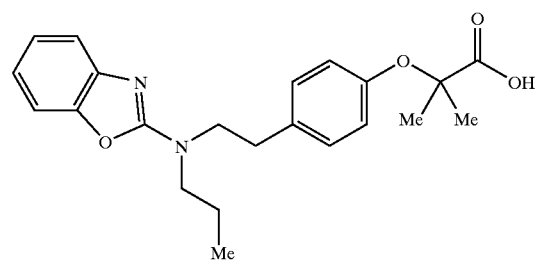

$^1$H NMR (400 MHz, CDCl$_3$) δ 0.89 (t, J=7 Hz, 3H), 1.55 (s, 6H), 1.64 (m, 2H), 2.88 (t, J=8 Hz, 2H), 3.35 (t, J=7 Hz, 2H), 3.67 (t, J=8 Hz, 2H), 6.86 (d, J=8 Hz, 2H), 6.99 (m, 1H), 7.09 (d, J=8 Hz, 2H), 7.14 (m, 1H), 7.23 (d, J=8 Hz, 1H), 7.42 (d, J=8 Hz, 1H).

Example 80

2-[4-[2-[N-(Benzoxazol-2-yl)-N-(2-nitrobenzyl)]aminoethyl]phenoxy]-2-methylpropionic Acid

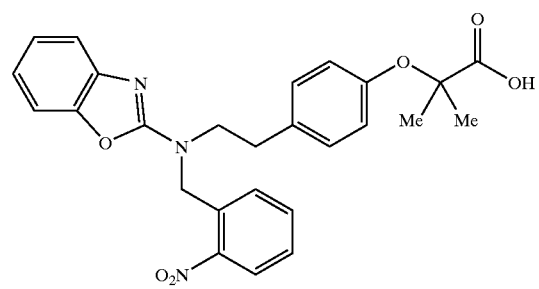

$^1$H NMR (400 MHz, CDCl$_3$) δ 1.33 (s, 6H), 2.91 (t, J=7 Hz, 2H), 3.69 (t, J=7 Hz, 2H), 4.98 (s, 2H), 6.74 (d, J=7 Hz, 2H), 6.85–7.15 (m, 3H), 7.13 (t, J=8 Hz, 1H), 7.22 (d, J=8 Hz, 1H), 7.33–7.45 (m, 3H), 7.51 (t, J=8 Hz, 1H), 8.05 (d, J=8 Hz, 1H).

Example 81

2-[4-[2-[N-(Benzoxazol-2-yl)-N-n-butyl]aminoethyl]phenoxy]-2-methylpropionic Acid

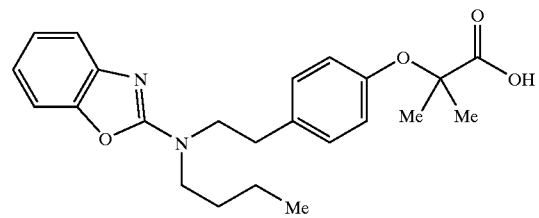

$^1$H NMR (400 MHz, CDCl$_3$) δ 0.92 (t, J=7 Hz, 3H), 1.34 (sextet, J=7 Hz, 2H), 1.54 (s, 6H), 1.60 (m, 2H), 2.91 (t, J=7 Hz, 2H), 3.41 (t, J=7 Hz, 2H), 3.72 (t, J=7 Hz, 2H), 6.86 (d, J=8 Hz, 2H), 7.05 (m, 1H), 7.10 (d, J=8 Hz, 2H), 7.18 (m, 1H), 7.26 (m, 1H), 7.47 (d, J=8 Hz, 1H).

Example 82

2-[4-[2-[N-(Benzoxazol-2-yl)-N-n-pentyl]aminoethyl]phenoxy]-2-methylpropionic Acid

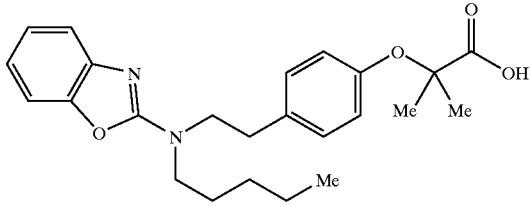

$^1$H NMR (400 MHz, CDCl$_3$) δ 0.88 (t, J=7 Hz, 3H), 1.02–1.40 (m, 4H), 1.55 (s, 6H), 1.64 (m, 2H), 2.90 (t, J=7 Hz, 2H), 3.41 (t, J=7 Hz, 2H), 3.72 (t, J=7 Hz, 2H), 6.86 (d, J=8 Hz, 2H), 7.08 (m, 3H), 7.19 (m, 1H), 7.26 (m, 1H), 7.48 (d, J=7 Hz, 1H).

Example 83

2-[4-[2-[N-(Benzoxazol-2-yl)-N-(3-methylbutyl)]aminoethyl]phenoxy]-2-methylpropionic Acid

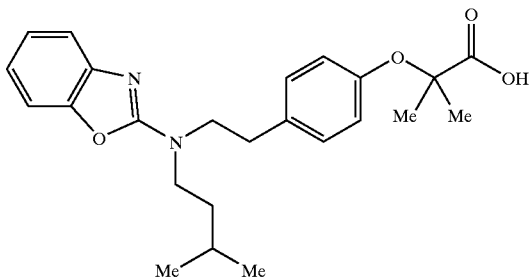

$^1$H NMR (400 MHz, CDCl$_3$) δ 0.92 (m, 6H), 1.54 (m, 9H), 2.89 (br.s, 2H), 3.41 (br.s, 2H), 3.70 (br.s, 2H), 6.86 (d, J=7 Hz, 2H), 7.09 (m, 3H), 7.17 (m, 1H), 7.26 (m, 1H), 7.46 (d, J=7 Hz, 1H).

Example 84

2-[4-[2-[N-(Benzoxazol-2-yl)-N-n-hexyl]aminoethyl]phenoxy]-2-methylpropionic Acid

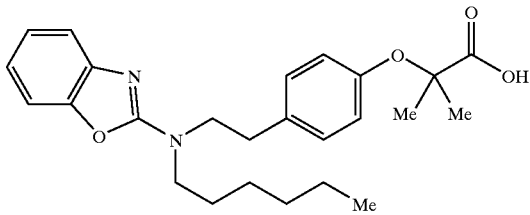

$^1$H NMR (400 MHz, CDCl$_3$) δ 0.87 (t, J=7 Hz, 3H), 1.28 (br.s, 6H), 1.56 (s, 6H), 1.60 (m, 2H), 2.88 (t, J=7 Hz, 2H), 3.39 (t, J=7 Hz, 2H), 3.68 (t, J=7 Hz, 2H), 6.86 (d, J=9 Hz, 2H), 7.01 (t, J=8 Hz, 1H), 7.09 (d, J=9 Hz, 2H), 7.15 (t, J=8 Hz, 1H), 7.24 (m, 1H), 7.44 (d, J=8 Hz, 1H).

Example 85

2-[4-[2-[N-(Benzoxazol-2-yl)-N-((2-phenylsulfonylmethyl)benzyl)]aminoethyl]phenoxy]-2-methylpropionic Acid

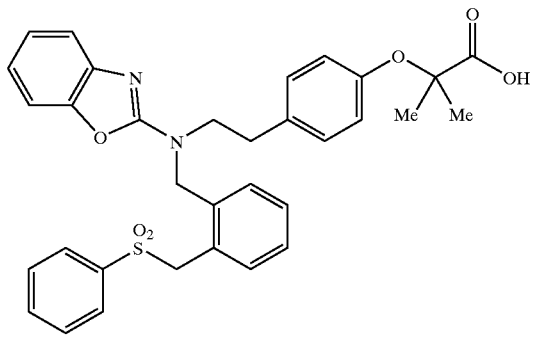

$^1$H NMR (400 MHz, CDCl$_3$) δ 1.51 (s, 6H), 2.84 (t, J=7 Hz, 2H), 3.59 (m, 2H), 4.35 (s, 2H), 4.69 (s, 2H), 7.43–6.76 (m, 12H), 7.69–7.50 (m, 4H), 7.83 (d, J=8 Hz, 1H).

Example 86

2-[4-[2-[N-(Benzoxazol-2-yl)-N-n-heptyl]aminoethyl]phenoxy]-2-methylpropionic Acid

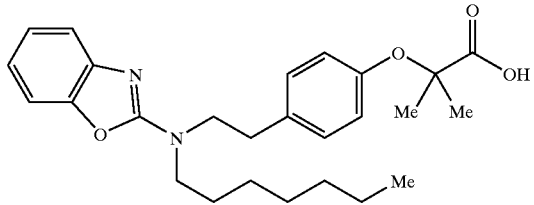

$^1$H NMR (400 MHz, CDCl$_3$) δ 0.86 (t, J=7 Hz, 3H), 1.27 (br.s, 8H), 1.55 (s, 6H), 1.60 (m, 2H), 2.87 (t, J=8 Hz, 2H), 3.38 (t, J=7 Hz, 2H), 3.67 (t, J=8 Hz, 2H), 6.86 (d, J=8 Hz, 2H), 6.99 (t, J=8 Hz, 1H), 7.09 (d, J=8 Hz, 2H), 7.14 (t, J=8 Hz, 1H), 7.23 (m, 1H), 7.42 (d, J=8 Hz, 1H).

Example 87

2-[4-[2-[N-(Benzoxazol-2-yl)-N-n-octyl]aminoethyl]phenoxy]-2-methylpropionic Acid

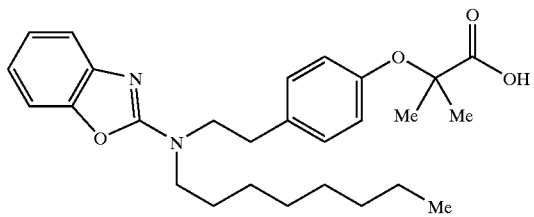

$^1$H NMR (400 MHz, CDCl$_3$) δ 0.86 (t, J=7 Hz, 3H), 1.25 (br.s, 10H), 1.57 (s, 6H), 1.60 (m, 2H), 2.88 (t, J=7 Hz, 2H), 3.39 (t, J=8 Hz, 2H), 3.68 (t, J=7 Hz, 2H), 6.86 (d, J=7 Hz, 2H), 7.00 (m, 1H), 7.09 (d, J=7 Hz, 2H), 7.15 (t, J=8 Hz, 1H), 7.24 (d, J=8 Hz, 1H), 7.43 (d, J=8 Hz, 1H).

Example 88

2-[4-[2-[N-(Benzoxazol-2-yl)-N-ethoxycarbonylmethyl]aminoethyl]phenoxy]-2-methylpropionic Acid

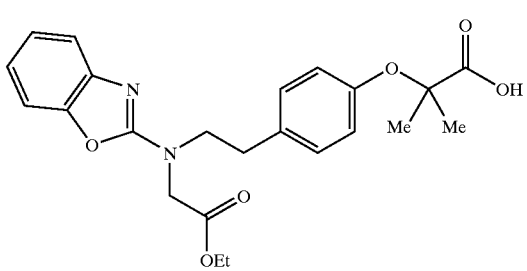

$^1$H NMR (400 MHz, CDCl$_3$) δ 1.25 (m, 3H), 1.57 (s, 6H), 2.93 (m, 2H), 3.80 (t, J=8 Hz, 2H), 4.12 (s, 2H), 4.21 (m, 2H), 6.89 (m, 2H), 7.04 (m, 1H), 7.10 (m, 2H), 7.17 (m, 1H), 7.26 (m, 1H), 7.44 (d, J=8 Hz, 1H).

Example 89

2-[4-[2-[N-(Benzoxazol-2-yl)-N-cyclopropylmethyl]aminoethyl]phenoxy]-2-methylpropionic Acid

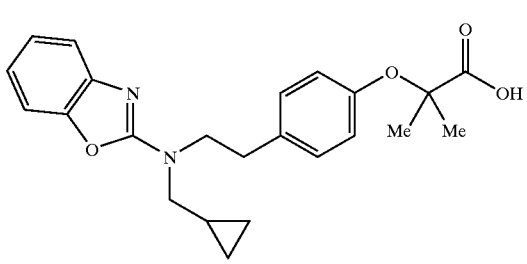

$^1$H NMR (400 MHz, CDCl$_3$) δ 0.27 (m, 2H), 0.54 (m, 2H), 1.06 (m, 1H), 1.53 (s, 6H), 2.92 (t, J=7 Hz, 2H), 3.34 (d, J=7 Hz, 2H), 3.76 (t, J=7 Hz, 2H), 6.86 (d, J=8 Hz, 2H), 6.99 (t, J=8 Hz, 1H), 7.10 (d, J=8 Hz, 2H), 7.14 (t, J=8 Hz, 1H), 7.23 (d, J=8 Hz, 1H), 7.40 (d, J=8 Hz, 1H).

Example 90

2-[4-[2-[N-(Benzoxazol-2-yl)-N-cyclohexylmethyl]aminoethyl]phenoxy]-2-methylpropionic Acid

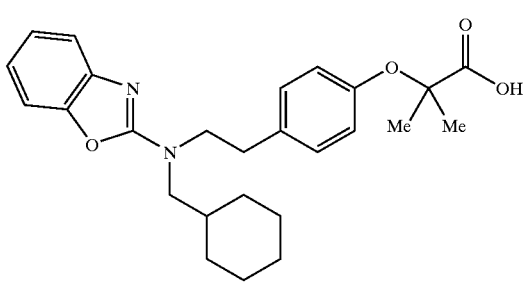

$^1$H NMR (400 MHz, CDCl$_3$) δ 0.86–1.00 (m, 2H), 1.17–1.25 (m, 4H), 1.55 (s, 6H), 1.63–1.75 (m, 5H), 2.88 (t, J=7 Hz, 2H), 3.23 (d, J=7 Hz, 2H), 3.70 (t, J=7 Hz, 2H), 6.85 (d, J=8 Hz, 2H), 6.98–7.01 (m, 1H), 7.08 (d, J=8 Hz, 2H), 7.14 (t, J=7 Hz, 1H), 7.23 (d, J=8 Hz, 1H), 7.42 (d, J=8 Hz, 1H).

Example 91

2-[4-[2-[N-(Benzoxazol-2-yl)-N-(3-phenylpropyl)]aminoethyl]phenoxy]-2-methylpropionic Acid

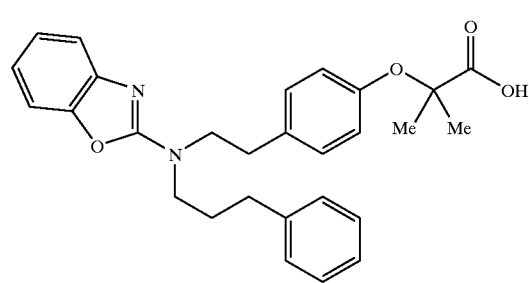

$^1$H NMR (400 MHz, CDCl$_3$) δ 1.56 (s, 6H), 1.96 (br.s, 2H), 2.63 (br.s, 2H), 2.86 (br.s, 2H), 3.44 (br.s, 2H), 3.67 (br.s, 2H), 6.80–6.90 (m, 2H), 7.00–7.52 (m, 11H).

Example 92

2-[4-[2-[N-(Benzoxazol-2-yl)-N-(4-methoxybenzyl)]aminoethyl]phenoxy]-2-methylpropionic Acid

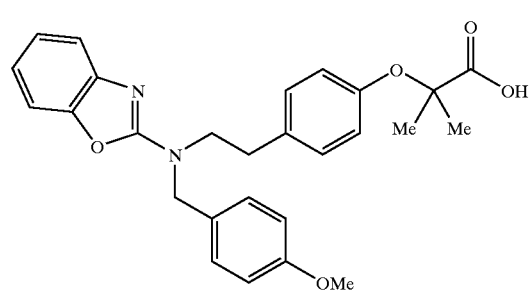

$^1$H NMR (400 MHz, CDCl$_3$) δ 1.53 (s, 6H), 2.84 (t, J=7 Hz, 2H), 3.66 (t, J=7 Hz, 2H), 3.78 (s, 3H), 4.57 (s, 2H), 6.83–6.87 (m, 4H), 7.02–7.30 (m, 7H), 7.49 (d, J=8 Hz, 1H).

Example 93

2-[4-[2-[N-(Benzoxazol-2-yl)-N-(naphth-1-ylmethyl)]aminoethyl]phenoxy]-2-methylpropionic Acid

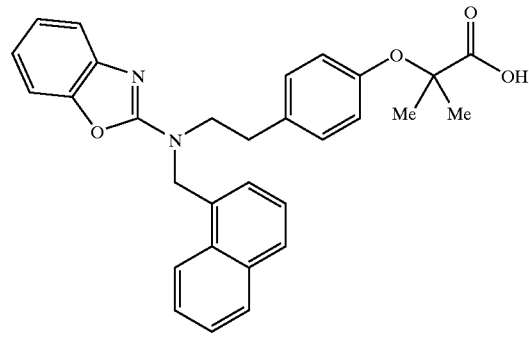

$^1$H NMR (400 MHz, CDCl$_3$) δ 1.52 (s, 6H), 2.79 (br.s, 2H), 3.61 (br.s, 2H), 5.10 (br.s, 2H), 6.80 (d, J=7 Hz, 2H), 6.93–7.05 (m, 3H), 7.06–7.29 (m, 3H), 7.47–7.62 (m, 4H), 7.80–7.92 (m, 3H).

Example 94

2-[4-[2-[N-(Benzoxazol-2-yl)-N-(4-benzyloxybenzyl)]aminoethyl]phenoxy]-2-methylpropionic Acid

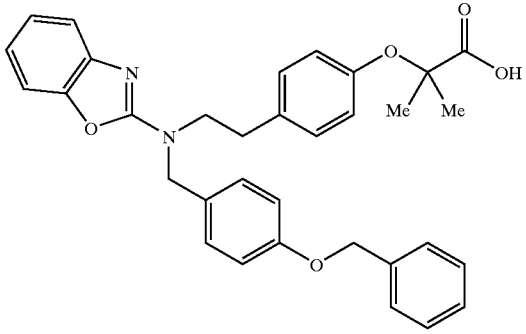

$^1$H NMR (400 MHz, CDCl$_3$) δ 1.55 (s, 6H), 2.81 (t, J=7 Hz, 2H), 3.61 (t, J=7 Hz, 2H), 4.54 (s, 2H), 4.99 (s, 2H), 6.83 (d, J=8 Hz, 2H), 6.90 (d, J=8 Hz, 2H), 7.00–7.04 (m, 3H), 7.16–7.19 (m, 3H), 7.24–7.44 (m, 7H).

Example 95

2-[4-[2-[N-(Benzoxazol-2-yl)-N-(3-cyclohexylpropyl)]aminoethyl]phenoxy]-2-methylpropionic Acid

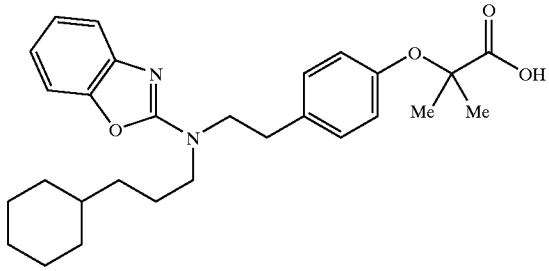

$^1$H NMR (400 MHz, CDCl$_3$) δ 0.80–0.91 (m, 2H), 1.09–1.26 (br.s, 6H), 1.52 (s, 6H), 1.55–1.70 (m, 7H), 2.90 (t, J=7 Hz, 2H), 3.38 (t, J=7 Hz, 2H), 3.75 (t, J=7 Hz, 2H), 6.76 (d, J=7 Hz, 1H), 6.77 (s, 1H), 6.89 (d, J=7 Hz, 1H), 7.07 (t, J=7 Hz, 1H), 7.16 (t, J=8 Hz, 1H), 7.19–7.22 (m, 2H), 7.42 (d, J=8 Hz, 1H).

Production Example 8

Synthesis of tert-Butyl 2-[3-(Allyloxycarbonylmethyl)phenoxy]-2-methylpropionate

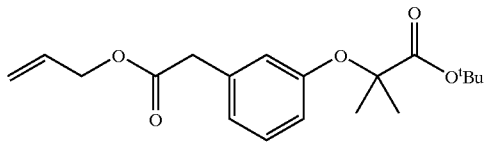

Allyl 3-hydroxyphenylacetate (2.64 g, 13.7 mmol), potassium carbonate (3.79 g, 27.4 mmol), and tert-butyl 2-bromoisobutyrate (7.65 g, 34.3 mmol) were dissolved in dimethylformamide (5 mL), and the mixture was stirred for 13 hours at 80° C. The reaction mixture was added to water, and the resultant mixture was extracted with diethyl ether. Washing was performed sequentially with water and saturated brine, followed by drying over magnesium sulfate. The mixture was subjected to concentration under reduced pressure and purification by silica gel column chromatography (n-hexane/ethyl acetate=20/1), whereby the target compound was obtained (3.47 g, 10.38 mmol, 75.7%).

$^1$H NMR (400 MHz, CDCl$_3$) δ 1.43 (s, 9H), 1.55 (s, 6H), 3.57 (s, 2H), 4.58 (m, 2H), 5.30 (m, 2H), 5.90 (m, 1H), 6.76 (m, 1H), 6.80 (m, 1H), 6.90 (d, J=7 Hz, 1H), 7.17 (m, 1H).

Production Example 9

Synthesis of 3-(1-tert-Butoxycarbonyl-1-methylethoxy)phenylacetic Acid

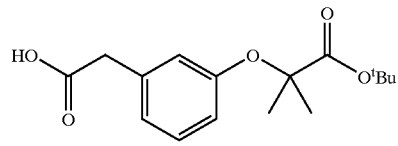

tert-Butyl 2-[3-(allyloxycarbonylmethyl)phenoxy]-2-methylpropionate (1.63 g, 4.42 mmol) was dissolved in tetrahydrofuran (40 mL). Subsequently, tetrakis(triphenylphosphine)palladium (508 mg, 0.44 mmol), triphenylphosphine (346 mg, 1.32 mmol), and piperidine (8.74 mL, 88.4 mmol) were added thereto, and the mixture was stirred for two hours at room temperature. The resultant mixture was subjected to concentration under reduced pressure and purification by silica gel column chromatography (chloroform/methanol/acetic acid=50/1/0.2), whereby the target compound was obtained (1.45 g, 4.42 mmol, q).

$^1$H NMR (270 MHz, CDCl$_3$) δ 1.42 (s, 9H), 1.57 (s, 6H), 3.58 (s, 2H), 6.76 (d, J=7 Hz, 1H), 6.79 (s, 1H), 6.88 (d, J=7 Hz, 1H), 7.19 (t, J=7 Hz, 1H).

Production Example 10

Synthesis of tert-Butyl 2-[3-(N-Cyclohexylaminocarbonylmethyl)phenoxy]-2-methylpropionate

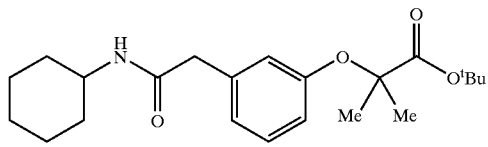

3-(1-tert-Butoxycarbonyl-1-methylethoxy)phenylacetic acid (250 mg, 0.849 mmol) was dissolved in solvent mixture of dimethylformamide (10 µL)-dichloromethane (6 mL). Subsequently, oxalyl chloride [(COCl)$_2$ (148 µL, 1.70 mmol)] was added at 0° C., the mixture was stirred for one hour at room temperature. The reaction mixture was added to a solution obtained by dissolving cyclohexylamine (0.97 mL, 8.49 mmol) in dichloromethane (1 mL) at 0° C., the mixture was stirred for one hour at room temperature. Chloroform was added to the reaction mixture. Washing was performed sequentially with 1M hydrochloric acid, water, and saturated brine, followed by drying over sodium sulfate. The mixture was subjected to concentration under reduced pressure and purification by silica gel column chromatography (chloroform/methanol=50/1), whereby the target compound was obtained (280 mg, 0.746 mmol, 87.8%).

¹H NMR (400 MHz, CDCl₃) δ 0.93–1.11 (m, 3H), 1.26–1.34 (m, 2H), 1.42 (s, 9H), 1.54 (s, 6H), 1.58–1.64 (m, 3H), 1.79 (d, J=9 Hz, 2H), 3.46 (s, 2H), 3.67–3.75 (m, 1H), 5.17 (br.s, 1H), 6.72 (s, 1H), 6.75 (dd, J=8, 3 Hz, 1H), 6.83 (d, J=8 Hz, 1H), 7.19 (t, J=8 Hz, 1H).

Production Example 11

Synthesis of tert-Butyl 2-[3-(2-N-cyclohexylaminoethyl)phenoxy]-2-methylpropionate

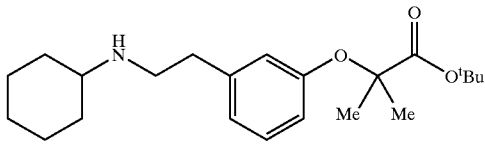

tert-Butyl 2-[3-(N-cyclohexylaminocarbonylmethyl)phenoxy]-2-methylpropionate (252 mg, 0.67 mmol) was dissolved in tetrahydrofuran (20 mL). Subsequently, in a nitrogen atmosphere, borane-tetrahydrofuran complex in tetrahydrofuran solution [1.08M BH₃-THF in THF (6.2 mL, 6.7 mmol)] was added thereto, and the mixture was stirred for 1.5 hours at 50° C. Thereafter, 1M hydrochloric acid was gradually added at 0° C. The reaction mixture was stirred for one hour at room temperature, and the resultant mixture was made basic with sodium carbonate. Tetrahydrofuran was evaporated, and chloroform was added to the mixture. Washing was performed sequentially with water and saturated brine, followed by drying over sodium sulfate. The reaction mixture was subjected to concentration under reduced pressure and purification by silica gel column chromatography (chloroform/methanol=10/1), whereby the target compound was obtained (127 mg, 0.351 mmol, 52.2%).

¹H NMR (400 MHz, CDCl₃) δ 1.05–1.25 (m, 6H), 1.41 (s, 9H), 1.52 (s, 6H), 1.85 (m, 4H), 2.42–2.47 (m, 1H), 2.74 (t, J=7 Hz, 2H), 2.86 (t, J=7 Hz, 2H), 6.65 (dd, J=8, 2 Hz, 1H), 6.69 (s, 1H), 6.78 (d, J=8 Hz, 1H), 7.10 (t, 8 Hz, 1H).

Production Example 12

Synthesis of tert-Butyl 2-[3-[2-[N-(Benzoxazol-2-yl)-N-cyclohexyl]aminoethyl]phenoxy]-2-methylpropionate

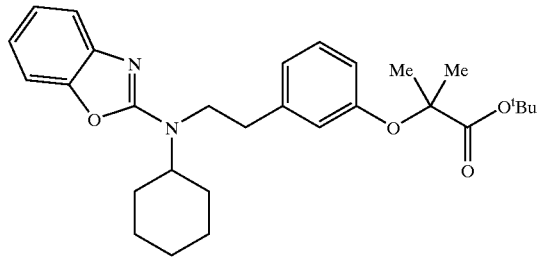

tert-Butyl 2-[3-(2-N-cyclohexylaminoethyl)phenoxy]-2-methylpropionate (50 mg, 0.138 mmol) was dissolved in acetonitrile (2 mL). Subsequently, diisopropylethylamine (36 μL, 0.207 mmol), and then 2-chlorobenzoxazole (24 μL, 0.021 mmol) were added thereto, the mixture was stirred under argon atmosphere overnight at 70° C. Ethyl acetate was added to the reaction mixture. Washing was performed with water and saturated brine, followed by drying over sodium sulfate. The reaction mixture was subjected to filtration, concentration under reduced pressure, and purification by preparative TLC (silica gel, n-hexane/ethyl acetate=10/1), whereby the target compound was obtained. (11 mg, 0.023 mmol, 17.0%).

Example 96

Synthesis of 2-[3-[2-[N-(Benzoxazol-2-yl)-N-cyclohexyl]aminoethyl]phenoxy]-2-methylpropionic Acid

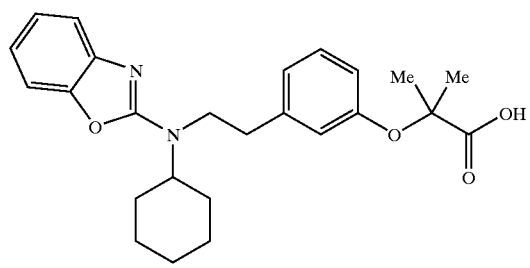

tert-Butyl 2-[(3-(2-(N-benzoxazol-2-yl-N-cyclohexylamino)ethyl)phenoxy]-2-methylpropionate (11 mg, 0.023 mmol) was dissolved in dichloromethane (3 mL). Subsequently, trifluoroacetic acid (0.5 mL) is added thereto, and the mixture was stirred at room temperature. After completion of reaction, the resultant mixture was subjected to toluene azeotrope and purification by preparative TLC (silica gel, chloroform/methanol=10/1), whereby the target compound was obtained (10 mg, 0. 023 mmol, q.).

¹H NMR (400 MHz, CDCl₃) δ 1.12–1.71 (m, 6H), 1.28 (s, 6H), 1.82–1.85 (m, 4H), 2.98 (t, J=8 Hz, 2H), 3.58–3.63 (m, 2H), 4.07–4.13 (m, 1H), 6.82–6.91 (m, 2H), 6.99–7.03 (m, 2H), 7.16 (t, J=8 Hz, 1H), 7.23 (t, J=8 Hz, 1H), 7.27 (d, J=8 Hz, 1H), 7.38 (d, J=8 Hz, 1H).

In a manner similar to that described in Example 96, the compounds of Example 97 through Example 100 were synthesized.

Example 97

2-[3-[2-[N-(Benzoxazol-2-yl)-N-(4-methoxybenzyl)]aminoethyl]phenoxy]-2-methylpropionic Acid

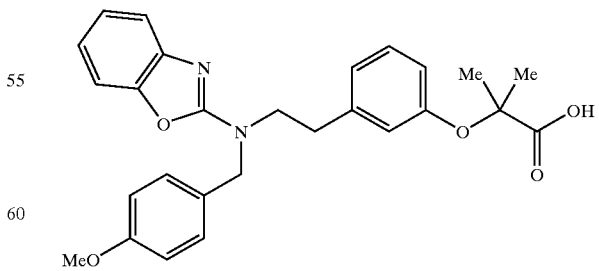

¹H NMR (400 MHz, CDCl₃) δ 1.55 (s, 6H), 2.80 (t, J=7 Hz, 2H), 3.59 (t, J=7 Hz, 2H), 3.76 (s, 3H), 4.74 (s, 2H), 6.70–6.83 (m, 3H), 7.00–7.27 (m, 8H), 7.38 (d, J=8 Hz, 1H).

Example 98

2-[3-[2-[N-(Benzoxazol-2-yl)-N-n-butyl]aminoethyl]phenoxy]-2-methylpropionic Acid

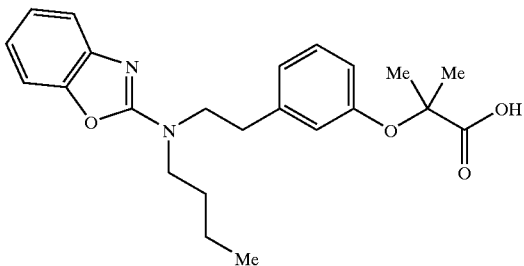

$^1$H NMR (400 MHz, CDCl$_3$) δ 0.90 (t, J=7 Hz, 3H), 1.18–1.34 (m, 2H), 1.52–1.60 (m, 2H), 1.57 (s, 6H), 2.86 (t, J=7 Hz, 2H), 3.34 (t, J=7 Hz, 2H), 3.66 (t, J=7 Hz, 2H), 6.77–6.85 (m, 3H), 6.99 (t, J=8 Hz, 1H), 7.06–7.15 (m, 2H), 7.23 (d, J=8 Hz, 1H), 7.36 (d, J=8 Hz, 1H).

Example 99

2-[4-[2-[N-(Benzoxazol-2-yl)-N-cyclohexyl]aminoethyl]phenoxy]-2-methylpropionic Acid

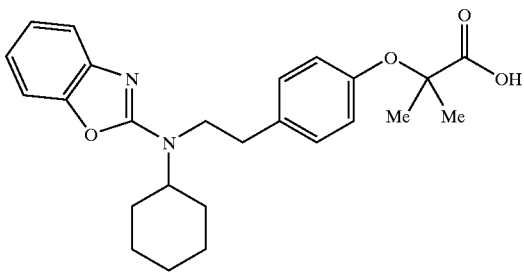

$^1$H NMR (400 MHz, CDCl$_3$) δ 1.11–1.70 (m, 6H), 1.58 (s, 6H), 1.80–1.84 (m, 4H), 2.93 (t, J=8 Hz, 2H), 3.59 (t, J=8 Hz, 2H), 4.03–4.09 (m, 1H), 6.88 (d, J=8 Hz, 2H), 7.03 (t, J=8 Hz, 1H), 7.13 (d, J=8 Hz, 2H), 7.17 (t, J=8 Hz, 1H), 7.27 (d, J=8 Hz, 1H), 7.43 (d, J=8 Hz, 1H).

Example 100

2-[3-[2-[N-(Benzoxazol-2-yl)-N-(2-(4-chlorophenyl)ethyl)]aminoethyl]phenoxy]-2-methylpropionic Acid

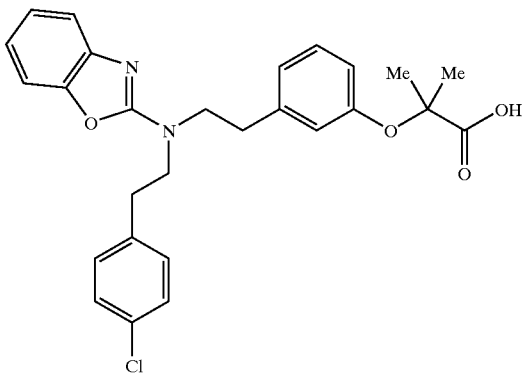

$^1$H NMR (400 MHz, CDCl$_3$) δ 1.50 (s, 6H), 2.85 (t, J=6 Hz, 2H), 2.89 (t, J=7 Hz, 2H), 3.55–3.65 (m, 4H), 6.70 (s, 1H), 6.72 (d, J=8 Hz, 1H), 6.85 (d, J=7 Hz, 1H), 7.09–7.26 (m, 8H), 7.45 (d, J=Hz, 1H).

Production Example 13

Synthesis of tert-Butyl 2-[3-[2-(ethoxycarbonyl)ethenyl]phenoxy]-2-methylpropionate

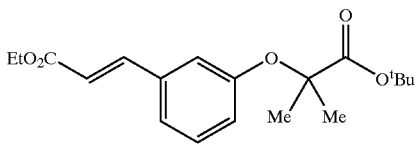

60% Sodium hydride (6.1 g, 0.15 mol) was dissolved in tetrahydrofuran. Subsequently, triethylphosphonoacetate (30.2 mL, 0.15 mol) was added dropwise under ice-cooling. After 30 minutes, tert-butyl 2-(3-formylphenoxy)-2-methylpropionate (33.6 g, 0.13 mol) was added under ice-cooling, the mixture was stirred for one hour. Thereafter, the temperature of the mixture was raised to room temperature, and the mixture was stirred for five hours. An aqueous ammonium chloride solution was added thereto, and the resultant mixture was extracted with ethyl acetate. The organic layer was washed with saturated brine, followed by drying over sodium sulfate, concentration under reduced pressure, and purification by silica gel chromatography (n-hexane/ethyl acetate=9/1), whereby the target compound was obtained (39.1 g, 92%).

$^1$H NMR (400 MHz, CDCl$_3$) δ 1.33 (t, J=7 Hz, 3H), 1.43 (s, 9H), 1.58 (s, 6H), 4.26 (q, J=7 Hz, 2H), 6.38 (d, J=16 Hz, 1H), 6.87 (d, J=8 Hz, 1H), 6.99–7.04 (m, 1H), 7.13 (d, J=8 Hz, 1H), 7.22–7.26 (m, 1H), 7.60 (d, J=16 Hz, 1H).

Production Example 14

Synthesis of tert-Butyl 2-[3-[2-(Ethoxycarbonyl)ethyl]phenoxy]-2-methylpropionate

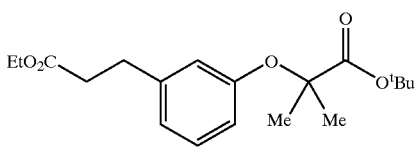

tert-Butyl 2-[3-[2-(ethoxycarbonyl)ethenyl]phenoxy]-2-methylpropionate (39.1 g, 0.12 mol) was dissolved in ethanol. Subsequently, 10% palladium in carbon (3.9 g) was added thereto, the mixture was stirred under hydrogen atmosphere overnight at room temperature. The resultant mixture was subjected to filtration by use of Celite, concentration under reduced pressure, and purification by silica gel chromatography (n-hexane/ethyl acetate=20/1), whereby the target compound was obtained (37.1 g, 94%).

$^1$H NMR (400 MHz, CDCl$_3$) δ 1.23 (t, J=7 Hz, 3H), 1.44 (s, 9H), 1.55 (s, 6H), 2.58 (t, J=8 Hz, 2H), 2.88 (t, J=8 Hz, 2H), 4.13 (q, J=7Hz, 2H), 6.68 (d, J=8 Hz, 1H), 6.72 (s, 1H), 6.80 (d, J=8 Hz, 1H), 7.13 (t, J=8 Hz, 1H).

Production Example 15

Synthesis of 3-[3-(1-tert-Butoxycarbonyl-1-methylethoxy)phenyl]propionic Acid

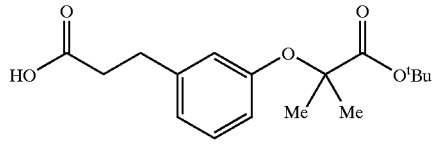

tert-Butyl 2-[3-[2-(ethoxycarbonyl)ethyl]phenoxy]-2-methylpropionate (37.1 g, 0.11 mmol) was dissolved in ethanol. Subsequently, aqueous 10% potassium hydroxide solution was added dropwise, and the mixture was stirred overnight at room temperature. The resultant mixture was concentrated under reduced pressure, and then an aqueous 5% potassium hydrogensulfate solution was added thereto. The reaction mixture was extracted with ethyl acetate, and the organic layer was washed with saturated brine. The mixture was subjected to drying over sodium sulfate, concentration under reduced pressure, and purification by silica gel chromatography (n-hexane/ethyl acetate=3/2), whereby the target compound was obtained (32.0 g, 94%).

$^1$H NMR (400 MHz, CDCl$_3$) δ 1.44 (s, 9H), 1.56 (s, 6H), 2.65 (t, J=8 Hz, 2H), 2.90 (t, J=8 Hz, 2H), 6.68–6.73 (m, 2H), 6.82 (d, J=8 Hz, 1H), 7.15 (t, J=8 Hz, 1H).

Production Example 16

Synthesis of tert-Butyl 2-[3-(3-Hydroxypropyl)phenoxy]-2-methylpropionate

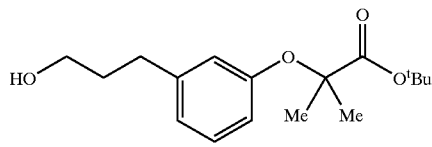

3-[3-(1-tert-Butoxycarbonyl-1-methylethoxy)phenyl]propionic acid (10.0 g, 32.4 mmol) was dissolved in tetrahydrofuran (50 mL). Subsequently, triethylamine (3.6 g, 35.6 mmol) was added dropwise thereto. Ethyl chlorocarbonate (3.87 g, 35.6 mmol) was added under ice-cooling, and the mixture was stirred for one hour at room temperature. Sodium borohydride (2.45 g, 64.8 mmol) in tetrahydrofuran-water solution was added dropwise under ice-cooling, and the mixture was stirred for two hours at room temperature. Water was added thereto, and the reaction mixture was extracted with ethyl acetate. The organic layer was sequentially washed with diluted hydrochloric acid and saturated brine. The resultant mixture was subjected to drying over sodium sulfate, concentration under reduced pressure, and purification by silica gel chromatography (n-hexane/ethyl acetate=7/3), whereby the target compound was obtained (9.8 g (q.)).

$^1$H NMR (400 MHz, CDCl$_3$) δ 1.44 (s, 9H), 1.60 (s, 6H), 1.61 (br.s, 1H), 1.87 (m, 2H), 2.65 (t, J=8 Hz, 2H), 3.66 (t, J=6 Hz, 2H), 6.67 (d, J=7 Hz, 1H), 6.72 (s, 1H), 6.81 (d, J=7 Hz, 1H), 7.13 (t, J=7 Hz, 1H).

Production Example 17

Synthesis of tert-Butyl 2-[3-(3-methanesulfonyloxypropyl)phenoxy]-2-methylpropionate

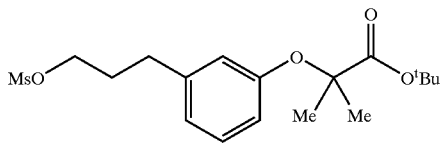

tert-Butyl 2-[3-(3-hydroxypropyl)phenoxy]-2-methylpropionate (10.1 g, 34.3 mmol) was dissolved in methylene chloride (50 mL). Subsequently, triethylamine (6.94 g, 68.6 mmol) was added thereto. Mesyl chloride (4.71 g, 41.2 mmol) was added dropwise under ice-cooling, and the mixture was stirred for five hours at room temperature. Diluted hydrochloric acid was added thereto, the resultant mixture was extracted with chloroform. The reaction mixture was subjected to drying over sodium sulfate, concentration under reduced pressure, and purification by silica gel chromatography (n-hexane/ethyl acetate=4/1), whereby the target compound was obtained (7.8 g, 61%).

$^1$H NMR (400 MHz, CDCl$_3$) δ 1.44 (s, 9H), 1.56 (s, 6H), 2.05 (quintet, J=7 Hz, 2H), 2.69 (t, J=7 Hz, 2H), 2.99 (s, 3H), 4.21 (t, J=7 Hz, 2H), 6.67–6.72 (m, 2H), 6.79 (t, J=8 Hz, 1H), 7.15 (d, J=8 Hz, 1H).

Production Example 18

Synthesis of tert-Butyl 2-[3-(3-phthalimidopropyl)phenoxy]-2-methylpropionate

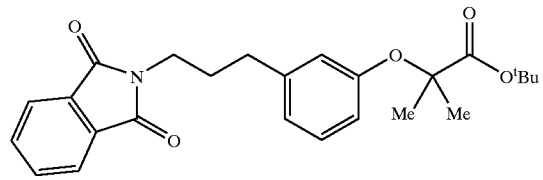

tert-Butyl 2-[3-(3-methanesulfonyloxypropyl)phenoxy]-2-methylpropionate (1.93 g, 5.18 mmol) was dissolved in dimethylformamide (10.0 mL). Subsequently, potassium phthalimide (1.15 g, 6.22 mmol) was added thereto, and the mixture was stirred overnight at 80° C. Water was added thereto, and the resultant mixture was extracted with diethyl ether. The reaction mixture was subjected to drying over sodium sulfate, concentration under reduced pressure, and purification by silica gel chromatography (n-hexane/ethyl acetate=5/1), thereby the target compound was obtained (1.8 g, 82%).

$^1$H NMR (400 MHz, CDCl$_3$) δ 1.43 (s, 9H), 1.55 (s, 6H), 2.05 (quintet, J=8 Hz, 2H), 2.62 (t, J=8 Hz, 2H), 3.73 (t, J=8 Hz, 2H), 6.65 (d, J=8 Hz, 1H), 6.71 (s, 1H), 6.81 (d, J=8 Hz, 1H), 7.11 (d, J=8 Hz, 1H), 7.69–7.73 (m, 2H), 7.82–7.86 (m, 2H).

Production Example 19

Synthesis of tert-Butyl 2-[3-(3-Aminopropyl)phenoxy]-2-methylpropionate

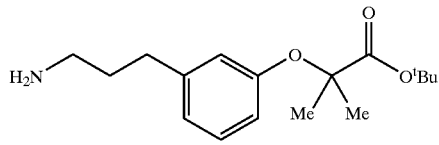

tert-Butyl 2-[3-(3-phthalimidopropyl)phenoxy]-2-methylpropionate (1.87 g, 4.41 mmol) was dissolved in ethanol (10.0 mL) Subsequently, hydrazine monohydrate (184 mg, 5.74 mmol) was added dropwise, and the mixture was stirred overnight at 80° C. Thereafter, the temperature of the mixture was returned to room temperature, and the mixture was subjected to filtration. The resultant filtrate was subjected to drying over sodium sulfate, concentration under reduced pressure, and purification by silica gel chromatography (chloroform/methanol (saturated with ammonia)=20/1), whereby the target compound was obtained (560 mg, 43%).

$^1$H NMR (400 MHz, CDCl$_3$) δ 1.44 (s, 9H), 1.56 (s, 6H), 1.74 (quintet, J=7 Hz, 2H), 2.59 (t, J=7 Hz, 2H), 2.71 (t, J=7 Hz, 2H), 6.66 (dd, J=8, 2 Hz, 1H), 6.71 (s, 1H), 6.79 (d, J=8 Hz, 1H), 7.12 (d, J=8 Hz, 7H).

Production Example 20

Synthesis of tert-Butyl 2-[3-[3-(N-Benzoxazol-2-yl)aminopropyl]phenoxy]-2-methylpropionate

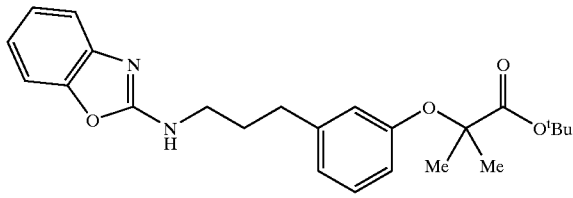

tert-Butyl 2-[3-(3-aminopropyl)phenoxy]-2-methylpropionate (167 mg, 0.57 mmol) was dissolved in tetrahydrofuran (3.0 mL). Subsequently, diisopropylethylamine (73.6 mg, 0.57 mmol) and then 2-chlorobenzoxazole (96.2 mg, 0.63 mmol) were added dropwise thereto, and the mixture was stirred for four hours at room temperature. Water was added thereto, and the resultant mixture was extracted with ethyl acetate. The organic layer was washed with saturated brine, followed by drying over sodium sulfate, concentration under reduced pressure, and purification by silica gel chromatography (n-hexane/ethyl acetate=3/1), whereby the target compound was obtained (173 mg, 74%).

$^1$H NMR (400 MHz, CDCl$_3$) δ 1.43 (s, 9H), 1.55 (s, 6H), 1.99 (quintet, J=7 Hz, 2H), 2.67 (t, J=7 Hz, 2H), 3.49 (br.s, 2H), 5.46 (br.s, 1H), 6.68 (dd, J=8, 2 Hz, 1H), 6.73 (br.s, 1H), 6.79 (d, J=8 Hz, 1H), 7.01 (td, J=8, 1 Hz, 1H), 7.11–7.17 (m, 2H), 7.23 (d, J=8 Hz, 1H), 7.34 (d, J=8 Hz, 1H).

Production Example 21

Synthesis of tert-Butyl 2-[3-[3-[N-(Benzoxazol-2-yl)-N-(4-methoxybenzyl)]aminopropyl]phenoxy]-2-methylpropionate

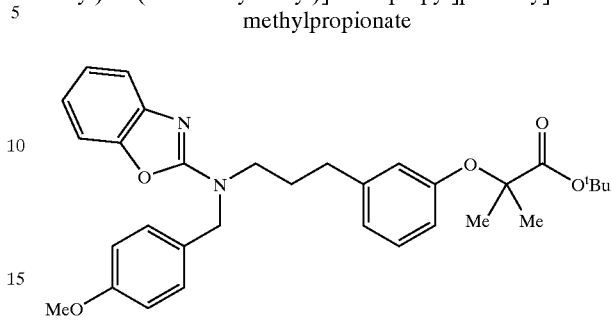

tert-Butyl 2-[3-[3-(N-benzoxazol-2-yl)aminopropyl]phenoxy]-2-methylpropionate (30 mg, 0.07 mmol) was dissolved in acetonitrile (3.0 mL), and cesium carbonate (47 mg, 0.15 mmol) was added thereto. Subsequently, 4-methoxybenzyl chloride (17.2 mg, 0.11 mmol) was added dropwise, and the mixture was stirred overnight at 70° C. Water was added thereto, and the resultant mixture was extracted with ethyl acetate. The organic layer was washed with saturated brine, followed by drying over sodium sulfate, concentration under reduced pressure, and purification by silica gel chromatography (n-hexane/ethyl acetate=5/1), whereby the target compound was obtained (16.5 mg, 43%).

Example 101

Synthesis of 2-[3-[3-[N-(benzoxazol-2-yl)-N-(4-methoxybenzyl)]aminopropyl]phenoxy]-2-methylpropionic Acid

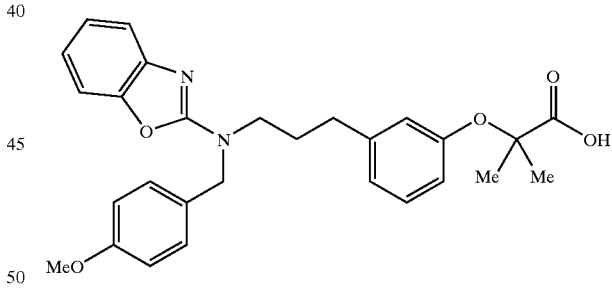

tert-Butyl 2-[3-[3-[N-(benzoxazol-2-yl)-N-(4-methoxybenzyl)]aminopropyl]phenoxy]-2-methylpropionate (17.2 mg, 0.03 mmol) was dissolved in methylene chloride (1.0 mL). Subsequently, 50% trifluoroacetic acid in methylene chloride solution was added dropwise thereto, and the mixture was stirred for three hours at room temperature. The resultant mixture was subjected to toluene azeotrope and purification by preparative TLC (chloroform/methanol=20/1), whereby the target compound was obtained (8.7 mg, 61%).

MS (m/z) 474 (M$^+$).

In a manner similar to that described in Example 101, the compounds of Example 102 through Example 131 were synthesized.

Example 102

2-[3-[3-[N-(Benzoxazol-2-yl)-N-(3-phenylpropyl)]aminopropyl]phenoxy]-2-methylpropionic Acid

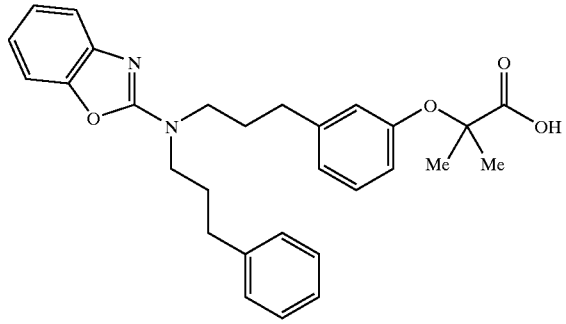

$^1$H NMR (400 MHz, CDCl$_3$) δ 1.67 (s, 6H), 1.90–2.05 (m, 4H), 2.65–2.69 (m, 4H), 3.34–3.40 (m, 2H), 3.50 (t, J=8 Hz, 2H), 6.75–6.90 (m, 2H), 6.90 (s, 1H), 7.00 (t, J=8 Hz, 1H), 7.06–7.30 (m, 8H), 7.35 (d, J=8 Hz, 1H).

Example 103

2-[3-[3-[N-(Benzoxazol-2-yl)-N-n-propyl]aminopropyl]phenoxy]-2-methylpropionic Acid

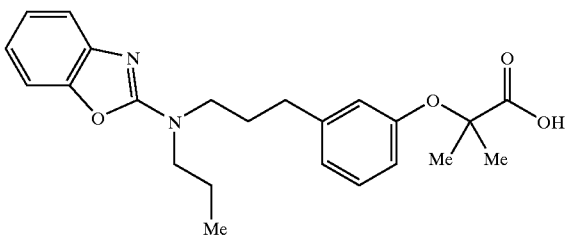

MS (m/z) 396 (M$^+$).

Example 104

2-[3-[3-[N-(Benzoxazol-2-yl)-N-n-butyl]aminopropyl]phenoxy]-2-methylpropionic Acid

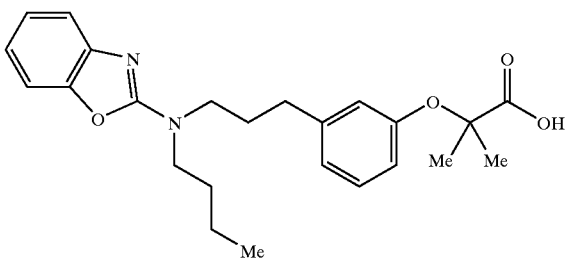

MS (m/z) 410 (M$^+$).

Example 105

2-[3-[3-[N-(Benzoxazol-2-yl)-N-n-pentyl]aminopropyl]phenoxy]-2-methylpropionic Acid

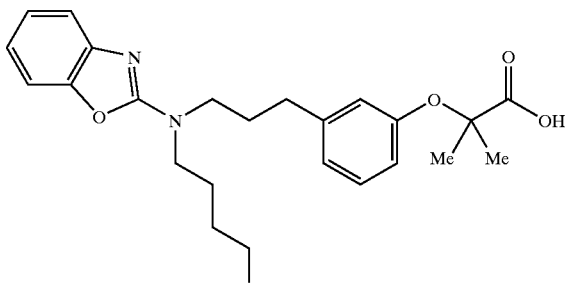

MS (m/z) 424 (M$^+$).

Example 106

2-[3-[3-[N-(Benzoxazol-2-yl)-N-n-hexyl]aminopropyl]phenoxy]-2-methylpropionic Acid

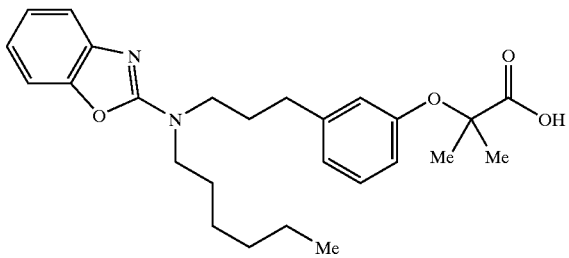

MS (m/z) 438 (M$^+$).

Example 107

2-[3-[3-[N-(Benzoxazol-2-yl)-N-n-heptyl]aminopropyl]phenoxy]-2-methylpropionic Acid

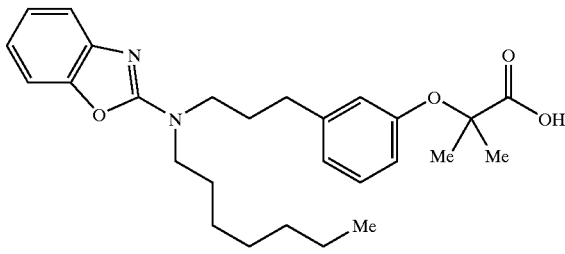

MS (m/z) 452 (M$^+$).

Example 108

2-[3-[3-[N-(Benzoxazol-2-yl)-N-n-octyl]aminopropyl]phenoxy]-2-methylpropionic Acid

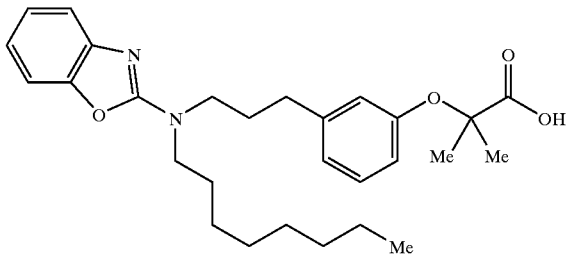

MS (m/z) 466 (M$^+$).

Example 109

2-[3-[3-[N-(Benzoxazol-2-yl)-N-isopropyl]aminopropyl]phenoxy]-2-methylpropionic Acid

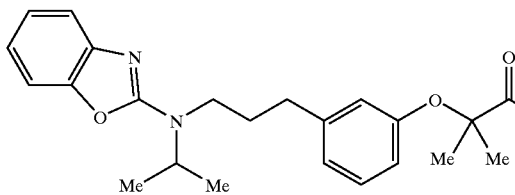

MS (m/z) 396 (M$^+$).

Example 110

2-[3-[3-[N-(Benzoxazol-2-yl)-N-(4-methylpentyl)]aminopropyl]phenoxy]-2-methylpropionic Acid

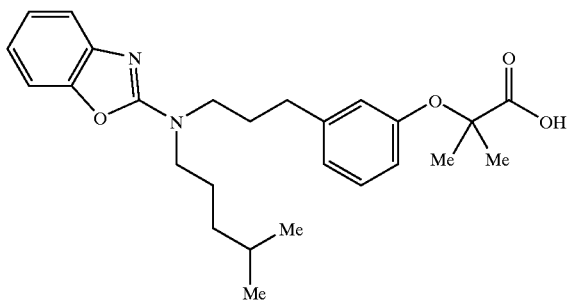

MS (m/z) 438 (M$^+$).

Example 111

2-[3-[3-[N-(Benzoxazol-2-yl)-N-cyclopropylmethyl]aminopropyl]phenoxy]-2-methylpropionic Acid

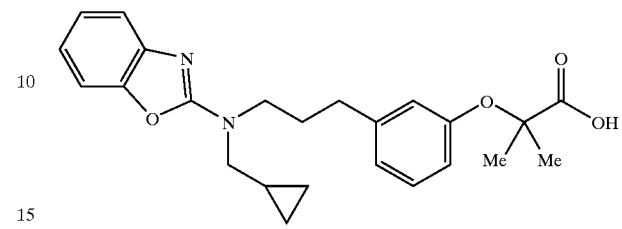

MS (m/z) 408 (M$^+$).

Example 112

2-[3-[3-[N-(Benzoxazol-2-yl)-N-ethoxycarbonylmethyl]aminopropyl]phenoxy]-2-methylpropionic Acid

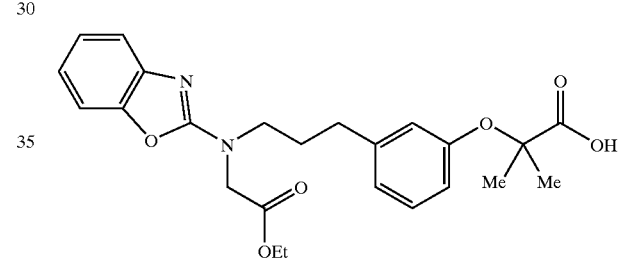

MS (m/z) 440 (M$^+$).

Example 113

2-[4-[3-[N-(Benzoxazol-2-yl)-N-methyl]aminopropyl]phenoxy]-2-methylpropionic Acid

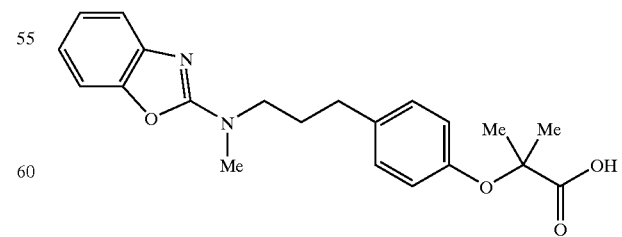

MS (m/z) 368 (M$^+$).

Example 114

2-[4-[3-[N-(Benzoxazol-2-yl)-N-ethyl]aminopropyl]phenoxy]-2-methylpropionic Acid

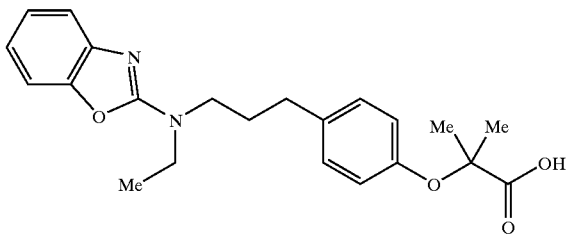

MS (m/z) 382 (M$^+$).

Example 115

2-[4-[3-[N-(Benzoxazol-2-yl)-N-n-butyl]aminopropyl]phenoxy]-2-methylpropionic Acid

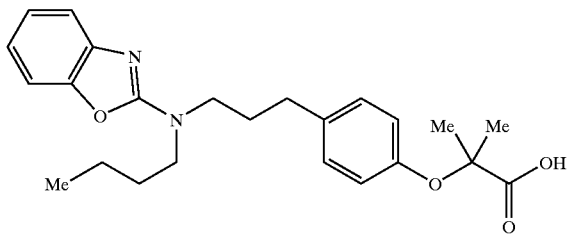

MS (m/z) 410 (M$^+$).

Example 116

2-[4-[3-[N-(Benzoxazol-2-yl)-N-n-pentyl]aminopropyl]phenoxy]-2-methylpropionic Acid

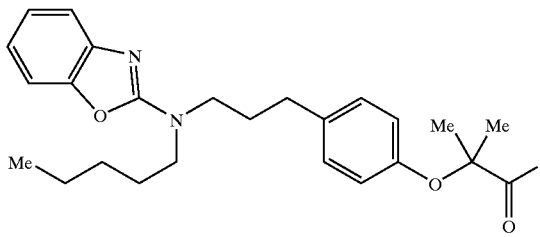

MS (m/z) 424 (M$^+$).

Example 117

2-[4-[3-[N-(Benzoxazol-2-yl)-N-n-hexyl]aminopropyl]phenoxy]-2-methylpropionic Acid

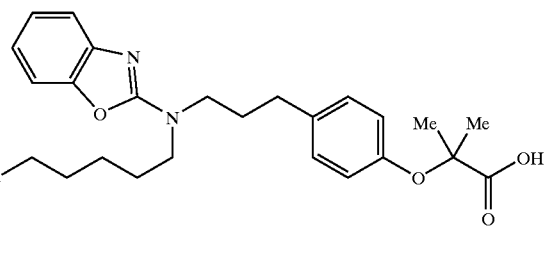

MS (m/z) 438 (M$^+$).

Example 118

2-[4-[3-[N-(Benzoxazol-2-yl)-N-n-heptyl]aminopropyl]phenoxy]-2-methylpropionic Acid

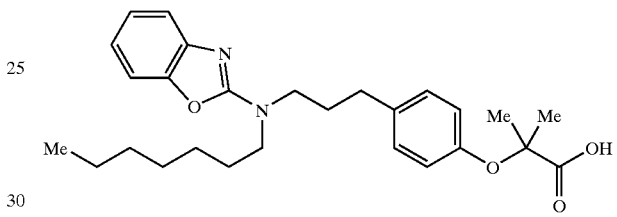

MS (m/z) 452 (M$^+$).

Example 119

2-[4-[3-[N-(Benzoxazol-2-yl)-N-n-octyl]aminopropyl]phenoxy]-2-methylpropionic Acid

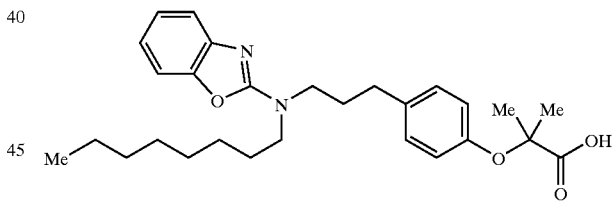

MS (m/z) 466 (M$^+$).

Example 120

2-[4-[3-[N-(Benzoxazol-2-yl)-N-(5-hexenyl)]aminopropyl]phenoxy]-2-methylpropionic Acid

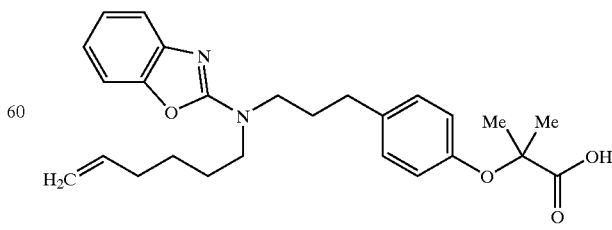

MS (m/z) 436 (M$^+$).

Example 121

2-[3-[3-[N-(Benzoxazol-2-yl)-N-(2-butynyl)]aminopropyl]phenoxy]-2-methylpropionic Acid

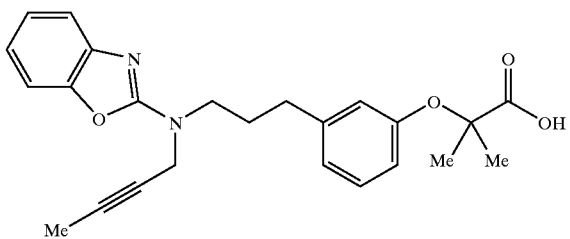

MS (m/z) 407 (M+1) (FAB).

Example 122

2-[4-[3-[N-(Benzoxazol-2-yl)-N-cyclohexyl]aminopropyl]phenoxy]-2-methylpropionic Acid

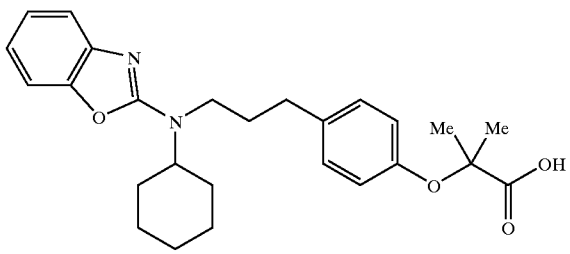

MS (m/z) 436 (M+).

Example 123

2-[3-[3-[N-(Benzoxazol-2-yl)-N-methyl]aminopropyl]phenoxy]-2-methylpropionic Acid

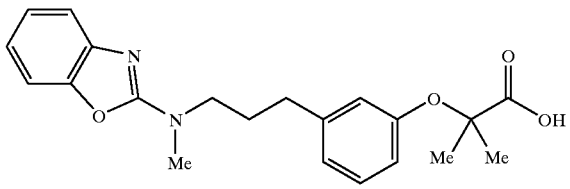

MS (m/z) 368 (M+).

Example 124

2-[3-[3-[N-(Benzoxazol-2-yl)-N-ethyl]aminopropyl]phenoxy]-2-methylpropionic Acid

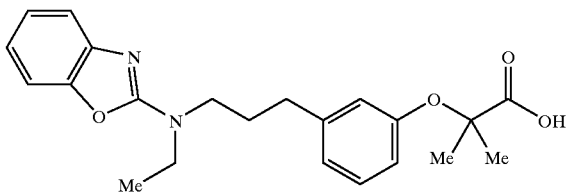

MS (m/z) 382 (M+).

Example 125

2-[4-[3-[N-(Benzoxazol-2-yl)-N-ethoxycarbonylmethyl]aminopropyl]phenoxy]-2-methylpropionic Acid

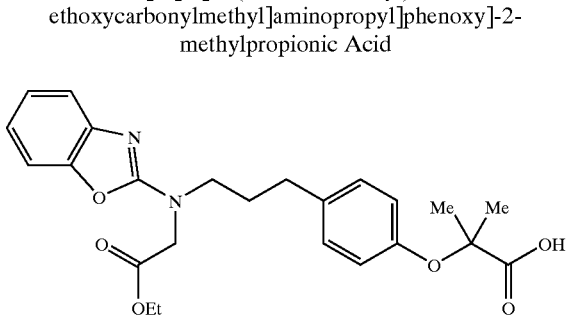

MS (m/z) 440 (M+).

Example 126

2-[4-[3-[N-(Benzoxazol-2-yl)-N-(2-butynyl)]aminopropyl]phenoxy]-2-methylpropionic Acid

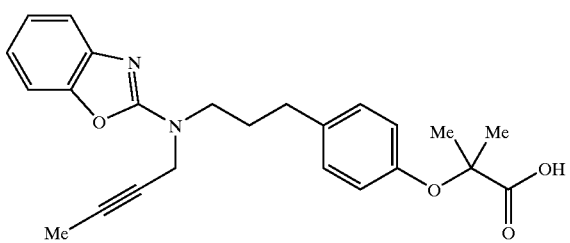

MS (m/z) 406 (M+).

Example 127

2-[4-[3-[N-(Benzoxazol-2-yl)-N-(naphth-1-ylmethyl)]aminopropyl]phenoxy]-2-methylpropionic Acid

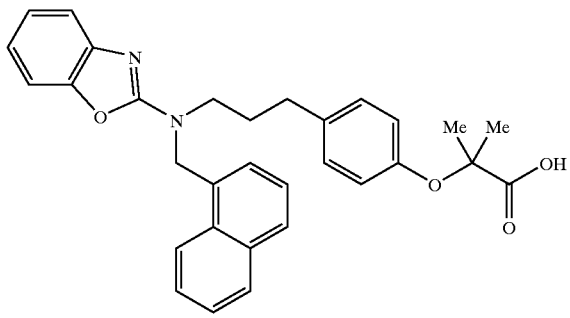

MS (m/z) 494 (M+).

Example 128

2-[4-[3-[N-(Benzoxazol-2-yl)-N-(4-methoxybenzyl)]aminopropyl]phenoxy]-2-methylpropionic Acid

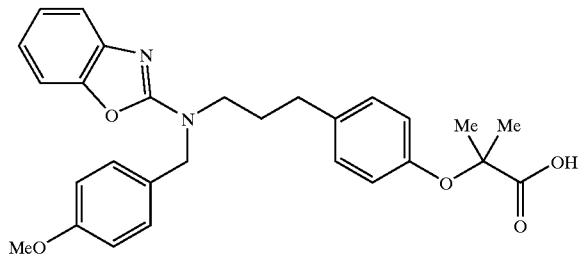

MS (m/z) 474 (M+).

Example 129

2-[3-[3-[N-(Benzoxazol-2-yl)-N-(3-methylbutyl)]aminopropyl]phenoxy]-2-methylpropionic Acid

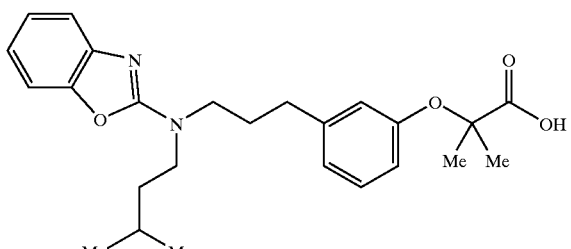

MS (m/z) 424 (M+).

Example 130

2-[4-[3-[N-(Benzoxazol-2-yl)-N-(3-methylbutyl)]aminopropyl]phenoxy]-2-methylpropionic Acid

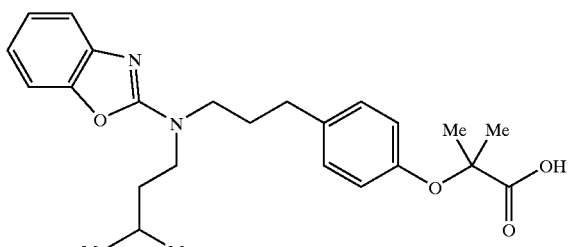

MS (m/z) 424 (M+).

Example 131

2-[4-[3-[N-(Benzoxazol-2-yl)-N-(2-(4-chlorophenyl)ethyl)]aminopropyl]phenoxy]-2-methylpropionic Acid

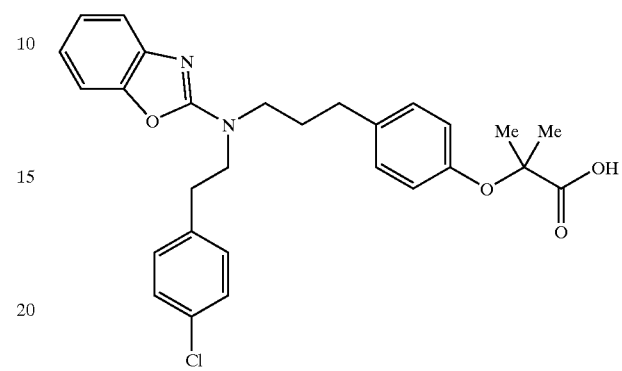

MS (m/z) 492, 494 (M+).

Production Example 22

Synthesis of 3-(4-Hydroxyphenyl)-N-n-propylpropionamide

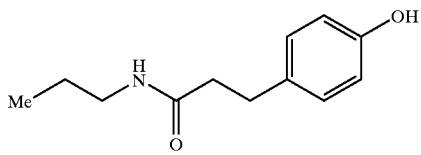

3-(4-Hydroxyphenyl)propionic acid (12.0 g, 72.0 mmol) was dissolved in tetrahydrofuran (20 mL). n-Propylamine (5.1 g, 86.4 mmol) was added dropwise at room temperature. Subsequently, under ice-cooling, solution (20 mL) of WSCI-hydrochloric acid salt (16.5 g, 86.4 mmol) in methylene chloride was slowly added thereto, and the resultant mixture was stirred overnight. Diluted hydrochloric acid was added dropwise under ice-cooling, and the mixture was extracted with chloroform. The organic layer was washed with saturated brine, followed by drying over sodium sulfate, concentration under reduced pressure, and purification by silica gel chromatography (chloroform/methanol=50/1), whereby the target compound was obtained (9.7 g, 65%).

$^1$H NMR (400 MHz, CDCl$_3$) δ 0.83 (t, J=7 Hz, 3H), 1.43 (m, 2H), 2.44 (t, J=8 Hz, 2H), 2.87 (t, J=8 Hz, 2H), 3.15 (m, 2H), 5.56 (s, 1H), 6.76 (d, J=8 Hz, 2H), 7.00 (d, J=8 Hz, 2H).

Production Example 23

Synthesis of tert-Butyl 2-[4-[2-(N-n-propylaminocarbonyl)ethyl]-2-methylpropionate

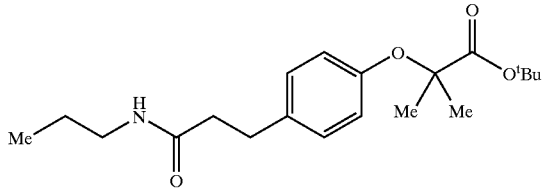

3-(4-Hydroxyphenyl)-N-n-propylpropionamide (9.7 g, 47.0 mmol) was dissolved in acetonitrile (20 mL), and potassium carbonate (22.4 g, 163 mmol) was added thereto. Subsequently, tert-butyl 2-bromoisobutyrate (31.1 g, 140 mmol) was added thereto, and the mixture was stirred overnight at 75° C. Water was added thereto, and the resultant mixture was extracted with ethyl acetate. The organic layer was washed with saturated brine, followed by drying over sodium sulfate, concentration under reduced pressure, and purification by silica gel chromatography (n-hexane/ethyl acetate=10/1), whereby the target compound was obtained (9.6 g, 59%).

$^1$H NMR (400 MHz, CDCl$_3$) δ 0.85 (t, J=7 Hz, 3H), 1.39–1.48 (m, 2H), 1.45 (s, 9H), 1.54 (s, 6H), 2.42 (t, J=8 Hz, 2H), 2.89 (t, J=8 Hz, 2H), 3.16 (m, 2H), 5.32 (br.s, 1H), 6.78 (d, J=9 Hz, 2H), 7.05 (d, J=9 Hz, 2H).

Production Example 24

Synthesis of tert-Butyl 2-[4-[3-(N-n-propyl)aminopropyl]phenoxy]-2-methylpropionate

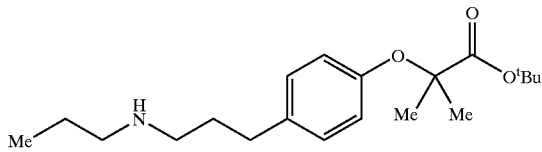

tert-Butyl 2-[4-[2-(N-n-propylaminocarbonyl)ethyl]phenoxy]-2-methylpropionate (4.0 g, 11.4 mmol) was dissolved in tetrahydrofuran (10 mL). 1.0M Borane-tetrahydrofuran complex in tetrahydrofuran solution (34.3 mL, 34.3 mmol) was added dropwise, the mixture was stirred for three hours at 50° C. Concentrated hydrochloric acid was added under ice-cooling, the mixture was stirred for three hours at room temperature. Aqueous 80% ethylamine solution was added dropwise under ice-cooling, and the mixture was extracted with ethyl acetate. The organic layer was washed with saturated brine, followed by drying over sodium sulfate, concentration under reduced pressure, and purification by silica gel chromatography (chloroform/methanol=50/1), whereby the target compound was obtained (2.3 g, 59%).

$^1$H NMR (400 MHz, CDCl$_3$) δ 0.90 (t, J=7 Hz, 3H), 1.41–1.56 (m, 2H), 1.44 (s, 9H), 1.54 (s, 6H), 1.80 (quintet, J=8 Hz, 2H), 2.55–2.60 (m, 4H), 2.63 (t, J=7 Hz, 2H), 6.77 (d, J=8 Hz, 2H), 7.03 (d, J=8 Hz, 2H).

Production Example 25

Synthesis of tert-Butyl 2-[4-[3-[N-(Benzoxazol-2-yl)-N-n-propyl]aminopropyl]phenoxy]-2-methylpropionate

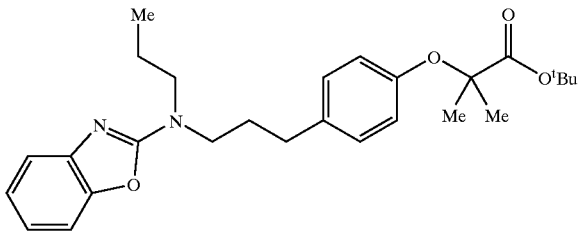

tert-Butyl 2-[4-[3-(N-n-propyl)aminopropyl]phenoxy]-2-methylpropionate (1.8 g, 5.3 mmol) was dissolved in dimethylformamide (5.0 mL), and diisopropylethylamine (1.02 g, 7.95 mmol) was added dropwise thereto. Subsequently, 2-chlorobenzoxazole (977 mg, 6.36 mmol) was added dropwise thereto, the mixture was stirred for two hours at 50° C. Water was added thereto, and the resultant mixture was extracted with ethyl acetate. The organic layer was washed with saturated brine, followed by drying over sodium sulfate, concentration under reduced pressure, and purification by silica gel chromatography (n-hexane/ethyl acetate= 4/1), whereby the target compound was obtained (1.1 g, 46%). $^1$H NMR (400 MHz, CDCl$_3$) δ 0.94 (t, J=7 Hz, 3H), 1.44 (s, 9H), 1.54 (s, 6H), 1.64–1.69 (m, 2H), 1.94–2.4 (m, 2H), 2.63 (t, J=8 Hz, 2H), 3.45 (t, J=8 Hz, 2H), 3.54 (t, J=7 Hz, 2H), 6.79 (d, J=9 Hz, 2H), 6.98 (t, J=8 Hz, 1H), 7.05 (d, J=9 Hz, 2H), 7.14 (t, J=8 Hz, 1H), 7.22 (d, J=8 Hz, 1H), 7.34 (d, J=8 Hz, 1H).

Example 132

Synthesis of 2-[4-[3-[N-(Benzoxazol-2-yl)-N-n-propyl]aminopropyl]phenoxy]-2-methylpropionic Acid

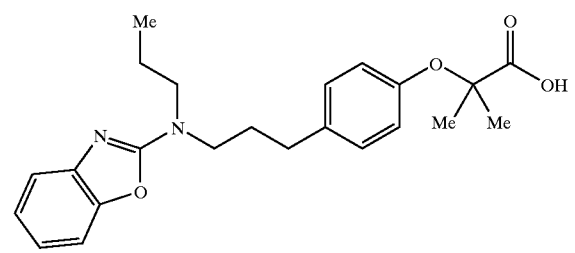

tert-Butyl 2-[4-[3-N-(benzoxazol-2-yl)-N-n-propyl]aminopropyl]phenoxy]-2-methylpropionate (1.1 g, 2.43 mmol) was dissolved in methylene chloride (10.0 mL). Subsequently, 50% trifluoroacetic acid in methylene chloride solution (3.0 g) was added dropwise thereto, and the mixture was stirred for three hours at room temperature. The resultant mixture was subjected to concentration under reduced pressure, toluene azeotrope, and purification by silica gel chromatography (chloroform/methanol=50/1), whereby the target compound was obtained (1.0 g, q.).

$^1$H NMR (400 MHz, CDCl$_3$) δ 0.92 (t, J=7 Hz, 3H), 1.59 (s, 6H), 1.63–1.69 (m, 2H), 1.96 (quintet, J=7 Hz, 2H), 2.59 (t, J=7 Hz, 2H), 3.44 (t, J=7 Hz, 2H), 3.56 (t, J=7 Hz, 2H), 6.84 (d, J=8 Hz, 2H), 7.00 (d, J=8 Hz, 2H), 7.05 (t, J=8 Hz, 1H), 7.18 (t, J=8 Hz, 1H), 7.25 (d, J=8 Hz, 1H), 7.47 (d, J=8 Hz, 1H), 11.9 (br.s, 1H).

85

Synthesis of Sodium 2-[4-[3-[N-(benzoxazol-2-yl)-N-n-propyl]aminopropyl]phenoxy]-2-methylpropionate

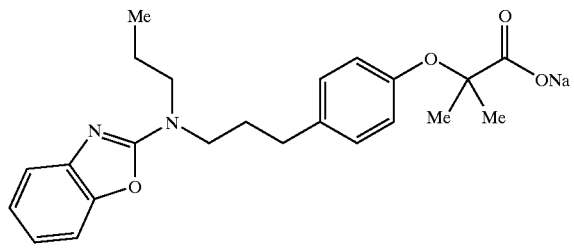

2-[4-[3-[N-(Benzoxazol-2-yl)-N-n-propyl]aminopropyl]phenoxy]-2-methylpropionic acid (1.0 g, 2.6 mmol) was dissolved in methanol. Subsequently, sodium methoxide (142 mg, 2.6 mmol) in methanol was added thereto at room temperature, and the mixture was stirred for one hour. The resultant mixture was concentrated under reduced pressure, and hexane was added to the resultant concentrate, to thereby precipitate a solid. The thus-obtained solid was purified, whereby a white amorphous powder was obtained (820 mg, 75%).

$^1$H NMR (400 MHz, CDCl$_3$) δ 0.89 (t, J=7 Hz, 3H), 1.29 (s, 6H), 1.59–1.69 (m, 2H), 1.82–1.90 (m, 2H), 2.54 (t, J=7 Hz, 2H), 3.41 (t, J=7 Hz, 2H), 3.49 (t, J=7 Hz, 2H), 6.70 (d, J=8 Hz, 2H), 6.94 (d, J=8 Hz, 2H), 6.95 (t, J=8 Hz, 1H), 7.11 (t, J=8 Hz, 1H), 7.20 (d, J=8 Hz, 1H), 7.32 (d, J=8 Hz, 1H).

In a manner similar to that described in Example 132, the compound of Example 133 was synthesized.

Example 133

2-[4-[3-[N-(Benzoxazol-2-yl)-N-isopropyl]aminopropyl]phenoxy]-2-methylpropionic Acid

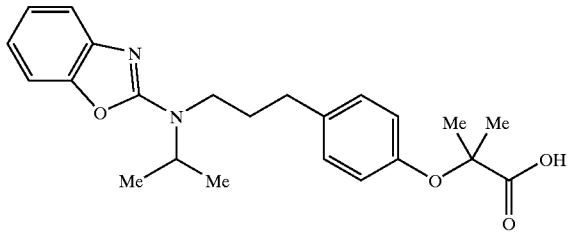

$^1$H NMR (400 MHz, CDCl$_3$) δ 1.28 (d, J=7 Hz, 6H), 1.56 (s, 6H), 1.96–2.10 (m, 2H), 2.65 (t, J=8 Hz, 2H), 3.51 (t, J=8 Hz, 2H), 4.46 (septet, J=7 Hz, 1H), 6.86 (d, J=8 Hz, 2H), 7.06 (d, J=8 Hz, 2H), 7.16 (t, J=8 Hz, 1H), 7.25–7.31 (m, 2H), 7.55 (d, J=8 Hz, 1H), 11.2 (br.s, 1H).

86

Production Example 26

Synthesis of tert-Butyl 2-(3-Methoxycarbonylphenoxy)-2-methylpropionate

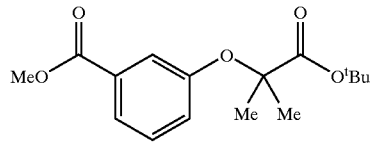

Methyl 3-hydroxybenzoate (17.05 g, 0.112 mol) was dissolved in dimethylformamide (100 mL). Subsequently, potassium carbonate (20.12 g, 0.145 mol) and then tert-butyl 2-bromoisobutyrate (50.00 g, 0.224 mol) were added thereto, and the mixture was stirred overnight at 80° C. The reaction mixture was concentrated under reduced pressure, and ethyl acetate was added to the concentrate. Washing was performed sequentially with water and saturated brine, followed by drying over sodium sulfate. The reaction mixture was subjected to filtration, concentration under reduced pressure, and purification by silica gel column chromatography (n-hexane/ethyl acetate=10/1), whereby a colorless oil was obtained (17.03 g, 57.80 mmol, 51.6%).

$^1$H-NMR (270 MHz, CDCl$_3$) δ: 1.46 (s, 9H), 1.58 (s, 6H), 3.89 (s, 3H), 6.83 (dd, J=8, 3 Hz, 1H), 7.30 (t, J=8 Hz, 1H), 7.52 (dd, J=3, 2 Hz, 1H), 7.65 (dt, J=8, 1 Hz, 1H).

Production Example 27

Synthesis of 3-(1-tert-Butoxycarbonyl-1-methylethoxy)benzoic Acid

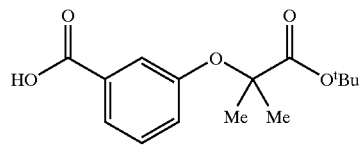

tert-Butyl 2-(3-methoxycarbonylphenoxy)-2-methylpropionate (17.03 g, 57.80 mmol) was dissolved in methanol (80 mL). Subsequently, an aqueous 3M sodium hydroxide solution (40 mL) was added thereto, and the mixture was stirred for three hours at room temperature. After completion of reaction, the mixture was acidified with hydrochloric acid under ice-cooling, to thereby precipitate colorless crystals. The crystals were subjected to filtration, thorough washing with water, and drying under reduced pressure, whereby colorless crystals were obtained (14.92 g, 53.22 mmol, 92.0%).

$^1$H-NMR (270 MHz, CDCl$_3$) δ: 1.46 (s, 9H), 1.60 (s, 6H), 7.13 (dd, J=8,3 Hz, 1H), 7.35 (t, J=8 Hz, 1H), 7.58 (s, 1H), 7.73 (d, J=8 Hz, 1H).

Production Example 28

Synthesis of tert-Butyl 2-(3-Allyloxycarbonylphenoxy)-2-methylpropionate

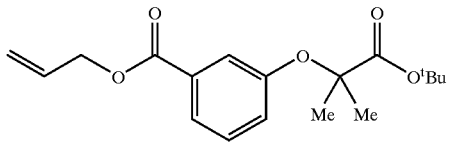

3-(1-tert-Butoxycarbonyl-1-methylethoxy)benzoic acid (14.92 g, 53.22 mmol) was dissolved in acetonitrile (60 mL). Subsequently, diisopropylamine (8.25 g, 63.87 mmol) was added thereto. Thereafter, allyl bromide (12.87 g, 106.45 mmol) was added dropwise, and the mixture was stirred for five hours at room temperature. Ethyl acetate was added for extraction. Washing was performed sequentially with water and saturated brine, followed by drying over magnesium sulfate. The reaction mixture was subjected to filtration, concentration under reduced pressure, and purification by silica gel column chromatography (n-hexane/ethyl acetate= 10/1), whereby a colorless oil was obtained (11.59 g, 36.19 mmol, 67.9%).

$^1$H-NMR (270 MHz, CDCl$_3$) δ: 1.45 (s, 9H), 1.59 (s, 6H), 4.80 (d, J=6 Hz, 2H), 5.28 (d, J=11 Hz, 1H), 5.39 (d, J=17 Hz, 1H), 5.97–6.05 (m, 1H), 7.07 (dd, J=8, 3 Hz, 1H), 7.31 (t, J=8 Hz, 1H), 7.54 (s, 1H), 7.68 (d, J=8 Hz, 1H).

Production Example 29

Synthesis of 2-(3-Allyloxycarbonylphenoxy)-2-methylpropionic Acid

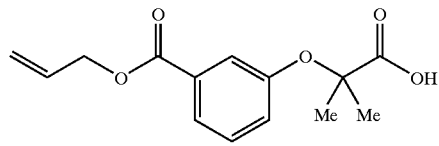

tert-Butyl 2-(3-allyloxycarbonylphenoxy)-2-methylpropionate (11.59 g, 36.19 mmol) was dissolved in dichloromethane (20 mL). Subsequently, trifluoroacetic acid (40 mL) was added at room temperature, and the mixture was stirred for three hours. The reaction mixture was concentrated under reduced pressure, and toluene was added to the concentrate. The resultant mixture was concentrated again under reduced pressure. Ethyl acetate was added. Washing was performed sequentially with water and saturated brine, followed by drying over sodium sulfate. The reaction mixture was subjected to filtration, concentration under reduced pressure, and purification by silica gel column chromatography (chloroform/methanol=10/1), whereby a yellow oil was obtained (8.30 g, 31.41 mmol, 86.7%).

$^1$H-NMR (270 MHz, CDCl$_3$) δ: 1.64 (s, 6H), 4.80 (d, J=6 Hz, 2H), 5.28 (d, J=10 Hz, 1H), 5.40 (d, J=17 Hz, 1H), 5.97–6.05 (m, 1H), 7.07 (dd, J=8, 3 Hz, 1H), 7.31 (t, J=8 Hz, 1H), 7.54 (s, 1H), 7.68 (d, J=8 Hz, 1H).

Production Example 30

Synthesis of 2-(3-Allyloxycarbonylphenoxy)-2-methylpropionic Acid Wang Resin Ester

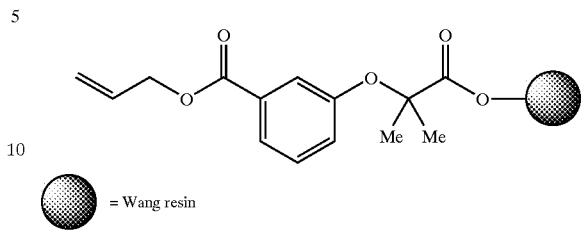

2-(3-Allyloxycarbonylphenoxy)-2-methylpropionic acid (8.30 g, 31.41 mmol) and triphenylphosphine (21.96 g, 83.75 mmol) were dissolved in tetrahydrofuran (200 mL). Thereafter, a Wang resin was added to the resultant mixture (1.1 mmol/g, 200–400 mesh, 19.03 g, 20.94 mmol) for swelling the resin. Subsequently, under argon atmosphere and under ice-cooling, diethyl azodicarboxylate (DEAD, 40% in toluene, 36.29 mL, 83.75 mmol) was added dropwise. After one hour, the temperature of the mixture was returned to room temperature, and the mixture was stirred overnight. The resin was collected through filtration and transferred to an Erlenmeyer flask, followed by addition of dimethylformamide and stirring for 15 minutes. The same procedure was performed three times. Thereafter, by use of dichloromethane, the same procedure was repeated. The resultant mixture was washed three times with methanol, then twice with diethyl ether, followed by drying under reduced pressure. The resin was allowed to swell in dichloromethane (200 mL). Diisopropylamine (5.95 g, 46.06 mmol) was added, and subsequently acetic anhydride (4.27 g, 41.88 mmol) was added. The mixture was stirred overnight at room temperature under argon atmosphere. Washing was performed three times with dichloromethane and with methanol, followed by drying under reduced pressure at room temperature. (23.36 g, increased in an amount of 4.33 g). The resin (100 mg) was treated with 50% trifluoroacetic acid in dichloromethane, subjected to toluene azeotrope, and dried sufficiently. From the thus-obtained 2-(3-allyloxycarbonylphenoxy)-2-methylpropionic acid (23 mg, 0.087 mmol), the amount of the compound incorporated into the resin was estimated to be 0.87 mmol/g (percent incorporation: 79.1%).

Production Example 31

Synthesis of 3-[1-(Wang Resin-oxycarbonyl)-1-methylethoxy]benzoic Acid

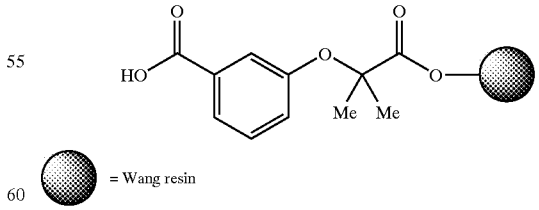

Triphenylphosphine (4.57 g, 17.43 mmol) was dissolved in tetrahydrofuran (200 mL). The resin prepared in Production Example 30 (22.26 g, 19.37 mmol) was added for swelling the resin. Subsequently, under argon atmosphere, tetrakis(triphenylphosphine)palladium (6.71 g, 5.81 mmol)

was added thereto, and the resultant mixture was made homogeneous. Thereafter, piperidine (49.47 g, 580.98 mmol) was added thereto, and the resultant mixture was stirred overnight at room temperature. The resin was collected through filtration and transferred to an Erlenmeyer flask, followed by addition of dimethylformamide and stirring for 15 minutes. The same procedure was performed three times. Thereafter, by use of dichloromethane, the same procedure was repeated. The resultant mixture was washed three times with methanol, followed by drying under reduced pressure at room temperature, whereby the target compound was obtained (22.10 g).

Production Example 32

Synthesis of 2-[3-(N-Cyclohexylmethylaminocarbonyl)phenoxy]-2-methylpropionic Acid Wang Resin Ester

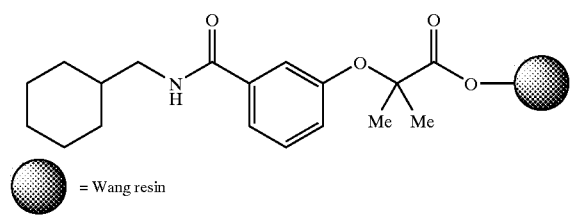

The resin prepared in Production Example 31 (0.87 mmol/g, 300 mg, 0.261 mmol) was added to dimethylformamide (3 mL), to thereby cause swelling of the resin. Thereafter, HOBt (353 mg, 2.610 mmol), cyclohexylmethylamine (2.610 mmol), and diisopropylethylamine (337 mg, 2.610 mmol) were added. Lastly, diisopropylcarbodiimide [DIC (329 mg, 2.610 mmol)] was added, and the resultant mixture was stirred overnight at room temperature. The reaction mixture was sequentially washed with dimethylformamide (three times), dichloromethane (three times), methanol (three times), and diethyl ether (three times), for five minutes each time.

Production Example 33

Synthesis of 2-[3-[(N-Cyclohexylmethyl)aminomethyl]phenoxy]-2-methylpropionic Acid Wang Resin Ester

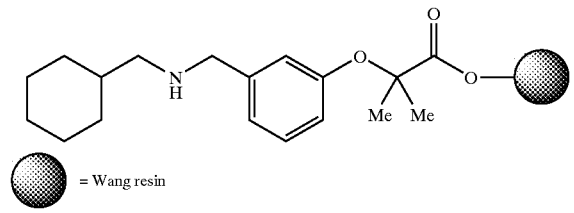

Tetrahydrofuran (1 mL) and then borane-tetrahydrofuran complex in tetrahydrofuran solution [BH$_3$-THF in THF (1.08 M, 6 mL)] were added to the resin prepared in Production Example 32, and the resultant mixture was stirred under nitrogen atmosphere for 2.5 hours at 50° C. The temperature of the mixture was returned to room temperature. Methanol was added to the reaction mixture, and the mixture was washed three times. Thereafter, the resultant mixture was sequentially washed with methanol (three times), dimethylformamide (three times), dichloromethane (three times), methanol (three times), diethyl ether (three times), for five minutes each time.

Production Example 34

Synthesis of 2-[3-[[N-(Benzoxazol-2-yl)-N-cyclohexylmethyl]aminomethyl]phenoxy]-2-methylpropionic Acid Wang Resin Ester

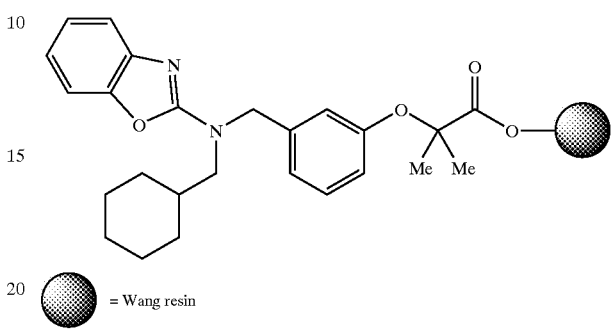

Dimethylformamide (4 mL) and then diisopropylethylamine (337 mg, 2.610 mmol) were added to the resin prepared in Production Example 33. Subsequently, 2-chlorobenzoxazole (801 mg, 5.22 mmol) was added thereto, the mixture was stirred overnight at 50° C. The resultant mixture was sequentially washed with dimethylformamide (three times), dichloromethane (three times), methanol (three times), diethyl ether (three times), for five minutes each time.

Example 134

Synthesis of 2-[3-[[N-(Benzoxazol-2-yl)-N-(cyclohexylmethyl)]aminomethyl]phenoxy]-2-methylpropionic Acid

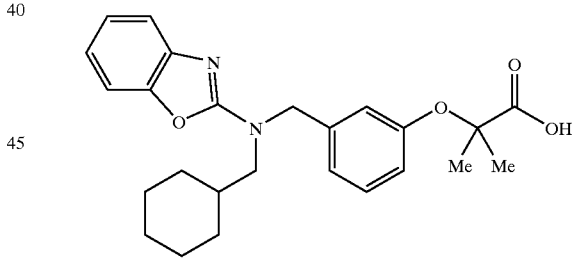

50% Trifluoroacetic acid in dichloromethane (5 mL) was added to the resin prepared in Production Example 34, and the mixture was stirred for 30 minutes at room temperature. The reaction mixture was collected. Subsequently, dichloromethane (5 mL) was added thereto, and the resultant mixture was stirred for five minutes. Thereafter, the mixture was subjected to concentration under reduced pressure, toluene azeotrope, thorough drying, and purification by preparative TLC (silica gel, chloroform/methanol=10/1), whereby the target compound was obtained (18.7% from Production Example 30).

MS (m/z) 422 (M$^+$).

In a manner similar to that described in Example 134, the compounds of Example 135 through Example 154 were synthesized.

Example 135

2-[3-[[N-(Benzoxazol-2-yl)-N-(naphth-1-ylmethyl)]aminomethyl]phenoxy]-2-methylpropionic Acid

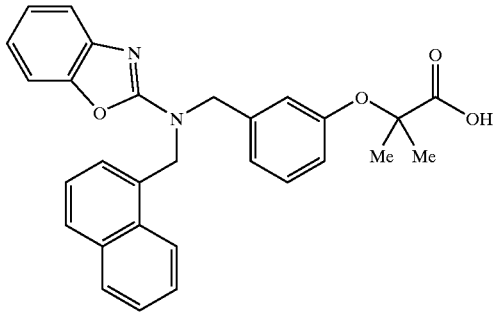

MS (m/z) 466 (M+).

Example 136

2-[3-[[N-(Benzoxazol-2-yl)-N-n-pentyl]aminomethyl]phenoxy]-2-methylpropionic Acid

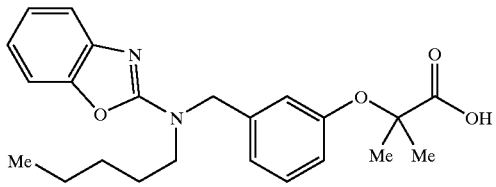

MS (m/z) 396 (M+).

Example 137

2-[3-[[N-(Benzoxazol-2-yl)-N-(3-methylbutyl)]aminomethyl]phenoxy]-2-methylpropionic Acid

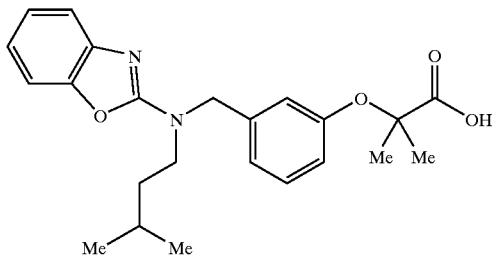

MS (m/z) 396 (M+).

Example 138

2-[3-[[N-(Benzoxazol-2-yl)-N-n-heptyl]aminomethyl]phenoxy]-2-methylpropionic Acid

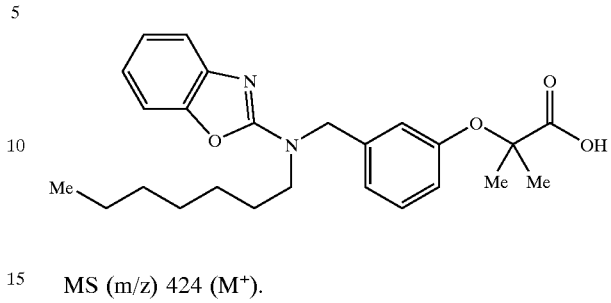

MS (m/z) 424 (M+).

Example 139

2-[3-[[N-(Benzoxazol-2-yl)-N-methyl]aminomethyl]phenoxy]-2-methylpropionic Acid

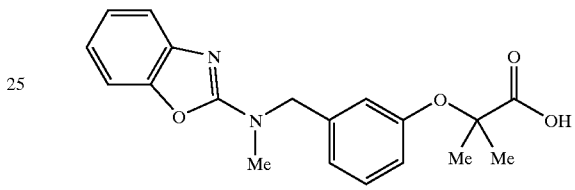

MS (m/z) 340 (M+).

Example 140

2-[3-[[N-(Benzoxazol-2-yl)-N-ethyl]aminomethyl]phenoxy]-2-methylpropionic Acid

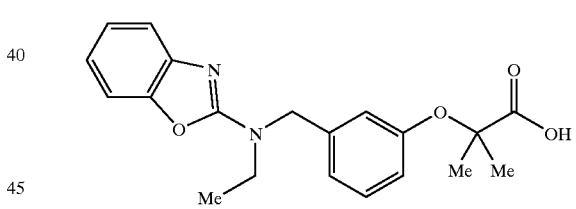

MS (m/z) 354 (M+).

Example 141

2-[4-[[N-(Benzoxazol-2-yl)-N-methyl]aminomethyl]phenoxy]-2-methylpropionic Acid

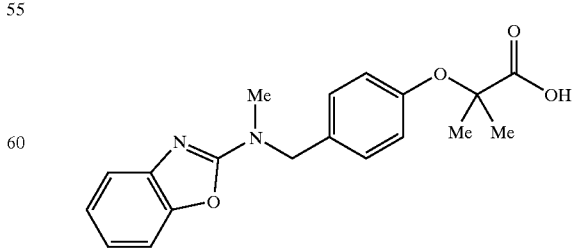

MS (m/z) 341 (M++1) FAB.

Example 142

2-[4-[[N-(Benzoxazol-2-yl)-N-ethyl]aminomethyl]phenoxy]-2-methylpropionic Acid

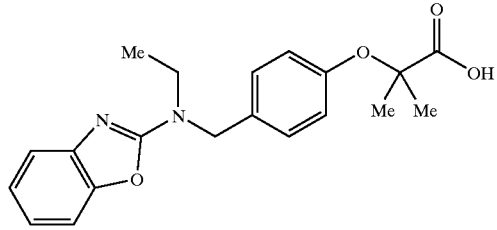

MS (m/z) 354 (M$^+$).

Example 143

2-[4-[[N-(Benzoxazol-2-yl)-N-n-propyl]aminomethyl]phenoxy]-2-methylpropionic Acid

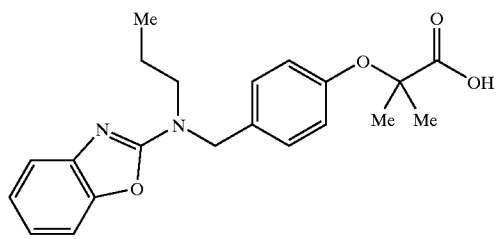

MS (m/z) 368 (M$^+$).

Example 144

2-[4-[[N-(Benzoxazol-2-yl)-N-n-butyl]aminomethyl]phenoxy]-2-methylpropionic Acid

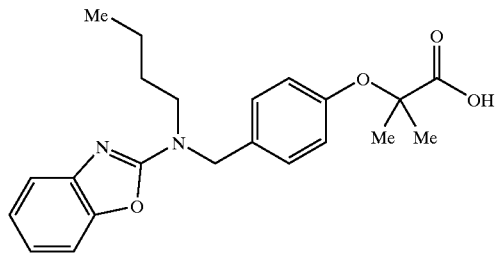

MS (m/z) 382 (M$^+$).

Example 145

2-[4-[[N-(Benzoxazol-2-yl)-N-n-pentyl]aminomethyl]phenoxy]-2-methylpropionic Acid

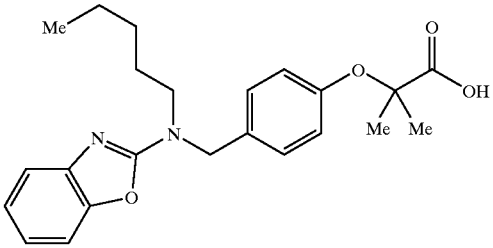

MS (m/z) 396 (M$^+$).

Example 146

2-[4-[[N-(Benzoxazol-2-yl)-N-(3-methylbutyl)]aminomethyl]phenoxy]-2-methylpropionic Acid

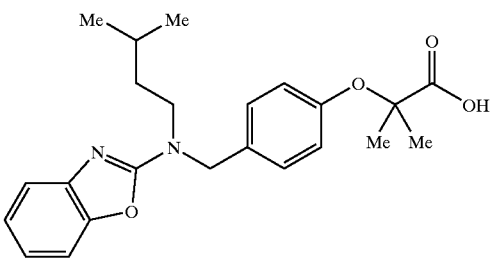

MS (m/z) 396 (M$^+$).

Example 147

2-[4-[[N-(Benzoxazol-2-yl)-N-n-hexyl]aminomethyl]phenoxy]-2-methylpropionic Acid

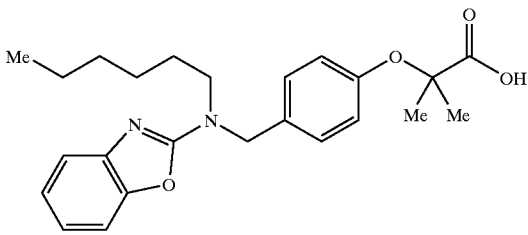

MS (m/z) 410 (M$^+$).

Example 148

2-[4-[[N-(Benzoxazol-2-yl)-N-n-heptyl]aminomethyl]phenoxy]-2-methylpropionic Acid

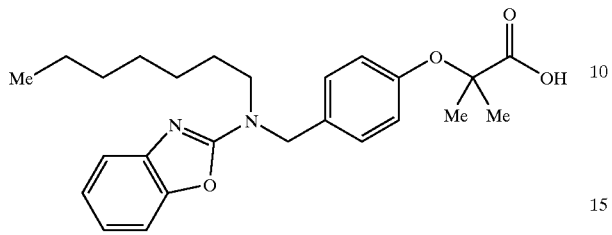

MS (m/z) 424 (M+).

Example 149

2-[4-[[N-(Benzoxazol-2-yl)-N-n-octyl]aminomethyl]phenoxy]-2-methylpropionic Acid

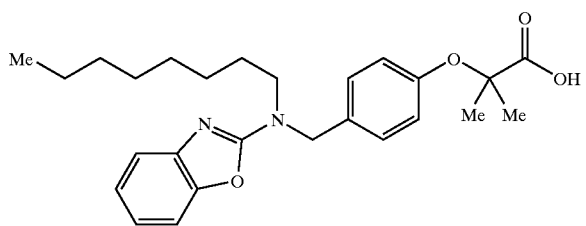

MS (m/z) 438 (M+).

Example 150

2-[4-[[N-(Benzoxazol-2-yl)-N-cyclopropylmethyl]aminomethyl]phenoxy]-2-methylpropionic Acid

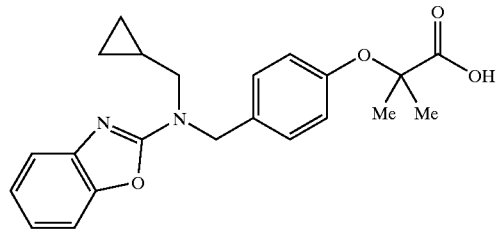

MS (m/z) 380 (M+).

Example 151

2-[4-[[N-(Benzoxazol-2-yl)-N-(3-phenylpropyl)]aminomethyl]phenoxy]-2-methylpropionic Acid

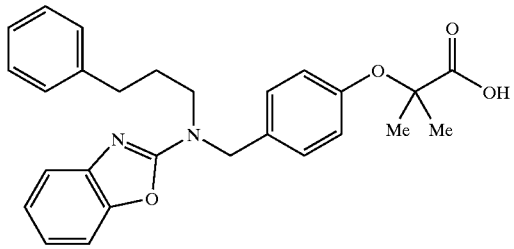

MS (m/z) 444 (M+).

Example 152

2-[4-[[N-(Benzoxazol-2-yl)-N-(3-cyclohexylpropyl)]aminomethyl]phenoxy]-2-methylpropionic Acid

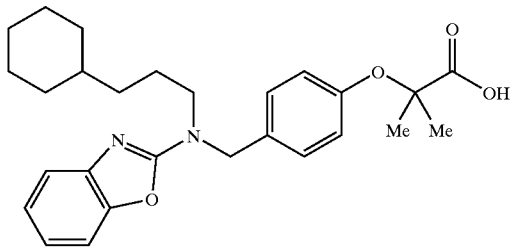

MS (m/z) 450 (M+).

Example 153

2-[4-[[N-(Benzoxazol-2-yl)-N-(4-methylpentyl)]aminomethyl]phenoxy]-2-methylpropionic Acid

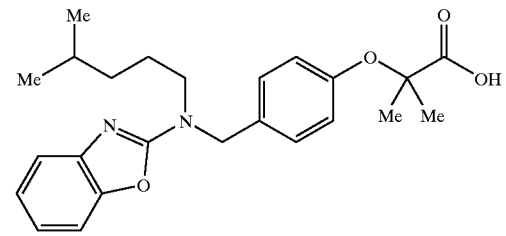

MS (m/z) 410 (M+).

Example 154

2-[4-[[N-(2-Aminobenzyl)-N-(benzoxazol-2-yl)]aminomethyl]phenoxy]-2-methylpropionic Acid

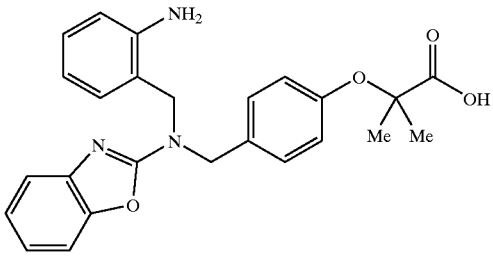

MS (m/z) 431 (M+).

Production Example 35

Synthesis of 3-(2-Methoxyphenyl)propionamide

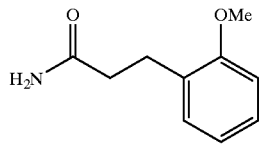

3-(2-methoxyphenyl)propionic acid (9.0 g, 49.9 mmol) was dissolved in acetonitrile (10 mL). Subsequently, pyridine (3.54 g, 44.9 mmol) and di-tert-butyl dicarbonate [$Boc_2O$ (16.3 g, 74.85 mmol)] were added thereto. The mixture was stirred for 10 minutes at room temperature, and then ammonium hydrogencarbonate (5.92 g, 74.9 mmol) were added. After completion of reaction, the reaction mixture was concentrated under reduced pressure. Thereafter, the resultant concentrate was added to water, and the resultant mixture was extracted with chloroform, followed by washing sequentially with 1M hydrochloric acid and saturated brine. The resultant mixture was subjected to drying over magnesium sulfate and concentration under reduced pressure. The resultant concentrate was used in Production Example 36 without purification.

Production Example 36

Synthesis of 3-(2-Hydroxyphenyl)propionamide

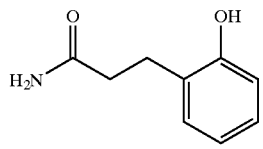

The compound prepared in Production Example 35 was dissolved in methylene chloride. Subsequently, 1.0M boron tribromide in methylene chloride solution (78.8 mL, 78.8 mmol) was added dropwise under ice-cooling. The temperature of the mixture was allowed to room temperature, followed by stirring for three hours. Water was added thereto, and the mixture was extracted with chloroform, followed by washing with saturated brine. The resultant mixture was subjected to drying over sodium sulfate, concentration under reduced pressure, and purification by column chromatography (chloroform/methanol=20/1), whereby the target compound was obtained (6.01 g, 92%).

$^1$H NMR (400 MHz, $CDCl_3$) δ 2.64 (t, J=6 Hz, 2H), 2.90 (t, J=6 Hz, 2H), 5.67 (br.s, 1H), 5.88 (br.s, 1H), 6.84 (t, J=7 Hz, 1H), 6.89 (d, J=8 Hz, 1H), 7.05 (d, J=8 Hz, 1H), 7.11 (t, J=7 Hz, 1H), 8.50 (br.s, 1H).

Production Example 37

Synthesis of tert-Butyl 2-[2-(2-Aminocarbonylethyl)phenoxy]-2-methylpropionate

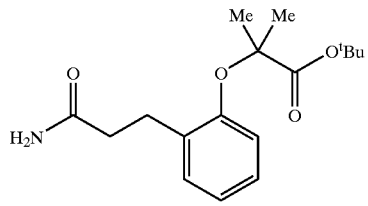

3-(2-Hydroxyphenyl)propionamide (5.6 g, 33.9 mmol) was dissolved in acetonitrile (15 mL), and potassium carbonate (18.7 g, 135 mmol) was added thereto. Subsequently, tert-butyl 2-bromoisobutyrate (30.3 g, 135 mmol) was added, and the mixture was stirred at 80° C. After completion of reaction, water was added thereto, and the resultant mixture was extracted with ethyl acetate. The organic layer was washed with saturated brine, followed by drying over sodium sulfate, concentration under reduced pressure, and purification by silica gel chromatography (chloroform/methanol=40/1), whereby the target compound was obtained (2.67 g, 26%).

Production Example 38

Synthesis of tert-Butyl 2-[2-(3-Aminopropyl)phenoxy]-2-methylpropionate

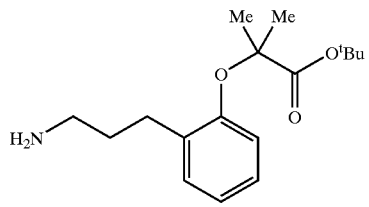

tert-Butyl 2-[2-(2-aminocarbonylethyl)phenoxy]-2-methylpropionate (2.7 g, 8.68 mmol) was dissolved in tetrahydrofuran (5 mL). Subsequently, under nitrogen atmosphere, borane-tetrahydrofuran complex in tetrahydrofuran solution [1.0M $BH_3$-THF in THF (26.1 mL, 26.1 mmol)] was added thereto, the mixture was stirred for three hours at 50° C. Thereafter, concentrated hydrochloric acid was gradually added thereto at 0° C. The resultant mixture was stirred for one hour at room temperature and made basic with an aqueous ethylamine solution. Ethyl acetate was added thereto. The mixture was sequentially washed with water and saturated brine, followed by drying over sodium sulfate, concentration under reduced pressure, and purification by silica gel column chromatography (chloroform/methanol=30/1), whereby the target compound was obtained (1.44 g, 4.91 mmol, 57%).

$^1$H NMR (400 MHz, $CDCl_3$) δ 1.41 (s, 9H), 1.59 (s, 6H), 1.75 (quintet, J=7 Hz, 2H), 2.66 (t, J=7 Hz, 2H), 2.71 (t, J=7

Hz, 2H), 6.68 (d, J=8 Hz, 1H), 6.87 (t, J=7 Hz, 1H), 7.04 (t, J=8 Hz, 1H), 7.12 (d, J=7 Hz, 1H).

Production Example 39

Synthesis of tert-Butyl 2-[2-[3-(N-Benzoxazol-2-yl)aminopropyl]phenoxy]-2-methylpropionate

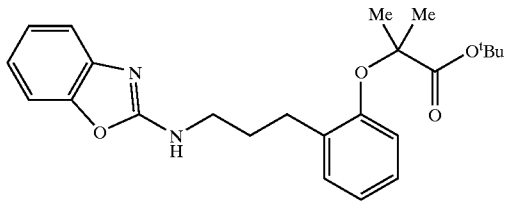

tert-Butyl 2-[2-(3-aminopropyl)phenoxy]-2-methylpropionate (1.44 g, 4.9 mmol) was dissolved in tetrahydrofuran (5 mL). Subsequently, diisopropylethylamine (762 mg, 5.9 mmol) and then 2-chlorobenzoxazole (904 mg, 5.9 mmol) were added thereto, and the mixture was stirred overnight at room temperature. Ethyl acetate was added thereto. The resultant mixture was sequentially washed with water and saturated brine, followed by drying over sodium sulfate, filtration, concentration under reduced pressure, and purification by silica gel column chromatography (n-hexane/ethyl acetate=6/1), whereby the target compound was obtained (2.03 g, q.).

$^1$H NMR (400 MHz, CDCl$_3$) δ 1.42 (s, 9H), 1.64 (s, 6H), 1.99 (quintet, J=7 Hz, 2H), 2.77 (t, J=7 Hz, 2H), 3.39–3.44 (m, 2H), 6.71 (d, J=8 Hz, 1H), 6.90 (t, J=8 Hz, 1H), 7.00 (t, J=8 Hz, 1H), 7.08 (t, J=8 Hz, 1H), 7.12–7.16 (m, 2H), 7.20 (d, J=8 Hz, 1H), 7.35 (d, J=8 Hz, 1H).

Production Example 40

Synthesis of tert-Butyl 2-[2-[3-[N-(Benzoxazol-2-yl)-N-n-octyl]aminopropyl]phenoxy]-2-methylpropionate

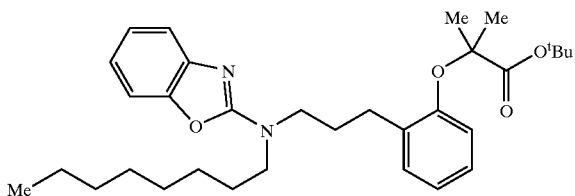

tert-Butyl 2-[2-[3-(N-benzoxazol-2-yl)aminopropyl]phenoxy]-2-methylpropionate (120 mg, 0.29 mmol) was dissolved in acetonitrile (2 mL). Subsequently, cesium carbonate (206 mg, 0.584 mmol) and n-octyl bromide (112 mg, 0.58 mmol) were added thereto, and the mixture was stirred overnight at 80° C. The temperature of the mixture was returned to room temperature, and ethyl acetate was added. The resultant mixture was sequentially washed with water and saturated brine, followed by drying over sodium sulfate, concentration under reduced pressure, purification by silica gel column chromatography (n-hexane/ethyl acetate=4/1), whereby the target compound was obtained (124 mg, 0.24 mmol, 82%).

Example 155

Synthesis of 2-[2-[3-[N-(Benzoxazol-2-yl)-N-n-octyl]aminopropyl]phenoxy]-2-methylpropionic Acid

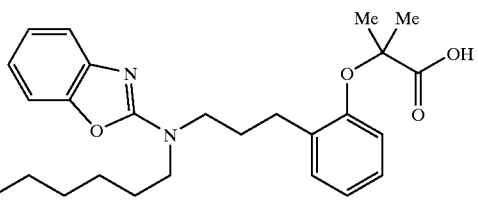

tert-Butyl 2-[2-[3-[N-(benzoxazol-2-yl)-N-n-octyl]aminopropyl]phenoxy]-2-methylpropionate (124 mg, 0.24 mmol) was dissolved in methylene chloride (1 mL). Subsequently, 50% trifluoroacetic acid in methylene chloride solution was added thereto, and the mixture was stirred for three hours at room temperature. The reaction mixture was concentrated under reduced pressure, and the resultant concentrate was subjected to toluene azeotrope. Thereafter, chloroform was added thereto, followed by washing sequentially with water and saturated brine, and drying over sodium sulfate. The resultant mixture was subjected to concentration under reduced pressure and purification by preparative TLC (silica gel, chloroform/methanol=20/1), whereby the target compound was obtained (79.7 mg, 0.17 mmol, 71%).

MS (m/z) 466 (M$^+$).

In a manner similar to that described in Example 155, the compounds of Example 156 through Example 168 were synthesized.

Example 156

2-[2-[2-[N-(Benzoxazol-2-yl)-N-(3-phenylpropyl)]aminoethyl]phenoxy]-2-methylpropionic Acid

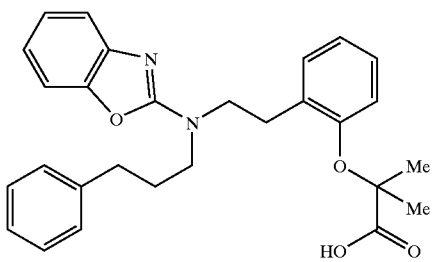

MS (m/z) 458 (M$^+$).

Example 157

2-[2-[2-[N-(Benzoxazol-2-yl)-N-n-propyl]aminoethyl]phenoxy]-2-methylpropionic Acid

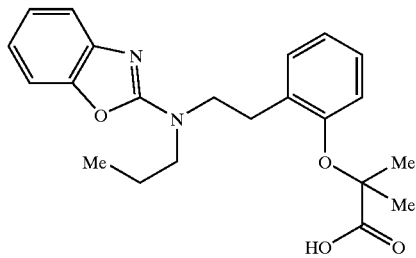

MS (m/z) 382 (M$^+$).

Example 158

2-[2-[2-[N-(Benzoxazol-2-yl)-N-isopropyl]aminoethyl]phenoxy]-2-methylpropionic Acid

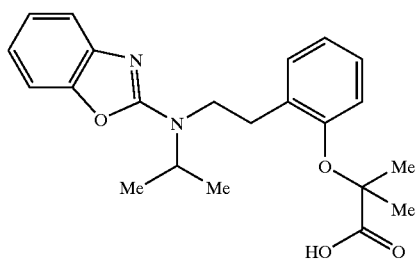

MS (m/z) 382 (M$^+$).

Example 159

2-[2-[2-[N-(Benzoxazol-2-yl)-N-n-octyl]aminoethyl]phenoxy]-2-methylpropionic Acid

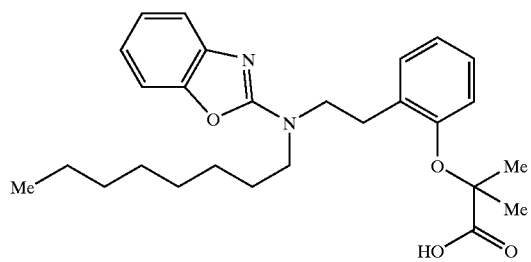

MS (m/z) 452 (M$^+$).

Example 160

2-[2-[2-[N-(Benzoxazol-2-yl)-N-(naphth-1-ylmethyl)]aminoethyl]phenoxy]-2-methylpropionic Acid

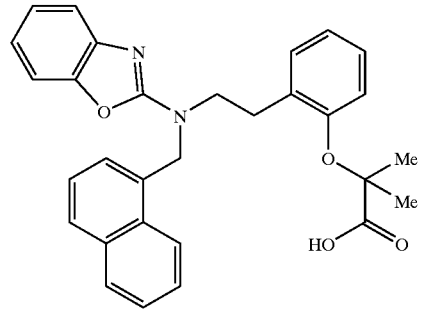

MS (m/z) 480 (M$^+$).

Example 161

2-[2-[2-[N-(Benzoxazol-2-yl)-N-(4-chlorobenzyl)]aminoethyl]phenoxy]-2-methylpropionic Acid

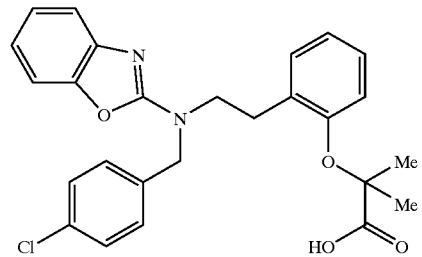

MS (m/z) 464, 466 (M$^+$).

Example 162

2-[2-[3-[N-(Benzoxazol-2-yl)-N-n-propyl]aminopropyl]phenoxy]-2-methylpropionic Acid

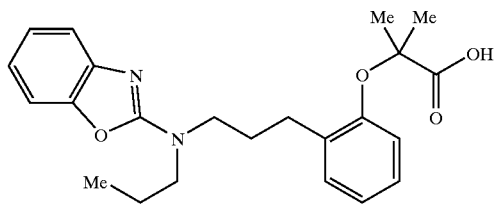

MS (m/z) 396 (M$^+$).

Example 163

2-[2-[3-[N-(Benzoxazol-2-yl)-N-(4-chlorobenzyl)]aminopropyl]phenoxy]-2-methylpropionic Acid

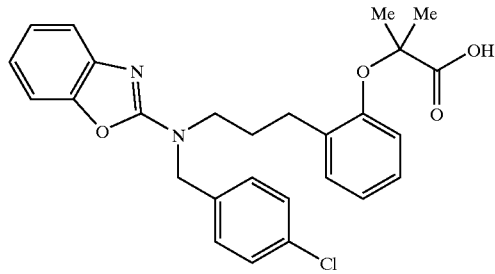

MS (m/z) 478, 480 (M⁺).

Example 164

2-[2-[3-[N-(Benzoxazol-2-yl)-N-isopropyl]aminopropyl]phenoxy]-2-methylpropionic Acid

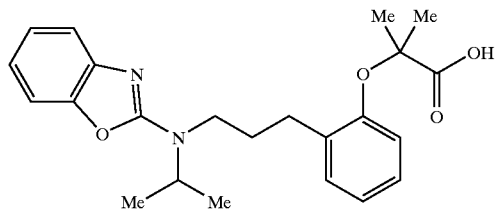

MS (m/z) 396 (M⁺).

Example 165

2-[2-[3-[N-(Benzoxazol-2-yl)-N-(naphth-1-ylmethyl)]aminopropyl]phenoxy]-2-methylpropionic Acid

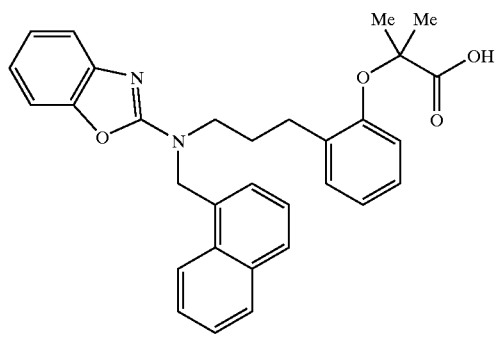

MS (m/z) 494 (M⁺).

Example 166

2-[2-[3-[N-(Benzoxazol-2-yl)-N-(3-phenylpropyl)]aminopropyl]phenoxy]-2-methylpropionic Acid

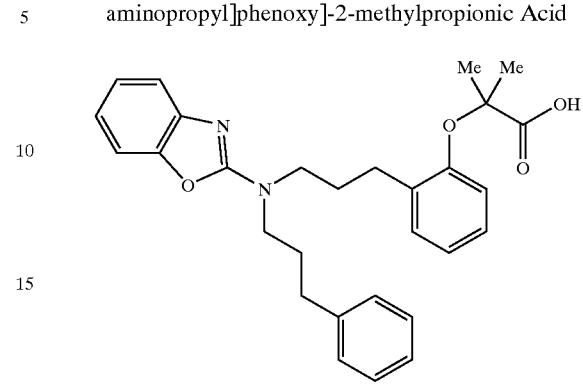

MS (m/z) 472 (M⁺).

Example 167

2-[2-[3-[N-(Benzoxazol-2-yl)-N-(4-fluorobenzyl)]aminopropyl]phenoxy]-2-methylpropionic Acid

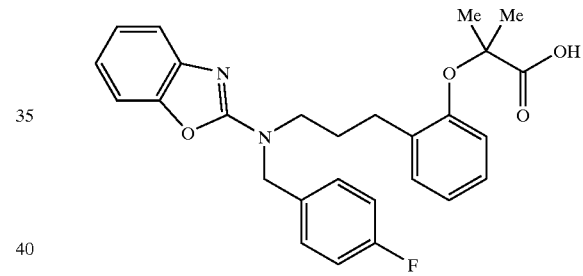

MS (m/z) 462 (M⁺).

Example 168

2-[2-[3-[N-(Benzoxazol-2-yl)-N-(2-nitrobenzyl)]aminopropyl]phenoxy]-2-methylpropionic Acid

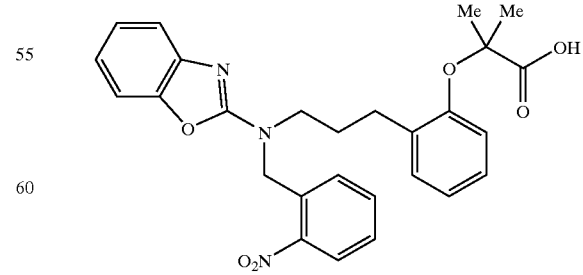

MS (m/z) 489 (M⁺).

Production Example 41

Synthesis of tert-Butyl 2-[3-(Allyloxycarbonylmethyl)phenoxy]-2-methylpropionate

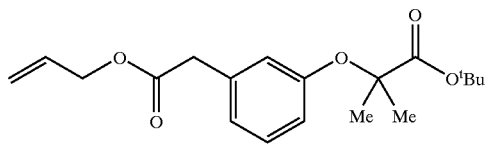

Allyl 3-hydroxyphenylacetate (7.63 g, 50.10 mmol), potassium carbonate (13.85 g, 100.3 mmol), and tert-butyl 2-bromoisobutyrate (30.37 g, 100.3 mmol) were dissolved in dimethylformamide (9 mL), and the mixture was stirred for 13 hours at 80° C. The reaction mixture was added to water, and the resultant mixture was extracted with diethyl ether, followed by washing sequentially with water and saturated brine. The mixture was subjected to drying over magnesium sulfate, concentration under reduced pressure, and purification by silica gel column chromatography (n-hexane/ethyl acetate=20/1), whereby the target compound was obtained (3.55 g, 10.62 mmol, 21.2%).

$^1$H NMR (400 MHz, CDCl$_3$) δ 1.43 (s, 9H), 1.55 (s, 6H), 3.57 (s, 2H), 4.58 (m, 2H), 5.30 (m, 2H), 5.90 (m, 1H), 6.76 (m, 1H), 6.80 (m, 1H), 6.90 (d, J=7 Hz, 1H), 7.17 (m, 1H).

Production Example 42

Synthesis of 3-(1-tert-Butoxycarbonyl-1-methylethoxy)phenylacetic Acid

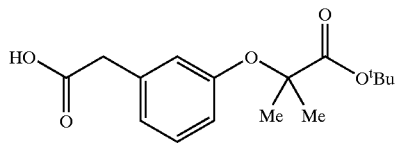

tert-Butyl 2-[3-(allyloxycarbonylmethyl)phenoxy]-2-methylpropionate (3.35 g, 10.62 mmol) was dissolved in methanol (40 mL) and tetrahydrofuran (40 mL). Subsequently, an aqueous 2M sodium hydroxide solution (40 mL) was added thereto, and the mixture was stirred for three hours at room temperature. The resultant mixture was concentrated under reduced pressure, and the resultant concentrate was acidified with 3M hydrochloric acid. The mixture was extracted with chloroform, followed by drying over sodium sulfate and concentration under reduced pressure, whereby the target compound was obtained (2.98 g, 10.12 mmol, 95.5%).

Production Example 43

Synthesis of tert-Butyl 2-[3-(aminocarbonylmethyl)phenoxy]-2-methylpropionate

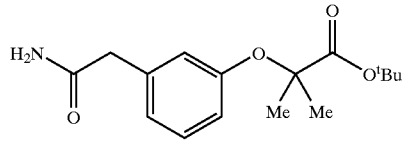

3-(1-tert-Butoxycarbonyl-1-methylethoxy)phenylacetic acid (2.0 g, 6.79 mmol) is dissolved in acetonitrile (15 mL). Subsequently, pyridine (0.34 mL, 4.22 mmol) and ammonium hydrogencarbonate (699 mg, 8.84 mmol) were added thereto, and the mixture was stirred for 10 minutes at room temperature. Thereafter, di-tert-butyl dicarbonate [Boc$_2$O (2.03 mL, 8.84 mmol)] was added thereto, and the resultant mixture was stirred for 14 hours. The reaction mixture was concentrated under reduced pressure. Thereafter, the resultant concentrate was added to water, and the mixture was extracted with chloroform, followed by washing sequentially with 1M hydrochloric acid and saturated brine. The resultant mixture was subjected to drying over magnesium sulfate, concentration under reduced pressure, and purification by silica gel column chromatography (chloroform/methanol=10/1), whereby the target compound was obtained (1.07 g, 3.65 mmol, 53.6%).

Production Example 44

Synthesis of tert-Butyl 2-[3-(2-Aminoethyl)phenoxy]-2-methylpropionate

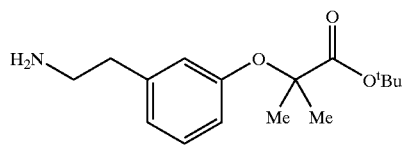

In a nitrogen atmosphere, tert-butyl 2-(3-aminocarbonylmethyl)phenoxy)-2-methylpropionate (1.07 g, 3.65 mmol) was dissolved in tetrahydrofuran. Subsequently, borane-tetrahydrofuran complex in tetrahydrofuran solution [1M BH$_3$-THF in THF (18.2 mL, 18.2 mmol)] was added thereto, and the mixture was stirred for one hour at 50° C. The resultant mixture was concentrated under reduced pressure, followed by addition of 1M hydrochloric acid at 0° C. and stirring at room temperature. The resultant mixture was made basic with sodium carbonate, extracted with chloroform, and dried over sodium sulfate. The reaction mixture was subjected to filtration, concentration under reduced pressure, and purification by silica gel column chromatography (CHCl$_3$/MeOH=10/1), whereby the target compound was obtained (990 mg, 3.94 mmol, >q.).

Production Example 45

Synthesis of tert-Butyl 2-[3-[2-(4-Methylpentylamido)ethyl]phenoxy]-2-methylpropionate

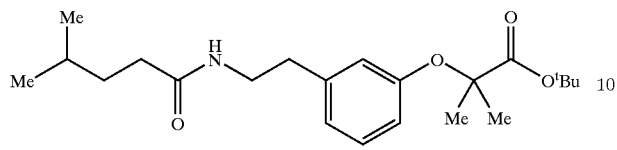

tert-Butyl 2-[3-(2-aminoethyl)phenoxy]-2-methylpropionate (280 mg, 1.00 mmol) was dissolved in dichloromethane (2 mL), and dicyclohexylcarbodiimide (252 mg, 1.22 mmol) was added thereto. Subsequently, 4-methyl pentanoic acid (154 μL, 1.22 mmol) was added dropwise at room temperature, and the mixture was stirred overnight, followed by filtration with Celite. Water was added to the resultant filtrate, and the resultant mixture was extracted with chloroform, followed by washing with diluted hydrochloric acid. The organic layer was washed with saturated brine, followed by drying over sodium sulfate, concentration under reduced pressure, and purification by silica gel chromatography (chloroform/methanol=50/1), whereby the target compound was obtained (284 mg, 0.752 mmol, 75.2%).

Production Example 46 tert-Butyl 2-[3-[2-(N-4-methylpentyl)aminoethyl]phenoxy]-2-methylpropionate

In a nitrogen atmosphere, tert-butyl 2-[3-[2-(4-methylpentylamido)ethyl]phenoxy]-2-methylpropionate (284 mg, 0.752 mmol) was dissolved in tetrahydrofuran (5 mL). Subsequently, borane-tetrahydrofuran complex in tetrahydrofuran solution [1M BH$_3$-THF in THF (5.1 mL, 5.1 mmol)] was added thereto, and the mixture was stirred for one hour at 50° C. The reaction mixture was concentrated under reduced pressure, and 1M hydrochloric acid was added at 0° C., and the resultant mixture was stirred at room temperature. The mixture was made basic with sodium carbonate, followed by extraction with chloroform and drying over sodium sulfate. The reaction mixture was subjected to filtration, concentration under reduced pressure, and purification by silica gel column chromatography (chloroform/methanol=10/1), whereby the target compound was obtained (81.5 mg, 0.223 mmol, 29.6%).

$^1$H NMR (400 MHz, CDCl$_3$) δ 0.84 (d, J=7 Hz, 6H), 1.10–1.16 (m, 2H), 1.41 (s, 9H), 1.41–1.51 (m, 2H), 1.53 (s, 6H), 1.91 (br.s, 1H), 2.57 (t, J=7 Hz, 2H), 2.73 (t, J=7 Hz, 2H), 2.83 (t, J=7 Hz, 2H), 6.66 (d, J=8 Hz, 1H), 6.70 (s, 1H), 6.79 (d, J=8 Hz, 1H), 7.11 (t, J=8 Hz, 1H).

Production Example 47

Synthesis of tert-Butyl 2-[3-[2-[N-(Benzoxazol-2-yl)-N-(4-methylpentyl)]aminoethyl]phenoxy]-2-methylpropionate

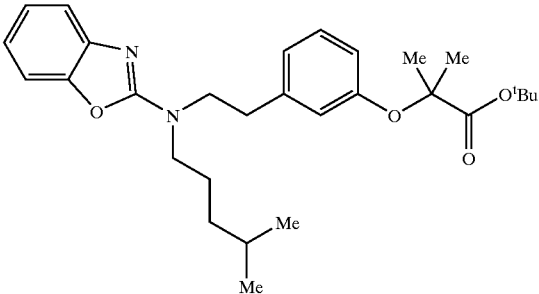

tert-Butyl 2-[3-[2-(N-4-methylpentyl)aminoethyl]phenoxy]-2-methylpropionate (45 mg, 0.125 mmol) was dissolved in acetonitrile (2 mL). Subsequently, cesium carbonate (61 mg, 0.188 mmol) and then 2-chlorobenzoxazole (24.5 μL, 0.188 mmol) were added thereto, and the mixture was stirred under argon atmosphere overnight at 70° C. Ethyl acetate was added to the reaction mixture, followed by washing with water and saturated brine and drying over sodium sulfate. The reaction mixture was subjected to filtration, concentration under reduced pressure, and purification by preparative TLC (silica gel, n-hexane/ethyl acetate=10/1), whereby the target compound was obtained (53 mg, 0.110 mmol, 88.4%).

Example 169

Synthesis of 2-[3-[2-[N-(benzoxazol-2-yl)-N-(4-methylpentyl)]aminoethyl]phenoxy]-2-methylpropionic Acid

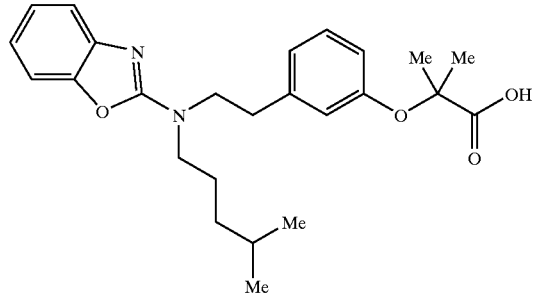

tert-Butyl 2-[3-[2-[N-(benzoxazol-2-yl)-N-(4-methylpentyl)]aminoethyl]phenoxy]-2-methylpropionate (53 mg, 0.110 mmol) was dissolved in dichloromethane (3 mL). Subsequently, trifluoroacetic acid (0.5 mL) was added thereto, and the mixture was stirred at room temperature. After completion of reaction, the resultant mixture was subjected to toluene azeotrope, followed by purification by preparative TLC (silica gel, chloroform/methanol=10/1), whereby the target compound was obtained (47 mg, 0.111 mmol, >q.).

$^1$H NMR (400 MHz, CDCl$_3$) δ 0.86 (br.s, 6H), 1.16 (br.s, 2H), 1.51 (s, 6H), 1.60 (br.s, 3H), 2.90 (br.s, 2H), 3.38 (t, J=7 Hz, 2H), 3.76 (br.s, 2H), 6.75 (br.s, 2H), 6.88 (br.s, 1H), 7.08–7.25 (m, 4H), 7.43 (d, J=8 Hz, 1H).

Production Example 48

Synthesis of Ethyl 2-[3-(Allyloxycarbonylmethyl) phenoxy]-2-methylpropionate

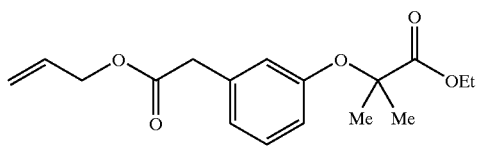

Allyl 3-hydroxyphenylacetate (5.72 g, 32.9 mmol), potassium carbonate (6.82 g, 49.35 mmol), and ethyl 2-bromoisobutyrate (7.35 mL, 49.35 mmol) were dissolved in dimethylformamide (10 mL), and the mixture was stirred for 60 hours at 80° C. The reaction mixture was added to water, and the resultant mixture was extracted with diethyl ether, followed by washing sequentially with water and saturated brine, drying over magnesium sulfate, concentration under reduced pressure, and purification by silica gel column chromatography (n-hexane/ethyl acetate=20/1), whereby the target compound was obtained (6.40 g, 20.90 mmol, 63.5%).

Production Example 49

Synthesis of 3-(1-Ethoxycarbonyl-1-methylethoxy) phenylacetic Acid

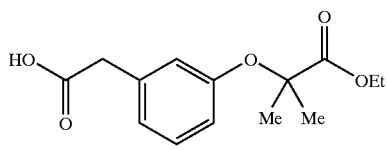

Ethyl 2-[3-(allyloxycarbonylmethyl)phenoxy]-2-methylpropionate (6.40 g, 20.9 mmol) was dissolved in tetrahydrofuran (150 mL). Subsequently, triphenylphosphine (2.42 g, 2.09 mmol) and piperidine (41.34 mL, 41.8 mmol) were added thereto. Under argon atmosphere, tetrakis(triphenylphosphine)palladium (2.42 g, 2.09 mmol) was added, the resultant mixture was stirred for three hours at room temperature. After completion of reaction, the reaction mixture was concentrated under reduced pressure, followed by addition of chloroform and washing sequentially with 3M hydrochloric acid, water, and saturated brine. The resultant mixture was subjected to drying over sodium sulfate, concentration under reduced pressure, and purification by silica gel column chromatography (chloroform/methanol/acetic acid=50/1/0.5), whereby the target compound was obtained (6.88 g, 25.84 mmol, >q.).

Production Example 50

Synthesis of Ethyl 2-(3-Aminocarbonylmethylphenoxy)-2-methylpropionate

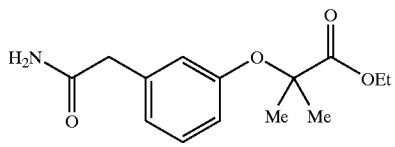

3-(1-Ethoxycarbonyl-1-methylethoxy)phenylacetic acid (532 mg, 0.2 mmol) was dissolved in acetonitrile (3 mL). Subsequently, pyridine (0.1 mL, 1.24 mmol) and ammonium hydrogencarbonate (206 mg, 2.6 mmol) were added thereto, and the mixture was stirred for 10 minutes at room temperature. Thereafter, di-tert-butyl dicarbonate [$Boc_2O$ (597.2 mL, 2.6 mmol)] was added thereto, and the mixture was stirred for 14 hours. The reaction mixture was concentrated under reduced pressure, and the resultant concentrate was added to water, followed by extraction with chloroform. Subsequently, washing was performed sequentially with 1M hydrochloric acid and saturated brine. The resultant mixture was subjected to drying over magnesium sulfate, concentration under reduced pressure, and purification by silica gel column chromatography (chloroform/methanol=10/1), whereby the target compound was obtained (524 mg, 0.198 mmol, 98.8%).

Production Example 51

Synthesis of Ethyl 2-[3-(2-Aminoethyl)phenoxy]-2-methylpropionate

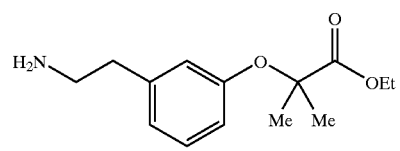

Under nitrogen atmosphere, ethyl 2-(3-aminocarbonylmethylphenoxy)-2-methylpropionate (507 mg, 1.91 mmol) was dissolved in tetrahydrofuran. Subsequently, borane-tetrahydrofuran complex in tetrahydrofuran solution [1M $BH_3$-THF in THF (19.1 mL, 19.1 mmol)] was added thereto, and the mixture was stirred for one hour at 50° C. The reaction mixture was concentrated under reduced pressure, followed by addition of 1M hydrochloric acid at 0° C. and stirring at room temperature. The resultant mixture was made basic with sodium carbonate, followed by extraction with chloroform and drying over sodium sulfate. The reaction mixture was subjected to filtration, concentration under reduced pressure, and purification by silica gel column chromatography (chloroform/methanol=10/1), whereby the target compound was obtained (261.8 mg, 1.04 mmol, 54.5%)

$^1$H NMR (400 MHz, $CDCl_3$) δ 1.17 (t, J=7 Hz, 3H), 1.52 (s, 6H), 2.64 (t, J=7 Hz, 2H), 2.85 (t, J=7 Hz, 2H), 3.13 (br.s, 2H), 4.16 (q, J=7 Hz, 2H), 6.59 (d, J=8 Hz, 1H), 6.63 (s, 1H), 6.73 (d, J=8 Hz, 1H), 7.07 (t, J=8 Hz, 1H).

Production Example 52

Synthesis of Ethyl 2-[3-[2-(N-Benzoxazol-2-yl) aminoethyl]phenoxy]-2-methylpropionate

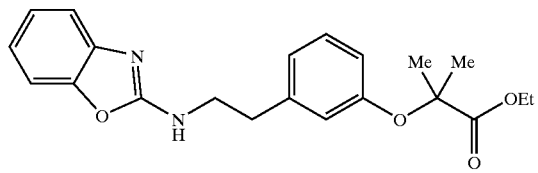

Ethyl 2-[3-(2-aminoethyl)phenoxy]-2-methylpropionate (1.1 g, 4.38 mmol) was dissolved in tetrahydrofuran (22 mL). Subsequently, diisopropylethylamine (1.14 mL, 6.57 mmol) and then 2-chlorobenzoxazole (611 mL, 5.26 mmol) were added thereto, and the mixture was stirred under argon atmosphere for 14 hours at room temperature. Ethyl acetate was added to the reaction mixture. Washing was performed sequentially with water and saturated brine, followed by drying over sodium sulfate. Thereafter, the reaction mixture was subjected to filtration, concentration under reduced pressure, and purification by silica gel column chromatography (n-hexane/ethyl acetate=10/1), whereby the target compound was obtained (900 mg, 2.44 mmol, 55.8%).

Production Example 53

Synthesis of Ethyl 2-[3-[2-[N-(Benzoxazol-2-yl)-N-(naphth-1-ylmethyl)]aminoethyl]phenoxy]-2-methylpropionate

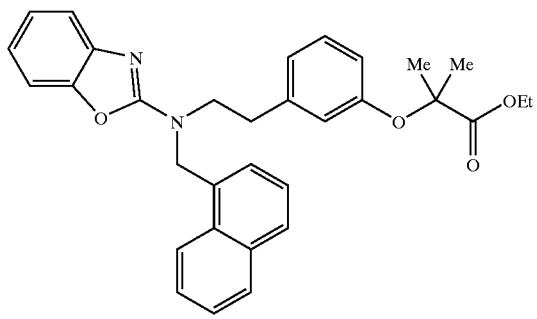

Ethyl 2-[3-[2-(N-benzoxazol-2-yl)aminoethyl]phenoxy]-2-methylpropionate (46 mg, 0.126 mmol) was dissolved in acetonitrile (2 mL). Subsequently, cesium carbonate (62 mg, 0.189 mmol) and 1-chloromethylnaphthalene (37.7 μL, 0.252 mmol) were added thereto, and the mixture was stirred for 14 hours at 80° C. The temperature of the mixture was returned to room temperature. Ethyl acetate was added. Washing was performed sequentially with water and saturated brine, followed by drying over sodium sulfate. The reaction mixture was subjected to concentration under reduced pressure and purification by silica gel column chromatography (n-hexane/ethyl acetate=10/1), whereby the target compound was obtained (56 mg, 0.110 mmol, 87.4%).

Example 170

Synthesis of 2-[3-[2-[N-(Benzoxazol-2-yl)-N-(naphth-1-ylmethyl)]aminoethyl]phenoxy]-2-methylpropionic Acid

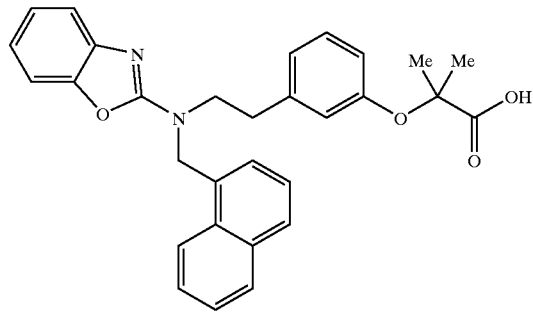

Ethyl 2-[3-[2-[N-(benzoxazol-2-yl)-N-(naphth-1-ylmethyl)]aminoethyl]phenoxy]-2-methylpropionate (56 mg, 0.110 mmol) was dissolved in methanol (2 mL)/tetrahydrofuran (1 mL). Subsequently, aqueous 2M sodium hydroxide solution was added thereto, and the mixture was stirred for three hours at room temperature. The reaction mixture was acidified with hydrochloric acid under ice-cooling. Ethyl acetate was added. Washing was performed sequentially with water and saturated brine, followed by drying over sodium sulfate. The resultant mixture was subjected to concentration under reduced pressure and purification by preparative TLC (silica gel, chloroform/methanol=10/1), whereby the target compound was obtained (53 mg, 0.110 mmol, q.).

$^1$H NMR (400 MHz, CDCl$_3$) δ 1.45 (s, 6H), 2.72 (br.s, 2H), 3.52 (br.s, 2H), 4.99 (s, 2H), 6.55–7.02 (m, 3H), 7.02–7.04 (m, 2H), 7.15–7.51 (m, 7H), 7.70–7.89 (m, 3H).

In a manner similar to that described in Example 170, the compounds of Example 171 through Example 185 were synthesized.

Example 171

2-[3-[2-[N-(Benzoxazol-2-yl)-N-ethyl]aminoethyl]phenoxy]-2-methylpropionic Acid

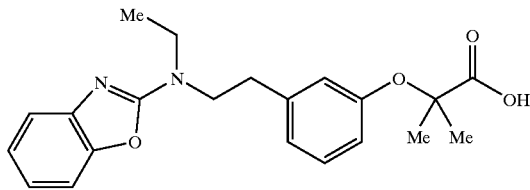

$^1$H NMR (400 MHz, CDCl$_3$) δ 1.13 (t, J=7 Hz, 3H), 1.55 (s, 6H), 2.85 (t, J=7 Hz, 2H), 3.37 (q, J=7 Hz, 2H), 3.65 (t, J=7 Hz, 2H), 6.77–6.83 (m, 3H), 6.98 (t, J=8 Hz, 1H), 7.11–7.15 (m, 2H), 7.22 (d, J=8 Hz, 1H), 7.37 (d, J=8 Hz, 1H).

Example 172

2-[3-[2-[N-(Benzoxazol-2-yl)-N-n-propyl]aminoethyl]phenoxy]-2-methylpropionic Acid

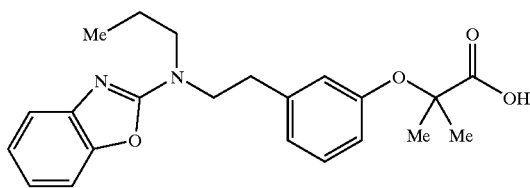

$^1$H NMR (400 MHz, CDCl$_3$) δ 0.87 (t, J=7 Hz, 3H), 1.55 (s, 6H), 1.56–1.64 (m, 2H), 2.85 (br., 2H), 3.28 (br.s, 2H), 3.65 (br.s, 2H), 6.76–6.87 (m, 3H), 6.98 (t, J=8 Hz, 1H), 7.11–7.15 (m, 2H), 7.21 (d, J=8 Hz, 1H), 7.36 (d, J=8 Hz, 1H).

Example 173

2-[3-[2-[N-(Benzoxazol-2-yl)-N-cyclohexylmethyl]
aminoethyl]phenoxy]-2-methylpropionic Acid

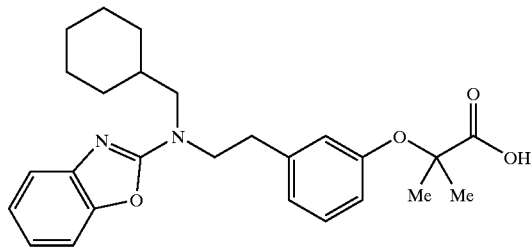

¹H NMR (400 MHz, CDCl₃) δ 0.85–0.93 (m, 2H), 1.08–1.22 (m, 4H), 1.53 (s, 6H), 1.57–1.75 (m, 5H), 2.83 (t, J=7 Hz, 2H), 3.15 (d, J=7 Hz, 2H), 3.64 (t, J=7 Hz, 2H), 6.75–6.84 (m, 3H), 6.98 (t, J=8 Hz, 1H), 7.05–7.13 (m, 2H), 7.22 (d, J=8 Hz, 1H), 7.36 (d, J=8 Hz, 1H).

Example 174

2-[3-[2-[N-(Benzoxazol-2-yl)-N-n-pentyl]
aminoethyl]phenoxy]-2-methylpropionic Acid

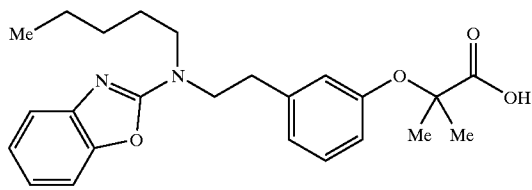

¹H NMR (400 MHz, CDCl₃) δ 0.86 (t, 7 Hz, 3H), 1.20–1.32 (m, 4H), 1.48–1.60 (m, 8H), 2.85 (br s, 2H), 3.30 (t, J=7 Hz, 2H), 3.64 (br.s, 2H), 6.79 (br.s, 2H), 6.85–6.86 (m, 1H), 6.98 (t, J=8 Hz, 1H), 7.10–7.15 (m, 2H), 7.22 (d, J=8 Hz, 1H), 7.36 (d, J=8 Hz, 1H).

Example 175

2-[3-[2-[N-(Benzoxazol-2-yl)-N-(3-methylbutyl)]
aminoethyl]phenoxy]-2-methylpropionic Acid

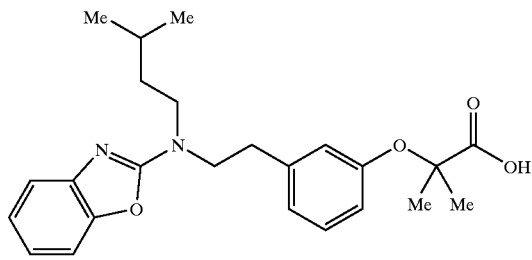

¹H NMR (400 MHz, CDCl₃) δ 0.89 (d, J=7 Hz, 6H), 1.40–1.54 (m, 3H), 1.56 (s, 6H), 2.85 (t, J=7 Hz, 2H), 3.32 (t, J=7 Hz, 2H), 3.64 (t, J=7 Hz, 2H), 6.76–6.82 (m, 2H), 6.84–6·87 (m, 1H), 6.99 (t, J=8 Hz, 1H), 7.10–7.16 (m, 2H), 7.22 (d, J=8 Hz, 1H), 7.37 (d, J=8 Hz, 1H).

Example 176

2-[3-[2-[N-(Benzoxazol-2-yl)-N-n-hexyl]
aminoethyl]phenoxy]-2-methylpropionic Acid

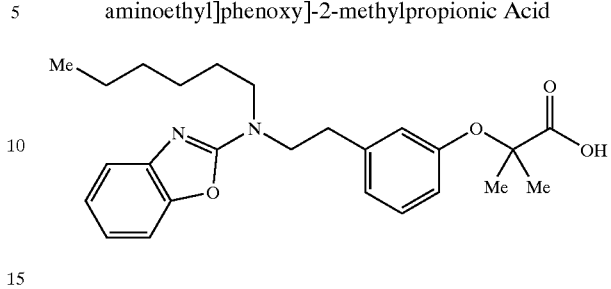

¹H NMR (400 MHz, CDCl₃) δ 0.86 (t, J=7 Hz, 3H), 1.25 (br.s, 6H), 1.57 (br.s, 8H), 2.85 (t, J=7 Hz, 2H), 3.30 (t, J=7 Hz, 2H), 3.65 (t, J=7 Hz, 2H), 6.70–6.82 (m, 2H), 6.85–6.87 (m, 1H), 6.99 (t, J=8 Hz, 1H), 7.12–7.16 (m, 2H), 7.22 (d, J=8Hz, 1H), 7.37 (d, J=8 Hz, 1H).

Example 177

2-[3-[2-[N-(Benzoxazol-2-yl)-N-n-heptyl]
aminoethyl]phenoxy]-2-methylpropionic Acid

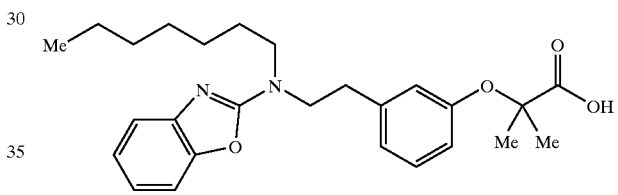

¹H NMR (400 MHz, CDCl₃) δ 0.86 (t, J=7 Hz, 3H), 1.18–1.30 (m, 8H), 1.44–1.60 (m, 8H), 2.83 (br.s, 2H), 3.31 (br.s, 2H), 3.63 (br.s, 2H), 6.72–6.86 (m, 3H), 6.97 (t, J=8 Hz, 1H), 7.08–7.15 (m, 2H), 7.21 (d, J=8 Hz, 1H), 7.35 (d, J=8 Hz, 1H).

Example 178

2-[3-[2-[N-(Benzoxazol-2-yl)-N-n-octyl]aminoethyl]
phenoxy]-2-methylpropionic Acid

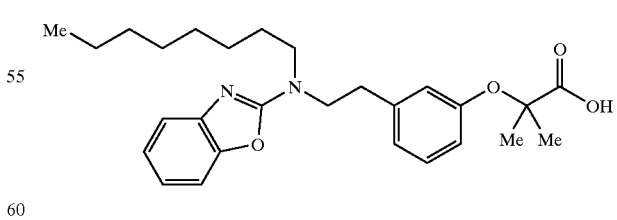

¹H NMR (400 MHz, CDCl₃) δ 0.86 (t, J=7 Hz, 3H), 1.24 (br.s, 10H), 1.56 (br.s, 8H), 2.84 (br.s, 2H), 3.30 (t, J=7 Hz, 2H), 3.65 (t, J=7 Hz, 2H), 6.72–6.86 (m, 3H), 6.99 (t, J=8 Hz, 1H), 7.08–7.15 (m, 2H), 7.21 (d, J=8 Hz, 1H), 7.37 (d, J=8 Hz, 1H).

Example 179

2-[3-[2-[N-(Benzoxazol-2-yl)-N-cyclopropylmethyl]aminoethyl]phenoxy]-2-methylpropionic Acid

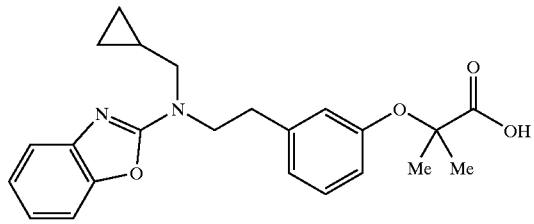

¹H NMR (400 MHz, CDCl₃) δ 0.21–0.26 (m, 2H), 0.49–0.53 (m, 2H), 0.96–1.05 (m, 1H), 1.54 (s, 6H), 2.89 (t, J=7 Hz, 2H), 3.25 (d, J=7 Hz, 2H), 3.75 (t, J=7 Hz, 2H), 6.75–6.82 (m, 2H), 6.87 (d, J=7 Hz, 1H), 6.99 (t, J=7 Hz, 1H), 7.11–7.15 (m, 2H), 7.22 (d, J=8 Hz, 1H), 7.36 (d, J=8 Hz, 1H).

Example 180

2-[3-[2-[N-Benzoxazol-2-yl)-N-(3-phenylpropyl)]aminoethyl]phenoxy]-2-methylpropionic Acid

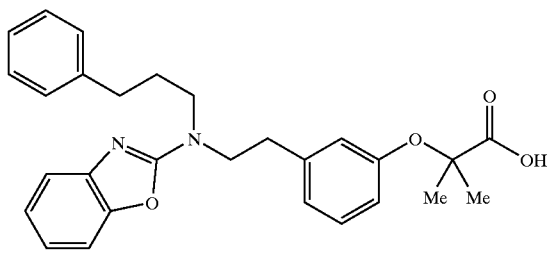

¹H NMR (400 MHz, CDCl₃) δ 1.54 (s, 6H), 1.89 (quint., J=8 Hz, 2H), 2.57 (t, J=8 Hz, 2H), 2.81 (br.s, 2H), 3.34 (t, J=7 Hz, 2H), 3.62 (br.s, 2H), 6.76–6.84 (m, 3H), 6.98 (t, J=8 Hz, 1H), 7.10–7.28 (m, 8H), 7.37 (d, J=8 Hz, 1H).

Example 181

2-[3-[2-[N-(Benzoxazol-2-yl)-N-carboxymethyl]aminoethyl]phenoxy]-2-methylpropionic Acid

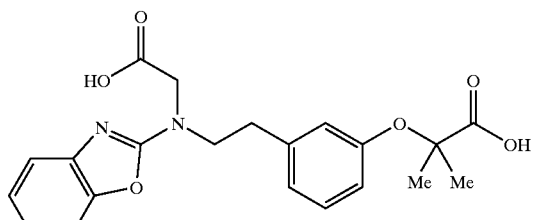

¹H NMR (400 MHz, CDCl₃) δ 1.40 (s, 6H), 2.74 (br.s, 4H), 3.68 (br.s, 2H), 6.67–6.74 (m, 3H), 6.92 (t, J=8 Hz, 1H), 7.02–7.06 (m, 2H), 7.13 (d, J=8 Hz, 1H), 7.18 (d, J=8 Hz, 1H).

Example 182

2-[3-[2-[N-(Benzoxazol-2-yl)-N-(2-butynyl)]aminoethyl]phenoxy]-2-methylpropionic Acid

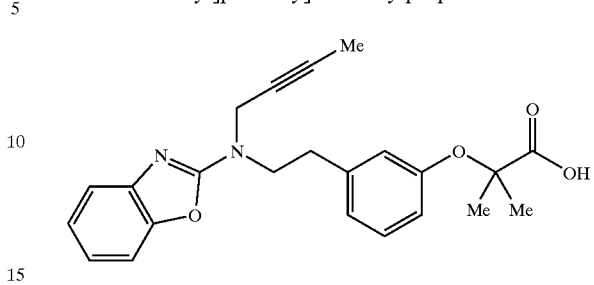

¹H NMR (400 MHz, CDCl₃) δ 1.50 (s, 6H), 1.78 (s, 3H), 2.91 (br.s, 2H), 3.79 (br.s, 2H), 4.14 (br.s, 2H), 6.73–6.90 (m, 3H), 7.00 (t, J=8 Hz, 1H), 7.10–7.16 (m, 2H), 7.23 (d, J=8 Hz, 1H), 7.36 (d, J=8 Hz, 1H).

Example 183

2-[3-[2-[N-(Benzoxazol-2-yl)-N-(5-hexenyl)]aminoethyl]phenoxy]-2-methylpropionic Acid

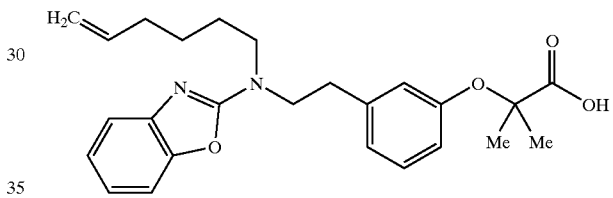

¹H NMR (400 MHz, CDCl₃) δ 1.31–1.42 (m, 2H), 1.50 (s, 6H), 1.51–1.61 (m, 2H), 2.00–2.08 (m, 2H), 2.83 (br.s, 2H), 3.32 (t, J=7 Hz, 2H), 3.63 (br.s, 2H), 4.90–5.03 (m, 2H), 5.69–5.79 (m, 1H), 6.74–6.87 (m, 3H), 6.98 (t, J=8 Hz, 1H), 7.05–7.14 (m, 2H), 7.21 (d, J=8 Hz, 1H), 7.35 (d, J=8 Hz, 1H).

Example 184

2-[3-[2-[N-(Benzoxazol-2-yl)-N-(4-benzyloxybenzyl)-]aminoethyl]phenoxy]-2-methylpropionic Acid

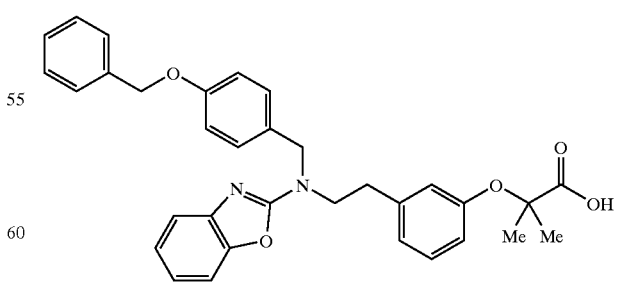

¹H NMR (400 MHz, CDCl₃) δ 1.48 (s, 6H), 2.76 (br.s, 2H), 3.56 (br.s, 2H), 4.44 (s, 2H), 4.99 (s, 2H), 6.73–6.88 (m, 6H), 6.93–7.37 (m, 11H).

Example 185

2-[3-[2-[N-(Benzoxazol-2-yl)-N-methyl]aminoethyl]phenoxy]-2-methylpropionic Acid

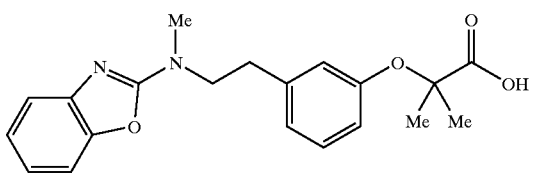

$^1$H NMR (400 MHz, CDCl$_3$) δ 1.56 (s, 6H), 2.85 (t, J=7 Hz, 2H), 2.98 (s, 3H), 3.68 (t, J=7 Hz, 2H), 6.76–6.78 (m, 2H), 6.85 (d, J=7 Hz, 1H), 6.99 (d, J=8 Hz, 1H), 7.11–7.16 (m, 2H), 7.20 (d, J=8 Hz, 1H), 7.36 (d, J=8 Hz, 1H).

Test Example 1

PPAR activating effect of the compounds falling within the scope of the present invention represented by formula (1) was determined through the following method (Proc. Natl. Acad. Sci., 92, pp. 7297–7301, 1995; Journal of Biological Chemistry, 269, pp. 31012–31018, 1994; and Proc. Natl. Acad. Sci, 98, pp. 5306–5311, 2001).

a. Method of Determination

Transfection Assay

Every transfection assays were performed on COS cells, which are cell strains originating from the kidney of *Cercopithecus aethiops*, by using lipofectamine procedure. COS cells were cultured under CO$_2$ (5%) by use of a DMEM medium containing 10% fetal bovine serum, glutamic acid, and an antibiotic.

pSG5hPPARα, pSG5hPPARγ, or pcDNA3hPPARδ was used as a wild-type human PPAR expression vector. Firefly luciferase reporter plasmid containing 6-repeated PPAR responsive element present in a human apoAII promoter was used as a reporter vector. A β-galactosidase expression vector was employed as an internal standard.

Transiently transfected cells were incubated with or without compound. And after 16 hours, luciferase activity and β-galactosidase of cell lysate were determined.

In the present test, each compound was dissolved in and diluted with dimethyl sulfoxide (DMSO), and the DMSO concentration of the DMEM medium (containing 0.2% serum) was adjusted to 0.1% upon treatment of cells. As positive control compounds, WY 14643, troglitazone (Journal of Medicinal Chemistry, 43, pp. 527–550, 2000), and GW 501516 (Proc. Natl. Acad. Sci., 98, pp. 5306–5311, 2001) were used with respect to PPARα, PPARγ, and PPARδ, respectively.

b. Results

Table 1 shows agonist activity (to hPPARα, hPPARγ, hPPARδ) of the compounds of the present invention.

TABLE 1

| | hPPAR; EC$_{50}$ (μM) | | |
|---|---|---|---|
| Example No. | α | γ | δ |
| 1 | 0.01 | 0.2 | >10 |
| 6 | 0.01 | 0.2 | >10 |
| 12 | 0.003 | 0.1 | 0.5 |
| 29 | 0.1 | >10 | >10 |
| 41 | 0.01 | 0.2 | 1.8 |
| 46 | 0.01 | 0.4 | 1.1 |

TABLE 1-continued

| | hPPAR; EC$_{50}$ (μM) | | |
|---|---|---|---|
| Example No. | α | γ | δ |
| 48 | 0.01 | 0.7 | 4.5 |
| 55 | 0.002 | 0.1 | 0.6 |
| 56 | 0.001 | 0.1 | 1.0 |
| 59 | 0.003 | 0.1 | >10 |
| 63 | 0.002 | 0.1 | 0.9 |
| 69 | 0.0003 | 0.2 | >10 |
| 70 | 0.001 | 0.4 | >10 |
| 74 | 0.1 | >10 | >10 |
| 114 | 0.01 | 0.4 | >10 |
| 121 | 0.004 | 0.1 | >10 |
| 132 | 0.03 | 2.0 | >10 |
| 133 | 0.01 | 0.3 | 3.0 |
| 135 | 0.01 | >10 | >10 |
| 155 | 0.01 | 0.5 | 0.3 |
| WY 14643 | 1.5 | | |
| troglitazone | | 0.1 | |
| GW 501516 | | | 0.5 |

Activation factors; of Example 1 with respect to each isoform of PPARs at EC50 for activating hPPARα and at the corresponding 10-time concentration are summarized in FIG. 1. The activation factor is defined as a ratio of obtained activity to control value, which is obtained when a liquid contains only the solvent (DMSO) and no test compound. As is clear from FIG. 1, the compound of Example 1 does not activate hPPARγ and hPPARδ, even at the 10-time concentration of EC$_{50}$ value for activating hPPARα.

As is clear from the results, the compounds of the present invention exert PPARα-selective activation effect.

Industrial Applicability

The compound of the present invention exerts an effect of selectively activating PPARα among other PPARs, and is usefully employed as a drug for preventing and/or treating, without accompanying obesity or increase in body weight, diseases including hyperlipidemia, arteriosclerosis, diabetes, complications of diabetes, inflammation, and heart diseases.

What is claimed is:

1. A benzoxazole compound represented by the following formula (1):

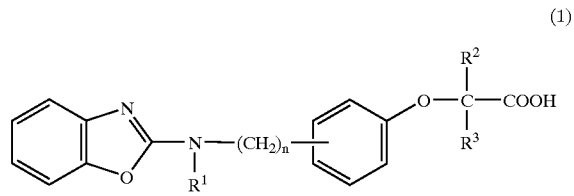

(wherein R$^1$ represents a hydrogen atom, a C$_{1-8}$ alkyl group, a C$_{2-8}$ alkenyl group, a C$_{2-8}$ alkynyl group, a C$_{3-7}$ cycloalkyl group, a C$_{3-7}$ cycloalkyl-C$_{1-8}$ alkyl group, a C$_{6-10}$ aryl-C$_{1-8}$ alkyl group (the C$_{6-10}$ aryl moiety may have one or two substituents selected from among a halogen atom, a hydroxyl group, a nitro group, an amino group, a di-C$_{1-4}$ alkylamino group, a C$_{1-4}$ alkyl group, a C$_{1-4}$ alkoxy group, a benzyloxy group, a phenylsulfonylmethyl group, and a C$_{1-4}$ alkanesulfonyloxy group), a pyridyl-C$_{1-8}$ alkyl group, a C$_{1-8}$ alkoxycarbonyl-C$_{1-8}$ alkyl group, or a carboxy-C$_{1-8}$ alkyl group; each of R$^2$ and R$^3$, which are identical to or different from each other, represents a hydrogen atom, a methyl group, or an ethyl group; and n represents a number of 1 to 3) or a salt thereof.

2. A benzoxazole compound or a salt thereof as described in claim 1, wherein $R^1$ is a $C_{1-8}$ alkyl group, a $C_{2-8}$ alkynyl group, or a $C_{6-10}$ aryl-$C_{1-8}$ alkyl group (the $C_{6-10}$ aryl moiety may have one or two substituents selected from among a halogen atom, a hydroxyl group, a nitro group, an amino group, a di-$C_{1-4}$ alkylamino group, a $C_{1-4}$ alkyl group, a $C_{1-4}$ alkoxy group, a benzyloxy group, a phenylsulfonylmethyl group, and a $C_{1-4}$ alkanesulfonyloxy group).

3. A benzoxazole compound or a salt thereof as described in claim 1, wherein $R^1$ is a $C_{1-8}$ alkyl group, a $C_{2-8}$ alkynyl group, or a $C_{6-10}$ aryl-$C_{1-4}$ alkyl group (the $C_{6-10}$ aryl moiety may have one or two substituents selected from among a halogen atom, a nitro group, and a di-$C_{1-4}$ alkylamino group).

4. A benzoxazole compound or a salt thereof as described in claim 1, wherein $R^2$ and $R^3$ are simultaneously hydrogen atoms or methyl groups; $R^2$ and $R^3$ are a methyl group and a hydrogen atom; or $R^2$ and $R^3$ are an ethyl group and a hydrogen atom.

5. A compound selected from among the following compounds: 2-[3-[[N-(benzoxazol-2-yl)-N-(4-chlorobenzyl)]aminomethyl]phenoxy]-2-methylpropionic acid, 2-[3-[[N-(benzoxazol-2-yl)-N-n-octyl]aminomethyl]phenoxy]-2-methylpropionic acid, 2-[4-[[N-(benzoxazol-2-yl)-N-(naphth-1-ylmethyl)]aminomethyl]phenoxy]-2-methylpropionic acid, 2-[4-[[N-(benzoxazol-2-yl)-N-(2-nitrobenzyl)]aminomethyl]phenoxy]-2-methylpropionic acid, 2-[3-[[N-(benzoxazol-2-yl)-N-(4-dimethylaminobenzyl)]aminomethyl]phenoxy]-2-methylpropionic acid, 3-[[N-(benzoxazol-2-yl)-N-n-heptyl]aminomethyl]phenoxyacetic acid, 3-[[N-(benzoxazol-2-yl)-N-n-octyl]aminomethyl]phenoxyacetic acid, 2-[3-[[N-(benzoxazol-2-yl)-N-(3-phenylpropyl)]aminomethyl]phenoxy]butyric acid, 2-[3-[[N-(benzoxazol-2-yl)-N-(3-(4-chlorophenyl)propyl)]aminomethyl]phenoxy]butyric acid, 2-[3-[[N-(benzoxazol-2-yl)-N-n-octyl]aminomethyl]phenoxy]butyric acid, 2-[3-[[N-(benzoxazol-2-yl)-N-(3-(4-chlorophenyl)propyl)]aminomethyl]phenoxy]propionic acid, 2-[3-[[N-(benzoxazol-2-yl)-N-n-octyl]aminomethyl]phenoxy]propionic acid, 2-[3-[[N-(benzoxazol-2-yl)-N-(3-phenylpropyl)]aminomethyl]phenoxy]propionic acid, 2-[3-[[N-(benzoxazol-2-yl)-N-n-propyl]aminomethyl]phenoxy]propionic acid, 2-[4-[3-[N-(benzoxazol-2-yl)-N-ethyl]aminopropyl]phenoxy]-2-methylpropionic acid, 2-[3-[3-[N-(benzoxazol-2-yl)-N-(2-butynyl)]aminopropyl]phenoxy]-2-methylpropionic acid, 2-[4-[3-[N-(benzoxazol-2-yl)-N-n-propyl]aminopropyl]phenoxy]-2-methylpropionic acid, 2-[4-[3-[N-(benzoxazol-2-yl)-N-isopropyl]aminopropyl]phenoxy]-2-methylpropionic acid, 2-[3-[[N-(benzoxazol-2-yl)-N-(naphth-1-ylmethyl)]aminomethyl]phenoxy]-2-methylpropionic acid, and 2-[2-[3-[N-(benzoxazol-2-yl)-N-n-octyl]aminopropyl]phenoxy]-2-methylpropionic acid and a salt thereof.

6. 2-[3-[[N-(Benzoxazol-2-yl)-N-(4-chlorobenzyl)]aminomethyl]phenoxy]-2-methylpropionic acid or a salt thereof.

7. A pharmaceutical composition containing a benzoxazole compound as recited in any one of claims 1 to 6 or a salt thereof and a pharmaceutically acceptable carrier.

8. A method for treating a disease selected from among hyperlipidemia, arteriosclerosis, diabetes, complications of diabetes, inflammation, and heart diseases, the method being characterized by comprising administering a benzoxazole compound as recited in any one of claims 1 to 6 in an effective amount.

* * * * *